(12) United States Patent
Achtien et al.

(10) Patent No.: US 12,349,738 B2
(45) Date of Patent: Jul. 8, 2025

(54) USER INTERFACE AND USER EXPERIENCE FOR A VAPORIZER DEVICE

(71) Applicant: JUUL Labs, Inc., San Francisco, CA (US)

(72) Inventors: Nicholas Achtien, San Francisco, CA (US); Raffi Aghapekian, San Francisco, CA (US); Ariel Atkins, San Francisco, CA (US); Brandon Cheung, San Francisco, CA (US); Adam Bowen, San Mateo, CA (US); Gal A. Cohen, Mill Valley, CA (US); Jacob Honig, San Francisco, CA (US); Alexander J. Gould, Portola Valley, CA (US); Nicholas J. Hatton, Oakland, CA (US); Chelsea Kania, San Francisco, CA (US); James Monsees, San Francisco, CA (US); Roxolana Wacyk, San Francisco, CA (US); Casey S. Yost, Daly City, CA (US)

(73) Assignee: JUUL LABS, INC., Washington, DC (US)

( * ) Notice: Subject to any disclaimer, the term of this patent is extended or adjusted under 35 U.S.C. 154(b) by 310 days.

(21) Appl. No.: 16/765,828

(22) PCT Filed: Nov. 21, 2018

(86) PCT No.: PCT/US2018/062328
§ 371 (c)(1),
(2) Date: May 20, 2020

(87) PCT Pub. No.: WO2019/104227
PCT Pub. Date: May 31, 2019

(65) Prior Publication Data
US 2020/0352249 A1    Nov. 12, 2020

Related U.S. Application Data

(60) Provisional application No. 62/590,107, filed on Nov. 22, 2017.

(51) Int. Cl.
A24F 40/60    (2020.01)
A24F 40/10    (2020.01)
(Continued)

(52) U.S. Cl.
CPC .............. *A24F 40/60* (2020.01); *A24F 40/50* (2020.01); *A24F 40/53* (2020.01); *A24F 40/65* (2020.01); *A24F 40/10* (2020.01)

(58) Field of Classification Search
CPC .......... A24F 40/60; A24F 40/53; A24F 40/50; A24F 40/10; A24B 15/167; A61M 11/042;
(Continued)

(56) References Cited

U.S. PATENT DOCUMENTS 5,610,635 A    3/1997    Murray et al.
8,402,976 B2   3/2013    Fernando et al.
(Continued)

FOREIGN PATENT DOCUMENTS

AU    2017202891 B2    5/2019
CN    201067079        6/2008
(Continued)

OTHER PUBLICATIONS

PCT/US2018/062328, Nov. 21, 2018, WO-2019104227-A1.
(Continued)

*Primary Examiner* — Jean F Duverne
(74) *Attorney, Agent, or Firm* — Mintz, Levin, Cohn, Ferris, Glovsky and Popeo, P.C.

(57) ABSTRACT

Vaporizers and vaporizer systems, which can include a device in communication with a vaporizer, can include one
(Continued)

or more features related to control of functions and/or features of the vaporizer, identification of a cartridge and/or a vaporizable material in the cartridge, data exchange (either one-way or two-way) between a cartridge and a vaporizer with which the cartridge is engaged, and the like.

15 Claims, 38 Drawing Sheets

(51) Int. Cl.
  *A24F 40/50* (2020.01)
  *A24F 40/53* (2020.01)
  *A24F 40/65* (2020.01)

(58) Field of Classification Search
  CPC .. A61M 2016/0024; A61M 2205/3584; A61M 2205/3569
  See application file for complete search history.

(56) References Cited

U.S. PATENT DOCUMENTS

| | | |
|---|---|---|
| 8,550,069 B2 | 10/2013 | Alelov |
| 8,807,131 B1 | 8/2014 | Tunnell et al. |
| 9,247,773 B2 | 2/2016 | Memari et al. |
| 9,439,455 B2 | 9/2016 | Alarcon et al. |
| 9,462,832 B2 | 10/2016 | Lord |
| 9,609,895 B2 | 4/2017 | Galloway et al. |
| 9,763,478 B2 | 9/2017 | Cameron et al. |
| 9,770,055 B2 * | 9/2017 | Cameron ............... A24F 40/30 |
| 9,877,519 B2 | 1/2018 | Xiang |
| 9,888,723 B2 | 2/2018 | Cameron et al. |
| 10,058,124 B2 | 8/2018 | Monsees et al. |
| 10,058,128 B2 | 8/2018 | Cameron et al. |
| 10,085,486 B2 | 10/2018 | Cameron et al. |
| 10,131,532 B2 | 11/2018 | Murison et al. |
| 10,292,427 B2 | 5/2019 | Cameron et al. |
| 10,321,711 B2 | 6/2019 | Henry, Jr. et al. |
| 10,327,474 B2 | 6/2019 | Hawes et al. |
| 10,375,990 B2 | 8/2019 | Lord |
| 10,448,670 B2 | 10/2019 | Talon et al. |
| 10,564,655 B2 | 2/2020 | Blackley |
| 10,945,463 B2 | 3/2021 | Dickens et al. |
| 2005/0066961 A1 | 3/2005 | Rand |
| 2009/0266358 A1 | 10/2009 | Rock et al. |
| 2010/0191385 A1 | 7/2010 | Goodnow et al. |
| 2010/0234987 A1 | 9/2010 | Benschop et al. |
| 2011/0036346 A1 | 2/2011 | Cohen et al. |
| 2011/0097060 A1 | 4/2011 | Buzzetti |
| 2011/0150294 A1 | 6/2011 | Eckhoff et al. |
| 2012/0255546 A1 | 10/2012 | Alarcon et al. |
| 2012/0291791 A1 | 11/2012 | Pradeep |
| 2012/0304990 A1 | 12/2012 | Todd |
| 2013/0220315 A1 | 8/2013 | Conley et al. |
| 2013/0284192 A1 | 10/2013 | Peleg et al. |
| 2013/0311001 A1 | 11/2013 | Hampiholi |
| 2013/0319439 A1 * | 12/2013 | Gorelick ............... A24F 40/53 131/329 |
| 2013/0340775 A1 * | 12/2013 | Juster ............... H04L 67/01 131/273 |
| 2014/0078164 A1 | 3/2014 | Chan et al. |
| 2014/0123989 A1 | 5/2014 | Lamothe |
| 2014/0144429 A1 | 5/2014 | Wensley et al. |
| 2014/0182608 A1 | 7/2014 | Egoyants et al. |
| 2014/0190496 A1 | 7/2014 | Wensley et al. |
| 2014/0246035 A1 | 9/2014 | Minskoff et al. |
| 2014/0278250 A1 | 9/2014 | Smith et al. |
| 2014/0283859 A1 | 9/2014 | Minskoff et al. |
| 2014/0334804 A1 | 11/2014 | Choi |
| 2014/0338685 A1 | 11/2014 | Amir |
| 2014/0345635 A1 | 11/2014 | Rabinowitz et al. |
| 2015/0020822 A1 | 1/2015 | Janardhan et al. |
| 2015/0020825 A1 | 1/2015 | Galloway et al. |
| 2015/0020831 A1 | 1/2015 | Weigensberg et al. |
| 2015/0064672 A1 | 3/2015 | Bars |
| 2015/0101625 A1 | 4/2015 | Newton et al. |
| 2015/0114407 A1 | 4/2015 | Duncan et al. |
| 2015/0122252 A1 | 5/2015 | Frija |
| 2015/0136155 A1 | 5/2015 | Verleur et al. |
| 2015/0136158 A1 | 5/2015 | Stevens et al. |
| 2015/0164144 A1 | 6/2015 | Liu |
| 2015/0181945 A1 | 7/2015 | Tremblay |
| 2015/0208731 A1 | 7/2015 | Malamud et al. |
| 2015/0216237 A1 | 8/2015 | Wensley et al. |
| 2015/0257445 A1 | 9/2015 | Henry et al. |
| 2015/0258289 A1 | 9/2015 | Henry et al. |
| 2015/0272220 A1 | 10/2015 | Spinka et al. |
| 2015/0272223 A1 | 10/2015 | Weigensberg et al. |
| 2015/0288468 A1 | 10/2015 | Xiang |
| 2015/0305409 A1 | 10/2015 | Verleur et al. |
| 2015/0359263 A1 | 12/2015 | Bellinger |
| 2016/0004469 A1 | 1/2016 | Yun et al. |
| 2016/0021930 A1 * | 1/2016 | Minskoff ............... A24F 40/51 392/395 |
| 2016/0057811 A1 | 2/2016 | Alarcon et al. |
| 2016/0063235 A1 | 3/2016 | Tussy |
| 2016/0081394 A1 | 3/2016 | Alarcon et al. |
| 2016/0089508 A1 | 3/2016 | Smith et al. |
| 2016/0106151 A1 | 4/2016 | Swepston et al. |
| 2016/0106936 A1 | 4/2016 | Kimmel |
| 2016/0143361 A1 | 5/2016 | Juster et al. |
| 2016/0157524 A1 | 6/2016 | Bowen et al. |
| 2016/0161459 A1 | 6/2016 | Rouse et al. |
| 2016/0166786 A1 | 6/2016 | Kinzer |
| 2016/0198767 A1 | 7/2016 | Verleur |
| 2016/0219933 A1 | 8/2016 | Henry et al. |
| 2016/0219938 A1 | 8/2016 | Mamoun et al. |
| 2016/0278435 A1 | 9/2016 | Choukroun et al. |
| 2016/0278436 A1 | 9/2016 | Verleur et al. |
| 2016/0324217 A1 | 11/2016 | Cameron |
| 2016/0325055 A1 | 11/2016 | Cameron |
| 2016/0331022 A1 | 11/2016 | Cameron |
| 2016/0331023 A1 | 11/2016 | Cameron |
| 2016/0331024 A1 | 11/2016 | Cameron |
| 2016/0331025 A1 | 11/2016 | Cameron |
| 2016/0331026 A1 | 11/2016 | Cameron |
| 2016/0331027 A1 | 11/2016 | Cameron |
| 2016/0331034 A1 | 11/2016 | Cameron |
| 2016/0331036 A1 | 11/2016 | Cameron |
| 2016/0331859 A1 | 11/2016 | Cameron |
| 2016/0334119 A1 | 11/2016 | Cameron |
| 2016/0334847 A1 | 11/2016 | Cameron |
| 2016/0337141 A1 | 11/2016 | Cameron |
| 2016/0337362 A1 | 11/2016 | Cameron |
| 2016/0337444 A1 | 11/2016 | Cameron |
| 2016/0360789 A1 | 12/2016 | Hawes et al. |
| 2016/0363570 A1 | 12/2016 | Blackley |
| 2016/0363917 A1 | 12/2016 | Blackley |
| 2016/0366946 A1 | 12/2016 | Murison et al. |
| 2016/0367925 A1 | 12/2016 | Blackley |
| 2016/0370335 A1 | 12/2016 | Blackley |
| 2016/0374399 A1 | 12/2016 | Monsees et al. |
| 2017/0018000 A1 | 1/2017 | Cameron |
| 2017/0020188 A1 | 1/2017 | Cameron |
| 2017/0020195 A1 | 1/2017 | Cameron |
| 2017/0020196 A1 | 1/2017 | Cameron |
| 2017/0020197 A1 | 1/2017 | Cameron |
| 2017/0027229 A1 | 2/2017 | Cameron |
| 2017/0034324 A1 | 2/2017 | Zhang et al. |
| 2017/0042230 A1 | 2/2017 | Cameron |
| 2017/0042231 A1 | 2/2017 | Cameron |
| 2017/0042252 A1 | 2/2017 | Takeuchi et al. |
| 2017/0046357 A1 * | 2/2017 | Cameron ............... A24F 40/30 |
| 2017/0046738 A1 | 2/2017 | Cameron |
| 2017/0048691 A1 | 2/2017 | Liu |
| 2017/0055588 A1 | 3/2017 | Cameron |
| 2017/0086496 A1 | 3/2017 | Cameron |
| 2017/0086497 A1 | 3/2017 | Cameron |
| 2017/0086503 A1 | 3/2017 | Cameron |
| 2017/0086504 A1 | 3/2017 | Cameron |
| 2017/0091853 A1 | 3/2017 | Cameron |
| 2017/0092106 A1 | 3/2017 | Cameron |
| 2017/0093960 A1 | 3/2017 | Cameron |

(56) References Cited

U.S. PATENT DOCUMENTS

| | | |
|---|---|---|
| 2017/0093981 A1 | 3/2017 | Cameron |
| 2017/0119058 A1 | 5/2017 | Cameron |
| 2017/0135407 A1 | 5/2017 | Cameron |
| 2017/0135408 A1 | 5/2017 | Cameron |
| 2017/0135409 A1 | 5/2017 | Cameron |
| 2017/0135411 A1 | 5/2017 | Cameron |
| 2017/0135412 A1 | 5/2017 | Cameron |
| 2017/0136193 A1 | 5/2017 | Cameron |
| 2017/0136194 A1 | 5/2017 | Cameron |
| 2017/0136301 A1 | 5/2017 | Cameron |
| 2017/0156397 A1 | 6/2017 | Sur et al. |
| 2017/0156399 A1 | 6/2017 | Freeman et al. |
| 2017/0157341 A1 | 6/2017 | Pandya et al. |
| 2017/0170439 A1 | 6/2017 | Jarvis et al. |
| 2017/0180067 A1 | 6/2017 | Poornachandran et al. |
| 2017/0181474 A1 | 6/2017 | Cameron |
| 2017/0181475 A1 | 6/2017 | Cameron |
| 2017/0185364 A1 | 6/2017 | Cameron |
| 2017/0196270 A1 | 7/2017 | Vick et al. |
| 2017/0208867 A1 | 7/2017 | Li et al. |
| 2017/0215478 A1 | 8/2017 | Harrison et al. |
| 2017/0215480 A1 | 8/2017 | Qiu |
| 2017/0231273 A1 | 8/2017 | Xiang |
| 2017/0245550 A1 | 8/2017 | Freelander |
| 2017/0258136 A1 | 9/2017 | Hawes et al. |
| 2017/0262064 A1 | 9/2017 | Ofir et al. |
| 2017/0266397 A1 | 9/2017 | Mayle et al. |
| 2017/0273357 A1 | 9/2017 | Barbuck |
| 2017/0303590 A1 | 10/2017 | Cameron et al. |
| 2017/0303593 A1 | 10/2017 | Cameron et al. |
| 2017/0303594 A1 | 10/2017 | Cameron et al. |
| 2017/0304563 A1 | 10/2017 | Adelson |
| 2017/0304567 A1 | 10/2017 | Adelson |
| 2017/0309091 A1 | 10/2017 | Cameron et al. |
| 2017/0318861 A1 | 11/2017 | Thorens |
| 2017/0332702 A1 | 11/2017 | Cameron et al. |
| 2017/0360097 A1 | 12/2017 | Xiang |
| 2017/0368273 A1 | 12/2017 | Rubin |
| 2018/0020720 A1 | 1/2018 | Matischek et al. |
| 2018/0043114 A1 | 2/2018 | Bowen et al. |
| 2018/0132526 A1 | 5/2018 | Davis et al. |
| 2018/0153219 A1 | 6/2018 | Verleur et al. |
| 2018/0153221 A1 | 6/2018 | Verleur et al. |
| 2018/0160733 A1 | 6/2018 | Leadley et al. |
| 2018/0184722 A1 | 7/2018 | Murison et al. |
| 2018/0263288 A1 | 9/2018 | Goldstein et al. |
| 2018/0325176 A1 | 11/2018 | Burseg |
| 2019/0104762 A1 | 4/2019 | Cameron |
| 2019/0158938 A1 | 5/2019 | Bowen et al. |
| 2019/0272359 A1* | 9/2019 | Popplewell ............. G06F 21/32 |
| 2019/0307170 A1 | 10/2019 | Zarifian et al. |
| 2020/0058057 A1 | 2/2020 | Ouyang |
| 2021/0345681 A1 | 11/2021 | Cameron |

FOREIGN PATENT DOCUMENTS

| | | | |
|---|---|---|---|
| CN | 203289647 U | | 11/2013 |
| CN | 204275207 | | 4/2015 |
| CN | 104797152 A | | 7/2015 |
| CN | 204466899 | | 7/2015 |
| CN | 104839892 B | | 8/2015 |
| CN | 105050434 A | | 11/2015 |
| CN | 105342009 B | | 2/2016 |
| CN | 105722417 A | | 6/2016 |
| CN | 106164958 A | | 11/2016 |
| CN | 106455717 | | 2/2017 |
| CN | 106462862 A | | 2/2017 |
| CN | 106535673 A | | 3/2017 |
| CN | 106573118 A | | 4/2017 |
| CN | 106573123 A | | 4/2017 |
| CN | 106594797 A | | 4/2017 |
| CN | 106686995 A | | 5/2017 |
| CN | 106998821 A | | 8/2017 |
| CN | 107438372 A | | 12/2017 |
| CN | 108038161 A | | 5/2018 |
| CN | 111213920 A | | 6/2020 |
| CN | 212464894 U | | 2/2021 |
| EP | 2110034 A1 | | 10/2009 |
| EP | 2399636 A1 | | 12/2011 |
| EP | 3000245 B1 | | 3/2016 |
| EP | 3463535 B1 | | 8/2022 |
| GB | 2507103 A | | 4/2014 |
| GB | 2527403 A | | 12/2015 |
| GR | 20120100199 A | | 11/2013 |
| JP | 2949114 B1 | | 9/1999 |
| JP | 2006180378 A | | 7/2006 |
| JP | 2007172605 A | | 7/2007 |
| JP | 2008501406 A | | 1/2008 |
| JP | 2008059382 A | | 3/2008 |
| JP | 2013524835 A | | 6/2013 |
| JP | 2016114402 A | | 6/2016 |
| JP | 2017513513 A | | 6/2017 |
| JP | 2019521739 A | | 8/2019 |
| KR | 10-2009-0119127 A | | 11/2009 |
| KR | 10-2010-0080114 A | | 7/2010 |
| KR | 101523088 B1 | | 5/2015 |
| KR | 20150064754 A | | 6/2015 |
| KR | 102535301 | | 10/2021 |
| RU | 2606942 C2 | | 1/2017 |
| TW | 201330884 A | | 8/2013 |
| TW | M548451 U | | 9/2017 |
| TW | I763672 B | | 5/2022 |
| WO | WO-2011160788 A1 | | 12/2011 |
| WO | WO-2014058678 A1 | | 4/2014 |
| WO | WO-2014060267 A2 | | 4/2014 |
| WO | WO-2014068504 A2 | | 5/2014 |
| WO | WO-2015031836 A1 | | 3/2015 |
| WO | WO-2015038981 A2 | | 3/2015 |
| WO | WO-2015063126 A1 | | 5/2015 |
| WO | WO-2015138560 A1 | | 9/2015 |
| WO | WO-2015161485 A1 | | 10/2015 |
| WO | WO-2015161486 A1 | | 10/2015 |
| WO | WO- 2015165747 A1 | | 11/2015 |
| WO | WO-2015167000 A1 | | 11/2015 |
| WO | WO-2016008096 A1 | | 1/2016 |
| WO | WO-2016009202 A1 | | 1/2016 |
| WO | WO-2016058992 A2 | | 4/2016 |
| WO | WO-2016065413 A1 | | 5/2016 |
| WO | WO-2016123307 A1 | | 8/2016 |
| WO | WO-2016187110 A1 | | 11/2016 |
| WO | 2017/055801 A1 | | 4/2017 |
| WO | WO-2017054627 A1 | | 4/2017 |
| WO | WO-2017056103 A1 | | 4/2017 |
| WO | WO-2017205692 A1 * | 11/2017 | ............. A24F 40/10 |
| WO | WO-2020006311 A1 | | 1/2020 |

OTHER PUBLICATIONS

Pham, et al., (Feb. 28, 2011)"A Clustering Approach for Collaborative Filtering Recommendation Using Social Network Analysis", Journal of Universal Computer Science, 17(4):583-604.

Grotenhermen, et al., (Sep. 2005) "Developing Science-Based Per Se Limits for Driving under the Influence of Cannabis (DUIC)—Findings and Recommendations by an Expert Panel", Canorml, Available at: http://www.canorml.org/healthfacts/DUICreport. 2005, 49 pages.

Behm, et al., (Jan. 1993) Clinical Evaluation of a Citric Acid Inhaler for Smoking Cessation, Drug and Alcohol Dependence, 31(2):131-138.

* cited by examiner

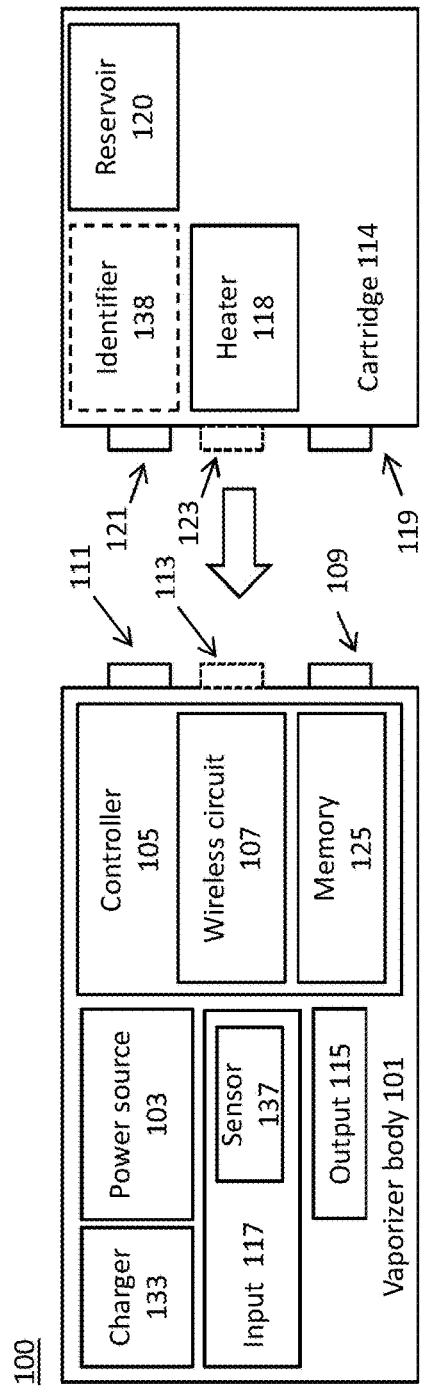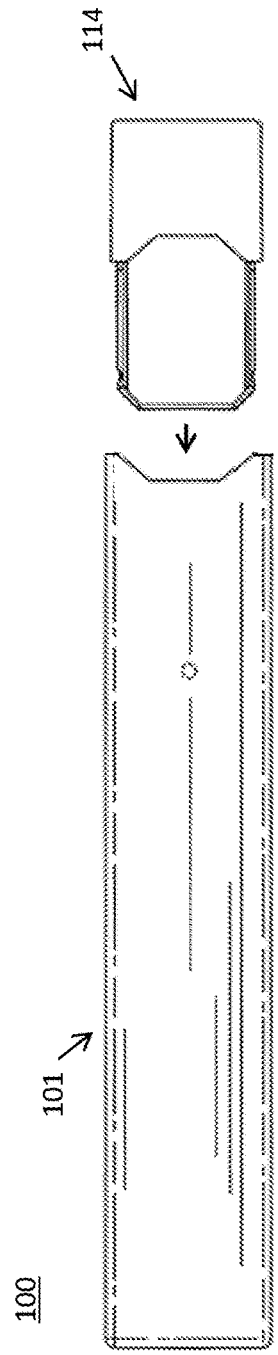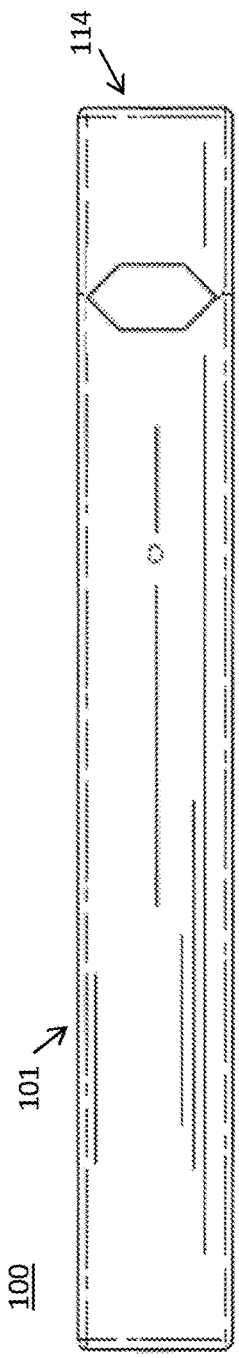

FIG. 7B

Create your account first | last
email
password

◉ I'm over 18
◉ Send me email updates
◉ I agree to the :
  terms of service
  privacy policy

[ GO ]

●○○○○

Setup

FIG. 7A

Create your account email
password what's my password again?

[ GO ]

Password

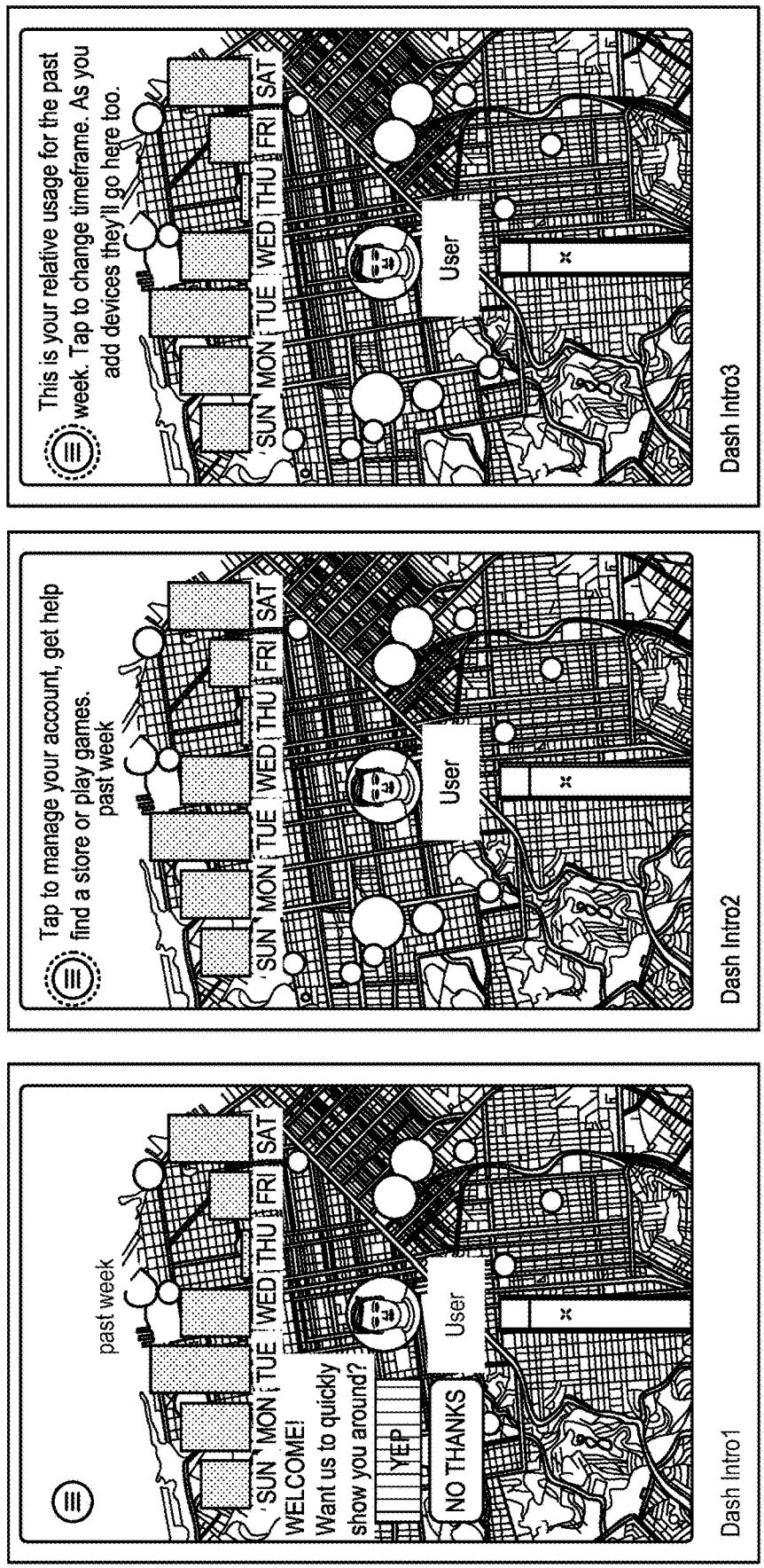

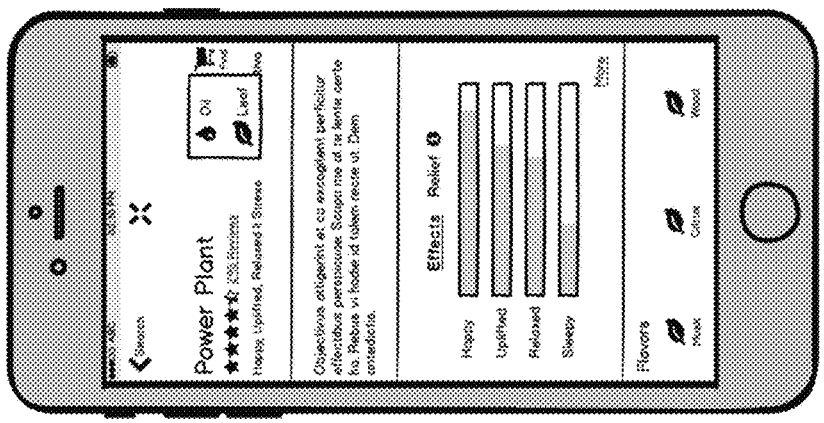
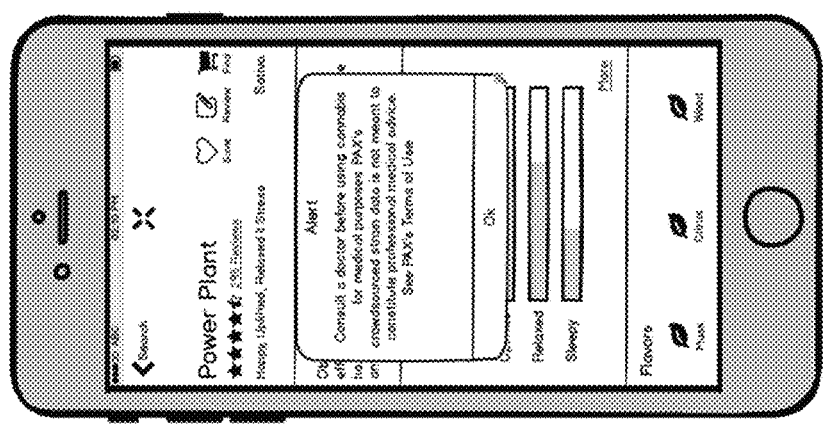
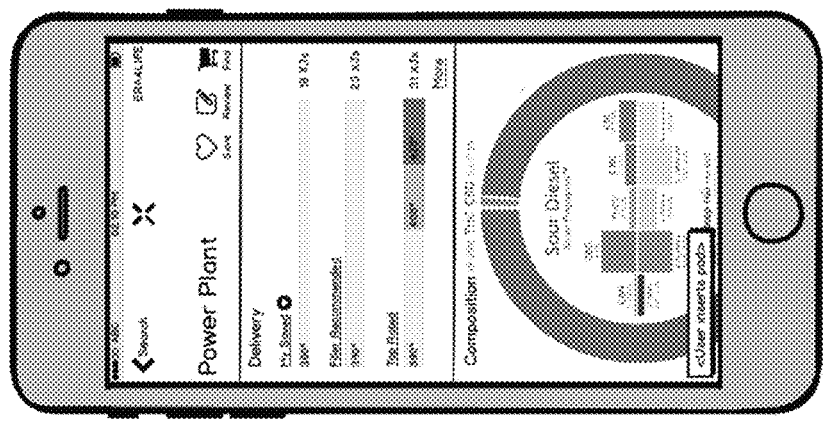
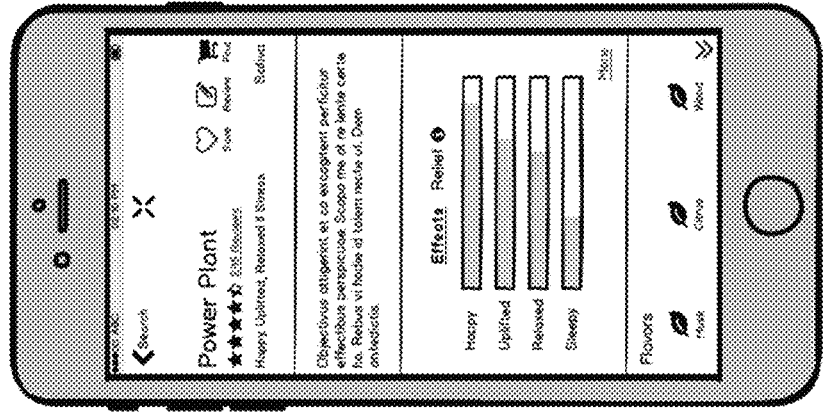
FIG. 27D
FIG. 27C
FIG. 27B
FIG. 27A

USER INTERFACE AND USER EXPERIENCE FOR A VAPORIZER DEVICE

CROSS-REFERENCE TO RELATED APPLICATIONS

This application claims priority to U.S. Provisional Patent Application No. 62/590,107, titled "User Interface and User Experience For a Vaporizer Device," filed on Nov. 22, 2017, which is related to U.S. patent application Ser. No. 15/605,890, titled "Control of an Electronic Vaporizer", filed on May 25, 2017, which claims priority to U.S. Provisional Patent Application No. 62/341,579, titled "Control of an Electronic Vaporizer," filed on May 25, 2016, the disclosures of which are incorporated herein by reference in their entirety.

TECHNICAL FIELD

The devices, systems and methods described herein relate to vaporizing devices, for example electronic vaporizer devices, and to methods of using, controlling, making, etc. such devices, which may optionally include devices that include two or more parts, such as a cartridge containing a vaporizable substance and a body part that includes one or more other components.

BACKGROUND

Vaporizing devices, which can also be referred to as electronic vaporizer devices or e-vaporizer devices, can be used for delivery of vapor containing one or more active ingredients by inhalation of the vapor by a user of the vaporizing device. Electronic vaporizer devices are gaining increasing popularity both for prescriptive medical use, in delivering medicaments, and for consumption of tobacco and other plant-based smokeable materials. Electronic vaporizer devices in particular may be portable, self-contained and convenient for use. Typically, such devices are controlled by one or more switches, buttons or the like (controls) on the vaporizer, although a number of devices that may wirelessly communicate with an external controller (e.g., smartphone) have recently become available.

Such wireless control has been primarily limited to temperature setting and other features that were already, and perhaps more conveniently, performed on the device itself. These systems may not automate or calibrate the operation of the device based on detection of the material or type of material loaded into the device. Such systems also may not typically track dosage and/or allow modification of the device based on dosing information. Further, currently described systems may not provide social interaction with other users.

For example with regard to dosing, previous attempts to determine the dosage of vapor and/or an active ingredient in the vapor have been unsatisfactory. Systems that pre-determine dosage by restricting the amount of material to be delivered in a session assume, often incorrectly, that all of the material will be inhaled, and may not be adjustable for partial dosages. Such systems may also meter the amount of material, and require accurate measurement of the mass and/or volume of material being delivered for vaporization, or measure the difference between a starting mass/volume and post-delivery mass or volume. These measurements may be difficult, requiring a high level of accuracy and expense, and may result in inaccurate results. Further, current dose controlling electronic smoking devices typically control the dose delivered without a link to or actual knowledge of the actual clinical and medical needs of the user, and may not allow a controlled dose to be adjusted based on the user biometrics such as weight, age, symptoms, etc. Existing systems may also lack features that allow a user to customize usage based on their habits and goals, as well as their social needs.

The systems, apparatuses, and methods described herein address at least these problems and concerns.

SUMMARY

Aspects of the current subject matter relate to management of operation (e.g. one or more settings or operation parameters of a vaporizer. In some aspects, a cartridge may be coupled to a vaporizer body. The cartridge may include a vaporizable material and a heater as well as an identifier, which may optionally be a cartridge memory. The vaporizer body may include a controller, which may exchange data (e.g. via one or two way communication) with the identifier. This exchange of data may optionally occur via a same circuit over which electrical power from a power source of the vaporizer body is delivered to the heater of the cartridge.

In another aspect, a vaporizer system can include a device in communication with a vaporizer. The device may execute software or other instructions that result in an application usable to obtain information from a vaporizer, optionally over a wireless communication channel. In addition, the application may relay commends to a controller of the vaporizer to affect one or more operations of the vaporizer.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to electronic vaporizer devices, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 1A illustrates features of an exemplary vaporizer consistent with implementations of the current subject matter;

FIGS. 1B, 1C, 1D and 1E illustrate features of example variations of a vaporizer and cartridge assembly consistent with implementations of the current subject matter;

FIGS. 7A-7B illustrate features of exemplary user interfaces for an application that may be used with a vaporizer consistent with implementations of the current subject matter;

FIGS. 18A-18E illustrate features of exemplary user interfaces that may be used to guide a user through operation of a vaporizer and/or an associated application consistent with implementations of the current subject matter;

FIGS. 27A-27D illustrate features of an exemplary user interface that may be used to learn about various cartridges consistent with implementations of the current subject matter;

When practical, similar reference numbers denote similar structures, features, or elements.

DETAILED DESCRIPTION

Figure 1E:
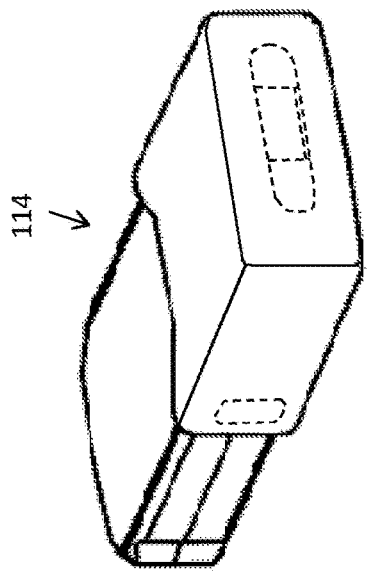

Implementations of the current subject matter includes methods, apparatuses, articles of manufacture, and systems relating to vaporizing of one or more materials for inhalation by a user. Example implementations include vaporizer devices and systems including vaporizer devices. The term "vaporizer" is used generically in the following description and claims to refer to any of a self-contained apparatus, an apparatus that includes two or more separable parts (e.g. a vaporizer body that includes a battery and other hardware and a cartridge that includes a vaporizable material). A "vaporizer system" as used in this document may include one or more components, such as a device in communication (e.g. wirelessly or over a wired connection) with a vaporizer and optionally also the vaporizer itself. A vaporizer or one or more components of a vaporizer system consistent with implementations of the current subject matter may be configured for user control and operation.

Examples of vaporizers consistent with implementations of the current subject matter include electronic vaporizers, electronic cigarettes, e-cigarettes, or the like. In general, such vaporizers are hand-held devices that heat (by convection, conduction, radiation, or some combination thereof) a vaporizable material to provide an inhalable dose of the material. The vaporizable material used with a vaporizer may be provided within a cartridge (e.g. a part of the vaporizer that contains the vaporizable material in a reservoir or other container and that can be refillable when empty or disposable in favor a new cartridge containing additional vaporizable material of a same or different type. A vaporizer may be a cartridge-using vaporizer, a cartridge-less vaporizer, or a multi-use vaporizer capable of use with or without a cartridge. For example, a multi-use vaporizer may include a heating chamber (e.g. an oven) configured to receive a vaporizable material directly in the heating chamber and also to receive a cartridge having a reservoir or the like for holding the vaporizable material. In various implementations, a vaporizer may be configured for use with liquid vaporizable material (e.g., a carrier solution in which an active and/or inactive ingredient(s) are suspended or held in solution or a liquid form of the vaporizable material itself) or a solid vaporizable material. A solid vaporizable material may include a plant material that emits some part of the plant material as the vaporizable material (e.g. such that some part of the plant material remains as waste after the vaporizable material is emitted for inhalation by a user) or optionally can be a solid form of the vaporizable material itself such that all of the solid material can eventually be vaporized for inhalation. A liquid vaporizable material can likewise be capable of being completely vaporized or can include some part of the liquid material that remains after all of the material suitable for inhalation has been consumed.

Consistent with some implementations of the current subject matter, a vaporizer and/or vaporizer system may be configured to identify a vaporizable material to be vaporized, and to adjust the operation of the vaporizer accordingly. For example, a vaporizer may be adapted to receive a cartridge or other pre-loaded container holding a vaporizable material (e.g., the vaporizable material a solution of nicotine, cannabis, and/or another active ingredient) and to identify and/or determine information about the vaporizable material and/or the cartridge or other pre-loaded container, such as one or more of: a type of vaporizable material, a concentration of vaporizable material in a solution or other non-pure form of a vaporizable material that is contained in a reservoir or other container of the cartridge, an amount (e.g. a mass, volume, etc.) of vaporizable material in a reservoir or other container of the cartridge, a configuration of the cartridge (e.g., what specific components or types of components such as a heater power or configuration, one or more electrical properties, etc. are present in the cartridge), a lot number of the cartridge, a date of manufacture of the cartridge, an expiration date after which the cartridge should not be used, a manufacture or fill date for the cartridge, or the like.

A vaporizer consistent with implementations of the current subject matter may be configured to connect (e.g., wirelessly connect or over a wired connection) to a communication device (or optionally devices) in communication with the vaporizer. Such a device can be a component of a vaporizer system as discussed above, and can include first communication hardware, which can establish a wireless communication channel with second communication hardware of the vaporizer. For example, a device used as part of a vaporizer system may include a general purpose computing device (e.g. a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g. configurable on a screen or other display device and selectable via user interaction with a touch-sensitive screen or some other input device like a mouse, pointer, trackball, cursor buttons, or the like) interface controls.

A device that is part of a vaporizer system as defined above can be used for any of one or more functions, such as controlling dosing (e.g. dose monitoring, dose setting, dose limiting, user tracking, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g. games, social media communications, interacting with one or more groups, etc.) with other users, or the like.

In some implementations of the current subject matter, a vaporizer can include functionality for communicating with a cartridge containing a vaporizable material. The vaporizer may also be in communication with a device that is part of a vaporizer system, although this is not required. The vaporizer, whether under control of or otherwise in communication with a device that is part of a vaporizer system or as a standalone unit separate from a vaporizer system can be configured such that operation of the vaporizer can be modified, controlled, etc. based on one or more parameters that are received from the cartridge or are accessed from a database or other information source based on the identification of the cartridge.

For example, a vaporizer consistent with implementations of the current subject matter can be configured to recognize a cartridge and recite (and in some cases transmit) or otherwise acquire information about the cartridge. In other words, a computing element such as a controller or the like that is associated with a vaporizer body can obtain information about the cartridge via some form of data exchange. A variety of methods of cartridge recognition by a vaporizer are within the scope of the current subject matter, including those described in more detail below. Any of the approaches described herein may be performed with or without the addition of wireless communication/connectivity also described herein, although such wireless connectivity as described herein may be advantageously applied, as will be described in greater detail below.

Implementations of the current subject matter also include methods of using a vaporizer and/or a vaporizer system for functions such as determining and/or controlling a dose, amount, or the like of one or more chemical species of the vaporizable material or of the vaporizable material itself.

FIGS. 1A-2C illustrate example features that may be included in vaporizers 100, 200 consistent with implementations of the current subject matter. FIG. 1A shows a schematic view of a vaporizer 100 that uses a cartridge, and FIGS. 1B-1E show views of an exemplary vaporizer 100 with vaporizer body 101 and cartridge 114. FIGS. 1B and 1C show top views before and after connecting a cartridge 114 to a vaporizer body 101. FIG. 1D is a perspective view of the vaporizer 100, which includes a vaporizer body 101 combined with a cartridge 114, and FIG. 1E shows a perspective view of one variation of a cartridge 114 holding a liquid vaporizable material. In general, when a vaporizer includes a cartridge (such as the cartridge 114), the cartridge 114 may include one or more reservoirs 120 of vaporizable material. Any appropriate vaporizable material may be contained within the reservoir 120 of the cartridge 114, including solutions of nicotine or other organic materials.

As noted above, the vaporizer 100 shown in FIG. 1 includes a vaporizer body 101. As shown in FIG. 1, a vaporizer body 101 consistent with implementations of the current subject matter may include a housing enclosing a power source 103 (e.g. a device or system that stores electrical energy for on-demand use), which may be a battery, capacitor, a combination thereof, or the like, and which may be rechargeable or non-rechargeable. The housing may also enclose a controller 105, which may include a processor. In the examples shown, a cartridge 114 may be attached on, in, or partially in the vaporizer body 101.

A processor of the controller 105 may include circuitry to control operation of a heater 118, which can optionally include one or more heating elements for vaporizing a vaporizable material contained within the cartridge 114, for example within a reservoir or container that is part of the cartridge 114. In various implementations, the heater 118 may be present in the vaporizer body 101 or within the cartridge 114 (as shown in FIG. 1A), or both. The controller circuitry may include one or more clocks (oscillators), charging circuitry, I/O controllers, memory, etc. Alternatively or in addition, the controller circuitry may include circuitry for one or more wireless communication modes, including Bluetooth, near-field communication (NFC), WiFi, ultrasound, ZigBee, RFID, etc. The vaporizer body 101 may also include a memory 125 that may be part of the controller 105 or otherwise in data communication with the controller. The memory 125 may include volatile (e.g. random access memory) and/or non-volatile (e.g. read-only memory, flash memory, solid state storage, a hard drive, other magnetic storage, etc.) memory or data storage.

Further with reference to FIG. 1, a vaporizer 100 may include a charger 133 (and charging circuitry which may be controlled by the controller 105), optionally including an inductive charger and/or a plug-in charger. For example, a universal serial bus (USB) connection may be used to charge the vaporizer 100 and/or to allow communication over a wired connection between a computing device and the controller 105. The charger 133 may charge the onboard power source 103. A vaporizer 100 consistent with implementations of the current subject matter may also include one or more inputs 117, such as buttons, dials, or the like, and/or sensors 137, including accelerometers or other motion sensors, capacitive sensors, flow sensors, or the like. These sensors 137 may be used by the vaporizer 100 to detect user handling and interaction. For example, detection of a rapid movement (such as a shaking motion) of the vaporizer 100 may be interpreted by the controller 105 (e.g. through receipt of a signal from one or more of the sensors 137) as a user command to begin communication with a user device that is part of a vaporizer system and that can be used for controlling one or more operations and/or parameters of the vaporizer 100 as described in more detail below. Additionally or alternatively, detection of a rapid movement (such as a shaking motion) of the vaporizer 100 may be interpreted by the controller 105 (e.g. through receipt of a signal from one or more of the sensors 137) as a user command to cycle through a plurality of temperature settings to which the vaporizable material held within the cartridge 114 is to be heated by action of the heater 118. In some optional variations, detection of removal of the cartridge 114 by the controller 105 (e.g. through receipt of a signal from one or more of the sensors 137) during a cycling-through of the plurality of temperature settings may act to establish the temperature (e.g., when the cycle is at a desired temperature, a user may remove the cartridge 114 to set the desired temperature). The cartridge 114 may then be re-engaged with the vaporizer body 101 by the user to allow use of the vaporizer 100 with the heater controlled by the controller 105 consistent with the selected temperature setting. The plurality of temperature settings may be indicated through one or more indicators on the vaporizer body 101.

A vaporizer consistent with implementations of the current subject matter may also include one or more outputs 115. Outputs 115 as used herein can refer to any of optical (e.g., LEDs, displays, etc.), tactile (e.g., vibrational, etc.), or sonic (e.g., piezoelectric, etc.) feedback components, or the like, or some combination thereof.

A vaporizer 100 consistent with implementations of the current subject that includes a cartridge 114 may include one or more electrical contacts (such as the electrical contacts 109, 111, 113 shown in FIG. 1A) on or within the vaporizer body 101 that may engage complementary contacts 119, 121, 123 (e.g., pins or receptacles) on the cartridge 114 when the cartridge is engaged with the vaporizer body 101. The contacts on the vaporizer body are generally referred to as "vaporizer body contacts" and those on the cartridge are generally referred to as "cartridge contacts." These contacts may be used to provide energy from the power source 103 to the heater 118 in implementations of the current subject matter in which the heater 118 is included in the cartridge 114. For example, when the cartridge contacts and the vaporizer body contacts are respectively engaged by coupling of the cartridge 114 with the vaporizer body 101, an electrical power circuit can be formed allowing control of power flow from the power source 103 in the vaporizer body 101 to the heater 118 in the cartridge 114. A controller 105 in the vaporizer body 101 can regulate this power flow to control a temperature at which the heater 118 heats a vaporizable material contained in the cartridge 114.

Any appropriate electrical contact may be used, including pins (e.g., pogo pins), plates, and the like. In addition, as described below, in some implementations of the current subject matter one-way or two-way communication is provided between the vaporizer body 101 and the cartridge 114 through one or more electrical contacts, which may include the electrical contacts used to provide energy from the power source 103 to the heater 118. The cartridge 114 and the vaporizer body 101 may be removably coupled together, e.g., by engaging a portion of a housing of the cartridge 114 with the vaporizer body 101 and/or the vaporizer housing in a mechanical connection (e.g., a snap and/or friction fit) or the like. Alternatively or additionally, the cartridge 114 and the vaporizer body 101 may be coupled magnetically or via some other coupling or engaging mechanism.

Any of the cartridges described herein may include one or more identifiers 138. The identifier 138 may be recognized, detected, and/or read by the vaporizer body 101, and may convey information about the vaporizable material contained within the cartridge and/or about the cartridge 114 itself. The identifier 138 may include a readable and/or readable/writable cartridge memory. The identifier 138 may include circuitry for receiving and/or transmitting information between the cartridge 114 and the vaporizer body 101. For example, a data exchange circuit may include the cartridge memory, which stores information (e.g. data characterizing one or more parameters of the cartridge), and additional circuitry that forms a data exchange circuit in cooperation with other circuitry on a vaporizer body 101 when the cartridge 114 is coupled to the vaporizer body 101. Examples of this data exchange circuit are described below, for example in reference to FIG. 6A.

In some implementations of the current subject matter, the identifier 138 is passive and may include codes or markings (e.g., bar codes, quick response (QR) codes, etc.). In some examples, the identifier 138 may be structural (e.g., one or more pins, projections, etc.) on the cartridge 114 that may be detected by the vaporizer body 101. Visual or mechanical identifiers may be identified directly by the vaporizer body 101 using an imaging device (e.g., camera, etc.) or reading device (e.g., optical reading) integrated into the vaporizer body (not shown in FIG. 1A), or via communication through a separate device, such as a smartphone. For example, a user may take an image of the identifier 138 (e.g., code, marking, etc.) and transmit the code or information derived from the code (such as the information about the vaporizable material and/or the cartridge) to the vaporizer body 101 via wireless circuitry 107, or optionally over a wired connection. A wireless connection (e.g. a wireless communication channel) can be established between first communication hardware of the device and second communication hardware of the vaporizer. The first and second communication hardware can respectively include transceivers for use with one or more wireless communication protocols, non-limiting examples of which are described below.

Figure 1D:
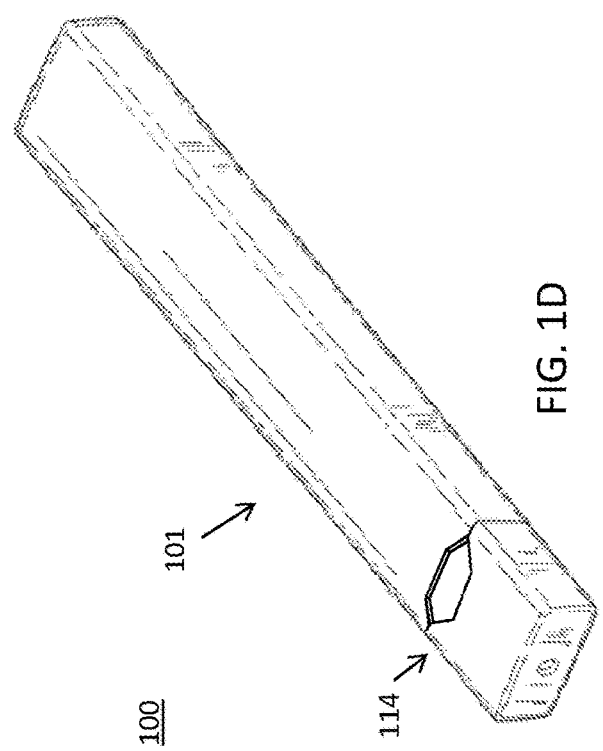

FIGS. 1B to 1E illustrate an example of a vaporizer 100 with a vaporizer body 101 and cartridge 114. The two are shown unconnected in FIG. 1B and connected in FIG. 1C. FIG. 1D shows a perspective view of the combined vaporizer body 101 and cartridge 114, and FIG. 1E shows an individual cartridge 114. FIGS. 1B-1E an example including many of the features generally shown in FIG. 1A. Other configurations, including some or all of the features described herein, are also within the scope of the current subject matter.

Figure 2A:
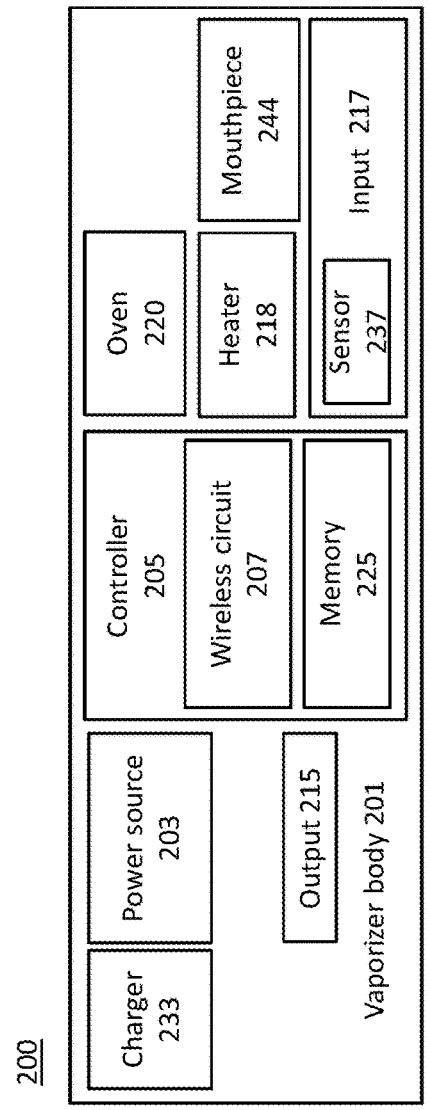
FIG. 2A illustrates features of an example of a vaporizer that may be used consistent with implementations of the current subject matter.

FIG. 2A shows a schematic diagram of a vaporizer 200 that does not use a cartridge (but may still optionally accept a cartridge), but may instead use a loose-leaf material. The vaporizer 200 in FIG. 2A may include loose vaporizable material that may be placed in an oven 220 (e.g., vaporization chamber). Many of the same elements present in the vaporizer 100 using cartridge 114 shown in FIG. 1A-1E may also be included as part of a vaporizer 200 that does not use cartridges. For example, a cartridge-free vaporizer 200 may include a vaporizer body 201 with control circuitry 205 which may include power control circuitry, and/or wireless circuitry 207, and/or memory 225. A power source 203 (e.g., battery, capacitor, etc.) may be charged by a charger 233 (and may include charging control circuitry, not shown). The vaporizer 200 may also include one or more outputs 215 and one or more inputs 217 with sensors 237. In addition, the vaporizer 200 may include one or more heaters 218 that heat an oven 220 or other heating chamber. The heater 218 may be controlled using the resistance of the heater 218 to determine the temperature of the heater, e.g., by using the temperature coefficient of resistivity for the heater. A mouthpiece 244 may also be included.

Figure 2C:
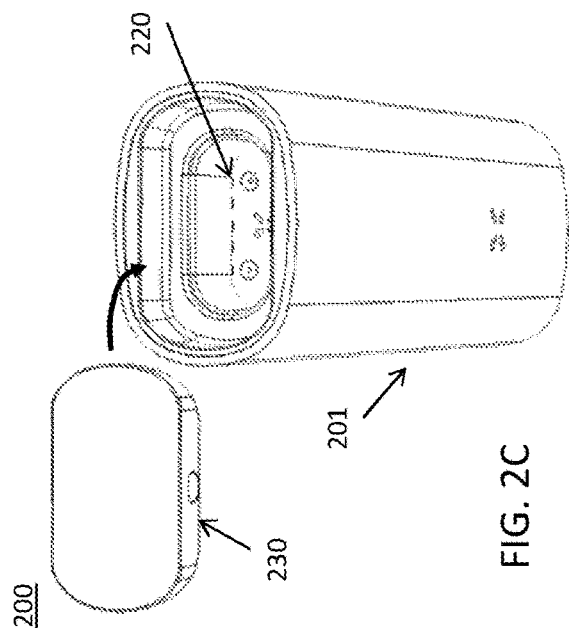
FIGS. 2B and 2C illustrate, via side perspective and bottom perspective views, respectively, features of an example of a vaporizer device consistent with implementations of the current subject matter.
Figure 2B:
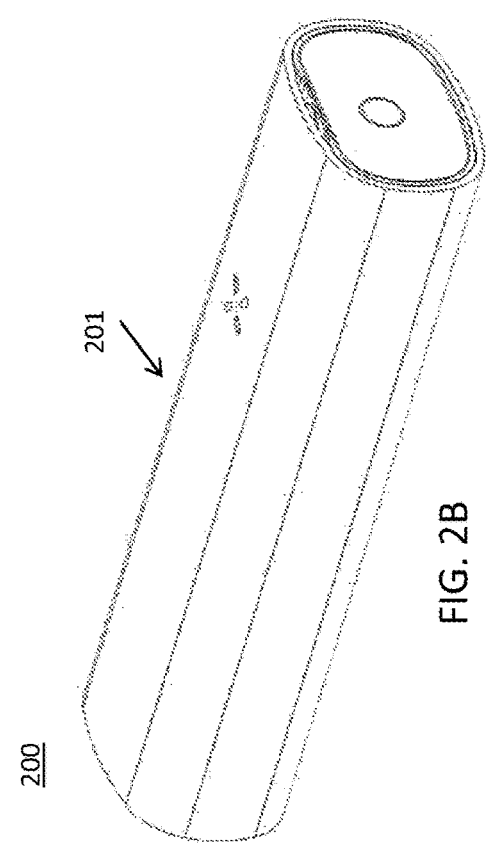

FIG. 2B shows a side perspective of an exemplary vaporizer device 200 with a vaporizer body 201. In the bottom perspective view of FIG. 2C, a lid 230 is shown removed from the vaporizer body 201, exposing the oven/vaporization chamber 220.

Figure 3:
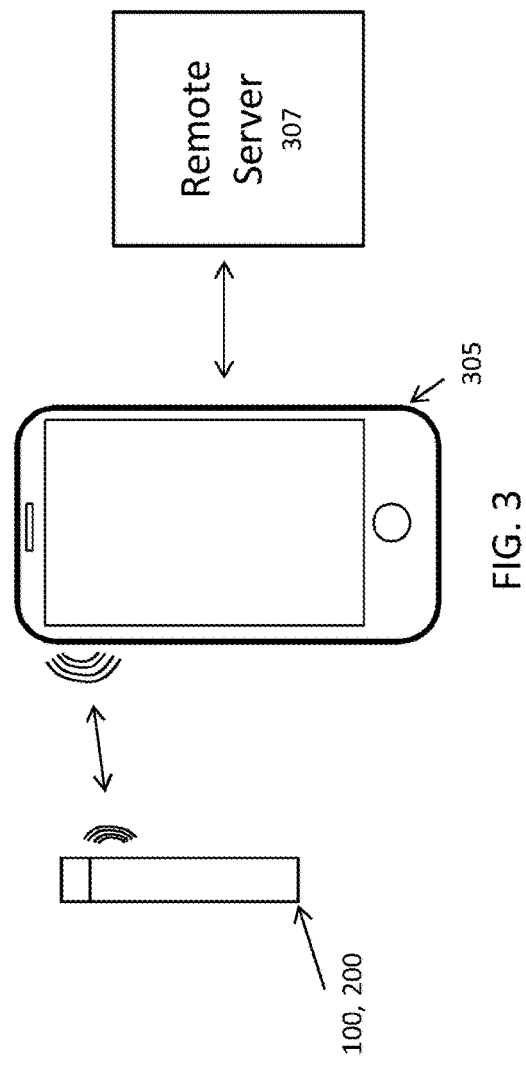
FIG. 3 illustrates communication between a vaporizer, a device, and a server consistent with implementations of the current subject matter.

FIG. 3 shows a schematic representation of communication between a vaporizer 100, 200, a digital device 305 that wirelessly communicates with the vaporizer 100, 200, and a remote server 307 that may communicate directly with the vaporizer 100, 200 or through the digital device 305. The digital device 305 may be a hand-held mobile device such as a smartphone, smartwatch, tablet, etc., or a desktop or laptop computing device. As noted above, the digital device 305 may optionally be a dedicated remote control device.

In general, as illustrated schematically in FIG. 3, any of the vaporizer apparatuses described herein (such as the vaporizer 100 or 200) may remotely communicate with a remote server 307 and/or a digital device 305 such as a wearable electronics device (e.g., Google Glass, smartwatch, smartwear, etc.) and/or a smartphone, smartwatch, etc. Thus, any of these vaporizers 100, 200 may include a communications interface (wireless circuitry 107, 207) that may be implemented through a communication chip (e.g. second communication hardware) in or on the vaporizer 100, 200. Exemplary wireless chips may include, but are not limited to, a Bluetooth chip, such as Parani BCD 210 or Texas Instruments (TI) CC2650 Bluetooth Single-Chip Solution, an NFC-enabled chip (such as Qualcomm's QCA1990), that allows for NFC communication, or enhanced Wi-Fi or Bluetooth communication where NFC is used for link setup. As will be described in detail below, one or more of these wireless circuits may be used for communication with or between the cartridge 114 in embodiments that are configured for reading a cartridge 114 as schematically shown in FIG. 1A. For example, NFC may be used to read an identifier 138 (as RFID tag) on the cartridge 114.

A wireless communication chip may include a Wi-Fi-enabled chip, such as TI's SimpleLink family's CC3000, that can hook the apparatus to Wi-Fi networks. In some embodiments, the wireless circuit comprises a subscriber identity module (SIM) card on board of the vaporizer, a Nano-SIM card, or the like (e.g., allowing 3G/4G cellular network communication). Alternative forms of communication may be used to establish two-way communication between a vaporizer 100, 200 and a user device 305.

Connection between the vaporizer 100, 200 and the user device 305 may be automatic (after an initial set-up) or may be initiated by the user through various settings or may be initiated by shaking the vaporizer 100, 200.

As mentioned above, any of the vaporizer apparatuses described herein that include a cartridge may be configured to recognize and/or identify the cartridge. One or more recognition/identification approaches may be used. The vaporizer may determine information about the cartridge and/or the vaporizable material held in the cartridge, such as one or more of: the type of vaporizable material (e.g., nicotine, cannabis, etc.), the concentration of vaporizable material, the amount of vaporizable material, the configuration of the cartridge (e.g., heater, electrical properties, etc.), the lot number of the cartridge, the date of manufacture of the cartridge, expiration date, etc. This information may be directly encoded on the cartridge or a reference indicator may be provided that the vaporizer (or a processor in communication with the vaporizer) may use as an index to look up some or all of this information, or a combination of reference number and directly encoded material may be provided.

In some implementations of the current subject matter, the cartridge may be recognized and/or identified by the engagement between the cartridge and the vaporizer. The cartridge may be configured to include a keyed interaction with the vaporizer. For example, the shape of cartridge may be detected by the vaporizer. For example, the cartridge may include n pins or protrusions. These pins can be detected by the vaporizer when the cartridge is inserted (e.g., by completing an electrical connection); for n pins, there are $2^n$ possible combinations of markings.

The cartridge may be configured or identified based on an electrical property that the vaporizer can detect based on an electrical connection with the cartridge. For example, the vaporizer may make electrical contact through two or more electrical contacts with the heater and/or additional electrical contacts and may detect a characteristic resistance, inductance, or time response (e.g., time constant, RC time constant, LC circuit resonance, etc.).

In some implementations of the current subject matter, the cartridge may be recognized and/or identified by markings on the cartridge identified by the vaporizer. These markings may be visible or not visible to a user. For example, the cartridge may be marked with a characteristic UV, IR or other wavelength-specific ink that can be detected by the vaporizer, which may include, e.g., an emitter/detector pair specific to the marker(s). For example, markings may include an infrared-scannable barcode located on the cartridge. In some embodiments, the markings may be a pattern, such as a QR code, bar code, etc., that indicate information about the cartridge and/or the contents (vaporizable material) of the cartridge. The markings may be symbolic, including alphanumeric. The markings may be 'read' or detected directly by the vaporizer, which may include a camera or other optical detector, or it may be indirectly detected via communication with a second device (e.g., wearable, smartphone, etc.) having a camera or the like. For example, markings on the cartridge may be detected by a smartphone such as the user device 305; the smartphone may identify the marking using an application (e.g., software) on the smartphone to look up one or more properties from a look-up table, or it may directly communicate the marking to the vaporizer that may look up the properties, and/or it may communicate with a remote server that may look up the properties and communicate them to the vaporizer directly or through the smartphone.

In some implementations of the current subject matter, the cartridge may be recognized by RFID (Radio-Frequency identification) technology. RFID markers have been used in a wide array of applications for inventory control. Some RFID technologies use active devices which contain their own power source and others use passive RFID devices that interact with another powered device that causes the transfer of data without reliance on power at the passive device. For example, a cartridge may include one or more RFID chips or components that can be detected and read by a reader on the vaporizer to identify and receive information about the cartridge.

In some implementations of the current subject matter, the cartridge may be recognized and/or identified by communicating with a memory (e.g., EEPROM) on the cartridge through an electrical connection with the vaporizer. In implementations in which the heater is present on the cartridge, such as the exemplary vaporizer shown in FIG. 1A, it may be advantageous to use one or more of the electrical connections on the cartridge (e.g., contacts 119, 121, 123) that are also used to power and/or control the heater to communicate with the memory. This may be particularly challenging where the cartridge may engage with the vaporizer in more than one orientation, and/or where the heater is controlled through this same contact, and modulation of the applied/received electrical signals between the cartridge and the vaporizer may modify the control and/or temperature determination of the heater. One or more additional electrical contacts may be used in addition to those controlling the heater. In general, communication between the cartridge and the vaporizer may be one way (e.g., reading information about the cartridge and/or the vaporizable material from the cartridge by the vaporizer) or it may be two-way (e.g., reading information about the cartridge and/or the vaporizable material and writing information about the operation of the device, e.g., number of uses, duration of use, temperature settings, etc.). Information may be written to the cartridge, and this information may be used to derive other information about the cartridge, including the amount of material left in the cartridge, etc.

In general, any of the vaporizers described herein may estimate, measure and/or predict the amount of vapor and/or material (including active ingredients) in the vapor that can be delivered to a user. For example, as described in detail below, the apparatuses described herein may be used to determine and/or control dosing of the vaporizable material. For example, the current subject matter includes vaporizers and methods of using such vaporizers for accurate and controlled dose delivery of an active ingredient in a vaporizable material (e.g., nicotine, cannabis, and any other active ingredient/drug) based on user specified, medical, switching or cessation needs. Dose control may include display of dosing information per use, per session (multiple uses within a predetermined time period, such as 1-15 minutes, 1-30 min, within 1-60 min, 1-90 min, 1-120 min, etc.), per day, or other predetermined and/or user-defined time period. Dose control may also include monitoring dosing (e.g., amount of one or more active ingredient delivered by the apparatus). Dosing control may also or alternatively include controlling the operation of the vaporizer based on the amount of one or more active ingredient delivered by the apparatus over time, including alerting a user when a predetermined (user defined, factory-set, or third-party set)

amount or threshold is approached (e.g., within 50%, 75%, 80%, 85%, 90%, 95%, 98%, 99%, etc. of the predetermined amount) or exceeded, and/or stopping (locking, disabling, etc.) operation of the apparatus when the predetermined threshold is met or exceeded. Apparatuses that include dosing (dose) control may include internal logic (circuitry and/or programming, including application-specific integrated circuit (ASIC) logic) for controlling dosing and/or may communicate with an external processor (via a wireless communication link) that performs all or some of the dose control.

Information about the cartridge and/or a vaporizable material held in the cartridge may be particularly helpful in determining dose. For example information such as one or more of: the type of vaporizable material (e.g., nicotine, cannabis, etc.), the concentration of vaporizable material, the content of the vaporizable material, the amount of vaporizable material, the configuration of the cartridge (e.g., heater, electrical properties, etc.), the lot number of the cartridge, the date of manufacture of the cartridge, expiration date, the thermal properties of the vaporizable material, etc. may be used to accurately estimate dose. In some implementations of the current subject matter, dose and/or use information may be stored (written) on the cartridge (e.g., in a memory).

Vaporizers, vaporizer systems, and methods of using them for user-customization of device settings and drug usage based on activity patterns are also within the scope of the current subject matter. A vaporizers and/or vaporizer system consistent with the current description may allow a user to personalize a vaporizer and engage in social activities.

A vaporizer and/or vaporizer system consistent with implementations of the current subject matter may be configured to facilitate social interaction through the vaporizer. For example, a vaporizer may be configured to share usage information with others, such as third parties, e.g., health care providers, including doctors, etc. for better prescription and administration of medical treatment. A vaporizer and/or vaporizer system may also be configured to communicate with non-medical third parties (e.g., friends, colleagues, etc.), and with unknown third parties (making some or all information publically available). In some embodiments, the vaporizers described herein, either by themselves or in communication with one or more communications devices that are part of a vaporizer system, may identify and provide information about the operation, status or user input from the vaporizer to a public or private network. In some implementations of the current subject matter, a vaporizer and/or vaporizer system may be configured to provide one or more interactive games for use by the user and/or multiple users of different (or the same) vaporizers, including multi-player games that may be used with multiple different vaporizers. Games may be tied to the operation of the vaporizer and/or a user's manipulation of the vaporizer (e.g., based on accelerometer output, touch or lip sensing, draw detection, etc.).

A vaporizer and/or vaporizer system consistent with implementations of the current subject matter may also be configured to provide location information, possibly including one or more of information about user location in proximity to one or more of: other users (known or unknown users, specified or unspecified users, etc.), retailers, specific locations (lounges, clubs, vaporizer-friendly locations), etc. A vaporizer and/or vaporizer system may also be configured to facilitate the placing of orders based on use or operation of the vaporizer and/or vaporizer system.

A vaporizer may include a GPS capability or may access GPS information from another device in communication with the vaporizer as part of a vaporizer system.

As will be described herein in greater detail, a vaporizer may be connected to (e.g. in communication with) an additional (e.g., portable, wearable, smartphone, desktop, laptop, etc.) device, which may enable user programmable dose control, real-time usage monitoring, personalized use settings, device lockout and social features. For example, a vaporizer and/or vaporizer system may include features relating to security controls, including parental control, user age control/restriction and anti-theft control. A vaporizer and/or vaporizer system may include anti-theft and/or authentication functions that may lock or otherwise restrict use/operation of the device when stolen and/or when used with counterfeit parts, and may also be configured to allow locking (e.g., parental-lock) for child-proofing, or otherwise preventing unauthorized third party operation. An anti-counterfeiting or other lock-out feature of this type may be implemented using cartridge identifiers. For example, cartridge identifiers from a verified source or supplier can include a hash or some other verification code as part of the identifier, and the vaporizer may lock out use of the vaporizer if a cartridge lacking the necessary hash or verification code is coupled to a vaporizer body. Such a feature can be used to require that a user identity verification is entered at the device in communication with the vaporizer to cause the device to unlock use of the vaporizer. In one example, a cartridge may include an identifier that indicates that it contains a controlled substance and a user may be required by the application on the device (in response to determining this about the cartridge via identifier information received from the cartridge) to verify his or her identity (e.g. via a password entry, a biometric identity verification, etc.) and for the application to verify that the identified user is authorized for use of the controlled substance prior to being able to use the vaporizer with tat cartridge coupled to the vaporizer body. In another example, a nicotine or cannabis-containing cartridge may require user identity verification such that the application on the device only allows use of the vaporizer is a user identity is verified and the user has been registered as being above the minimum age.

In some examples, a security control may be incorporated via an application executing on a device in communication with a vaporizer. For example, an application executing on a device in communication with a vaporizer can receive an identifier of the vaporizer itself or alternatively/additionally of the cartridge and may, based on or otherwise using the identifier, determine whether a security setting is included in a user profile or other settings associated with the vaporizer or cartridge. Consistent with implementations of the current subject matter, such functionality may be entirely or partially included within the vaporizer (and/or cartridge) or they may be distributed between the vaporizer and a user interface that may be presented on an additional device that is part of a vaporizer system, such as a wearable and/or handheld device, laptop, desktop, etc., operating control logic. Control logic or other software functionality for providing these features may include a user interface, and may provide input/output and analysis capability for modulating operation of the vaporizer. Non-limiting options for the first communication hardware of the device and/or the second communication hardware of the vaporizer are described above.

CARTRIDGE RECOGNITION. In general, a vaporizer may include one or more techniques for cartridge recognition and/or communication, including the use of a marker (e.g., QR code, IR or US marker, etc.), mechanical and/or electronic keying, or the like. In particular described herein are methods and apparatuses for electronic cartridge recognition and communication, in which the cartridge may electronically communicate, via one-way or in some embodiments two-way (including duplex or multiplex) transmission of information, between a cartridge and the vaporizer so that information may be received by the vaporizer from the cartridge. This information may include information about the vaporizable material and/or the cartridge, such as one or more of: type of vaporizable material, concentration of vaporizable material, amount of vaporizable material, volume of the vaporizable material, properties of the vaporizable material (e.g., thermal properties, composition, etc.), configuration of the cartridge (e.g., heater, electrical properties, etc.), lot number, date of manufacture, expiration date, identity verification for the cartridge, and the like.

A cartridge including an identification circuit (also referred to herein as a cartridge identification circuit) may be configured to communicate and transfer such information from the cartridge to the vaporizer. The cartridge identification circuit may include a memory (e.g., an EEPROM). In cartridge variations in which the heater (e.g., a resistive heating element such as a resistive coil or wire) is controlled by the application of energy onto one or more (e.g., 2, 3, 4, etc.) heater electrical contacts that communicate with corresponding contacts on the vaporizer, the cartridge identification circuit may communicate with the vaporizer through the same heater electrical contacts, despite the increased complexity and potential for disruption of the heater.

The cartridge identification circuit may also be configured so that the cartridge may be inserted into the vaporizer in multiple orientations without disrupting the cartridge identification circuit operation.

Figure 4:
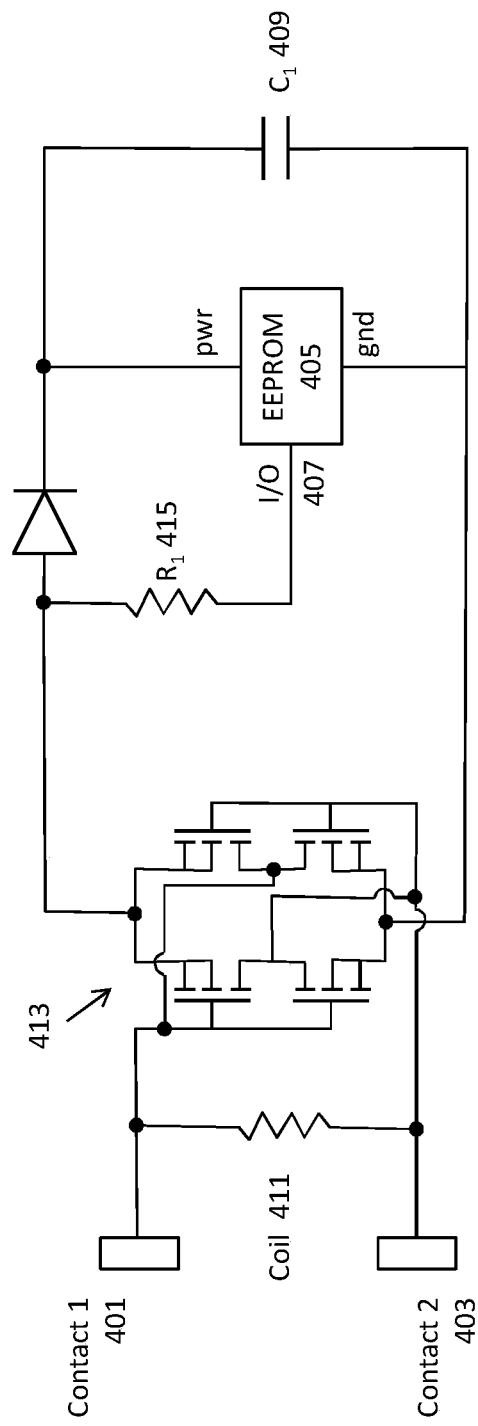
FIG. 4 illustrates features of an exemplary cartridge identification circuit for providing information about a vaporizer cartridge to a vaporizer consistent with implementations of the current subject matter.

FIG. 4 illustrates one example of a cartridge identification circuit that may be used with (and/or in) a vaporizer cartridge, according to embodiments. This embodiment may be used with a cartridge that can connect to a vaporizer in any orientation, and requires only two electrical contacts that are shared with the heating element (coil) in the cartridge. In FIG. 4, the cartridge identification circuit includes a readable memory 405 (e.g., shown here as an electrically erasable programmable read-only memory, or EEPROM which may be readable, read-only or readable/writable. The readable memory 405 in FIG. 4 is a three-pin EEPROM and includes an output (and/or input/output, I/O) 407, and receives power from a conditioning circuit including a capacitive element (capacitor $C_1$ 409) that allows the EEPROM to transmit information back to heater contacts 401, 403 during periods when the heater (e.g., resistive heating coil 411) is not being energized by energy applied to the heater contacts 401, 403.

The cartridge identification circuit in FIG. 4 is configured to operate in any orientation of the cartridge (e.g., the heating electrical contacts 401,403 are reversible), and includes an H-bridge circuit 413. Thus, the three-pin EEPROM (including power, ground, I/O lines) is linked via the capacitive network to the heating electrical contacts 401, 403 and the cartridges does not have to be keyed directionally, but can be instead by inserted in either direction (either polarity) into the vaporizer, plugged in, and powered to operate the heater. The H-bridge circuit 413 shown rectifies the voltage applied so that the EEPROM power and ground receive appropriate input. When a voltage is applied between the electrical heating contacts above gate voltage threshold (e.g., power on) for any of the transistors (e.g., four MOSFETS are shown in FIG. 4) in the H-Bridge circuit 413, the resulting voltage applied to the memory is rectified.

When power is applied to the heating electrical contacts and rectified by the H-bridge circuit 413, the potential passes through the diode to charge up the capacitive circuit (e.g., $C_1$ 409), which allows the memory 405 (e.g., EEPROM or other memory device) to stay powered while receiving signals (write or read requests) on I/O line 407 from the device (e.g., in this example, the device is switching voltage applied to the heating electrical contacts in a serial bit pattern encoding information). After a read is requested from the EEPROM, the EEPROM can transmit information from its memory out onto the I/O line 407, and this can be detected by the vaporizer at the contacts 401, 403 via a resistance measurement circuit that can detect whether or not I/O line 407 is holding $R_1$ 415 in parallel with the resistance of the coil 411; I/O line 407 may be an open-drain output from the memory 405, such that it is held at GND in one logical output state, and allowed to float in the other state. For example, $C_1$ 409 may be approximately 10 nF, which (with an EEPROM with 1 µA ground current) would allow the memory 405 to send data to the device for 10 ms (100 bits out at 10 kbaud) before $C_1$ 409 has discharged by 1 V. In this example, the capacitive circuit allows the vaporizer to write to the memory concurrent with operation of the heater through the same contacts.

In some implementations of the current subject matter, a vaporizer may be configured to both read from and write to the memory, such as when a cartridge identification circuit similar to the one shown in FIG. 4 is used. In this example, the vaporizer may write to the cartridge identification circuit. Specifically the vaporizer apparatus heating controller (e.g., heating control circuit) may be adapted to detect a resistance change between heater contacts 401 and 403 when the output of the memory's (e.g., the EEPROM's) I/O line 407 changes from logical low to high and vice versa, as just described. As mentioned above with reference to FIGS. 1A and 2A, a vaporizer may include a controller that controls the application of energy to the heater from the battery, to heat and therefore vaporize the vaporizable material. Any of these controllers may include a printed circuit board (PCB) and may further comprise: a microcontroller; switches; resistance measurement circuitry comprising a reference resistor or Wheatstone bridge and differential operational amplifier; and an algorithm comprising logic for control parameters. In some embodiments, the controller (e.g., the microcontroller, processor, etc.) cycles the switches at fixed intervals to measure the resistance of the resistive heating element relative to the reference resistor, and applies the algorithm control parameters to control the temperature of the resistive heating element. This same circuitry controlling the heater may be adapted to read and/or modify the memory in a cartridge connected through the heater electrical contracts.

Figure 6A:
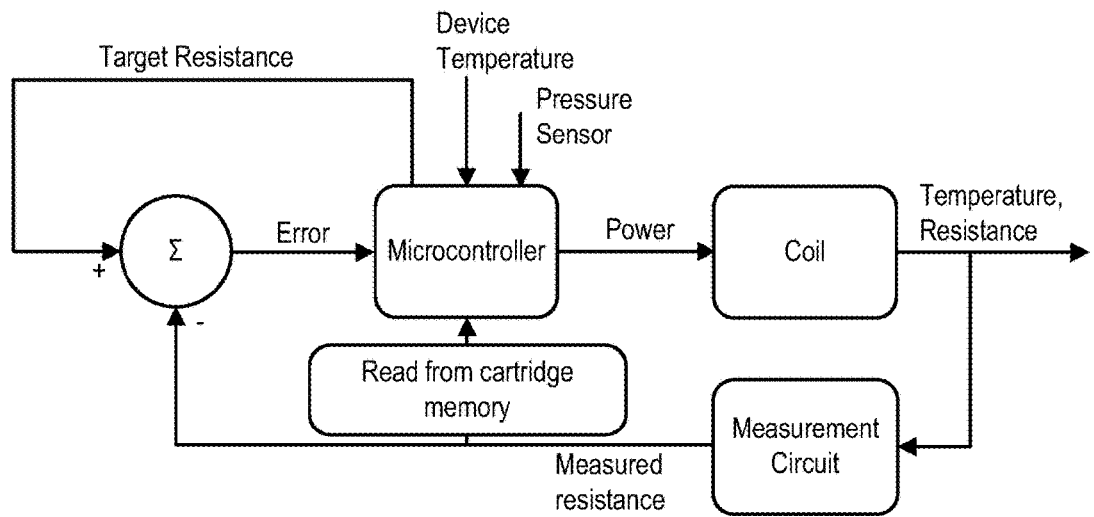
FIG. 6A illustrates features of an integral-derivative controller or PID controller for a vaporizer that may be adapted for detection of a cartridge using a cartridge identification circuit consistent with implementations of the current subject matter.

As illustrated in the block diagram of FIG. 6A, the vaporizer may utilize a proportional-integral-derivative controller or proportional-integral-derivative (PID) controller programmed to follow a particular PID control law algorithm. A PID controller calculates an "error" value as the difference between a measured process variable and a desired SetPoint. When PID control is enabled, power to the coil is monitored to determine whether or not acceptable vaporization is occurring. With a given airflow over the coil, more power will be required to hold the coil at a given temperature if the device is producing vapor (heat is removed from the coil to form vapor). If power required to keep the coil at the set temperature drops below a threshold, the device indicates that it cannot currently produce vapor.

Under normal operating conditions, this indicates that there is not enough liquid in the wick for normal vaporization to occur.

In parallel with such a PID controller, the vaporizer controller may also monitor changes in the load of the heater contacts (electrodes) to read from the cartridge memory to identify the cartridge and receive information from the cartridge, as described above.

The printed circuit board may therefore further include logic capable of detecting a signal (change in resistance) on the heater contacts when the memory is outputting information stored in the memory. When the microcontroller is running the PID control law algorithm, in addition to detecting the difference between a set point and the coil temperature (error) to control power to the coil so that the coil reaches the set point temperature, (e.g., between 200° C. and 400° C.), the microcontroller may also decode a digital signal sent along the heater contracts from the cartridge, where the received signal includes information about the cartridge and/or the vaporizable material within the cartridge.

Figure 6B:
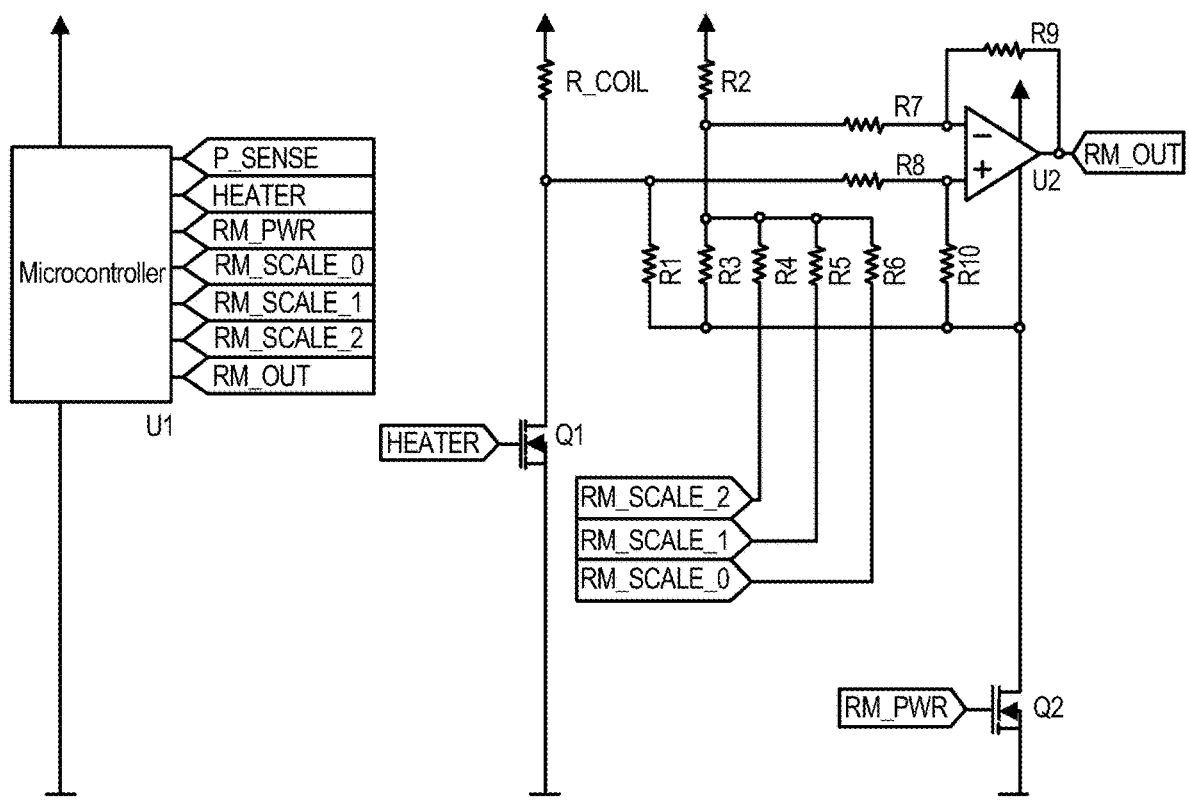
FIG. 6B illustrates features of a variation of a resistance measurement (or comparison) circuit that may be adapted for detection of a cartridge using a cartridge identification circuit consistent with implementations of the current subject matter.

The components of the device used to control the resistive heating element coil temperature are further illustrated in the circuit diagram of FIG. 6B. A battery or other power source may power the microcontroller (MCU). The microcontroller may turn on power to the heater for a predetermined time period (e.g., for 1 ms every 100 ms) so that the voltage between a reference voltage (e.g., $R_{ref}$ or $R_2$) and R_COIL may be measured by the MCU. When Q2 is off, the control law controls Q1 with PWM (pulse width modulation) to power the coil (battery discharges through Q1 and R_COIL when Q1 is on). A signal applied by the memory at the heater electrode contacts by the memory may be detected as a change in the $R_{coil}$. In some embodiments of the device, the device body further comprises at least one: second heater contact; a power switch; a pressure sensor; and an indicator light.

In general, the resistance of the heating element (which is the resistance between the contacts (e.g., resistance between contact 1 401 and contact 2 403 in FIG. 4) may be an input to the microcontroller. In some cases, the resistance may be determined by the microcontroller based on a measurement from a circuit with a resistor with at least one known resistance, for example, a Wheatstone bridge. Alternatively, the resistance of the heating element may be measured with a resistive voltage divider in contact with the heating element and a resistor with a known and substantially constant resistance. The measurement of the resistance of the heating element may be amplified by an amplifier. The amplifier may be an op amp or instrumentation amplifier. The amplified signal may be substantially free of noise. In some cases, a charge time for a voltage divider between the heating element and a capacitor may be determined to calculate the resistance of the heating element. In some cases, the microcontroller may deactivate the heating element during resistance measurements. The resistance of the heating element may be a function of the temperature of the heating element such that the temperature may be directly determined from resistance measurements. The output of the memory (digital signal output) may also be determined from these resistance measurements. Determining the temperature directly from the heating element resistance measurement rather than from an additional temperature sensor may generate a more accurate measurement because unknown contact thermal resistance between the temperature sensor and the heating element is eliminated. In addition, determining the output of the memory based on the small changes (e.g., detectable using the Wheatstone bridge in circuitry in the vaporizer) may be performed without compromising the control of the heater as based on the change in thermal resistivity. The temperature measurement may be determined directly while ignoring the effect of the output of the memory; separately or in parallel this output may be digitally decoded by the microprocessor.

The PID control block diagram shown in FIG. 6A is an example of a resistance measurement circuit used in this PID control scheme. In FIG. 6A, the block diagram includes a measurement circuit that can measure the resistance of the resistive heater (e.g., coil) and provide an analog signal to the microcontroller, a device temperature, which can be measured directly by the microcontroller and/or input into the microcontroller, and an input from a sensor (e.g., a pressure sensor, a button, or any other sensor) that may be used by the microcontroller to determine when the resistive heart should be heated, e.g., when the user is drawing on the device or when the device is scheduled to be set at a warmer temperature (e.g., a standby temperature). The measurement circuit may also decode the change in the measured electrical property (e.g., resistance) at the heater electrical contacts to determine the cartridge information.

In FIG. 6A, a signal from the measurement circuit goes directly to the microcontroller and to a summing block. In the measurement circuit, an example of which is shown in FIG. 6B, signals from the measurement circuit are fed directly to the microcontroller. The summing block in FIG. 6A is representative of the function which may be performed by the microcontroller when the device is heating; the summing block may show that error (e.g., in this case, a target resistance minus a measured resistance of the resistive heater) is used by a control algorithm to calculate the power to be applied to the coil until the next coil measurement is taken.

In the example shown, signal from the measurement circuit may also go directly to the microcontroller. The resistive heater may be used to determine a baseline resistance (also referred to herein as the resistance of the resistive hater at an ambient temperature), when the device has not been heating the resistive heater, e.g., when some time has passed since the device was last heating. Alternatively or additionally, the baseline resistance may be determined by determining when coil resistance is changing with time at a rate that is below some stability threshold. Thus, resistance measurements of the coil may be used to determine a baseline resistance for the coil at ambient temperature.

A known baseline resistance may be used to calculate a target resistance that correlates to a target rise in coil temperature. Similarly, fluctuations in this baseline resistance at the appropriate frequency corresponding to the output of the memory (EEPROM) may be decoded as information from the cartridge memory. The configuration shown in FIG. 6A represents an example of a data exchange circuit consistent with implementations of the current subject matter in which data may be passed between a cartridge memory (e.g. in implementations in which an identifier 138 of the cartridge 114 includes the cartridge memory for storing information about the cartridge 114) and a controller 105 that is part of a vaporizer body 101 to which the cartridge 114 is coupled. Such a data exchange circuit allows for data (e.g. one or more parameters of the cartridge, a vaporizable material contained within the cartridge, etc.) may be passed between the cartridge memory and a controller 105 that is part of the vaporizer body 101.

The example of FIG. 6A provides for both delivery of electrical energy from a power source 103 that is part of the vaporizer body 101 to a heater 118 that is part of the cartridge 114 and exchange of data between an identifier 138 on the cartridge 114 and a controller 105 that is part of the vaporizer body 101 via engagement of just two mating electrical contacts (cartridge contacts) on the cartridge 114 with respective electrical contacts (vaporizer body contacts) on the vaporizer body 101. Other implementations of a data exchange circuit for such data exchange can include the use of dedicated data circuits that are separate from power delivery circuits for passing electrical power from the power source 103 (on the vaporizer body) to the heater 118 (on the cartridge). However, having two separate circuits for data exchange and power delivery can increase complexity of the hardware as more than two sets of mating electrical contacts may be necessary. Implementations of the current subject matter permit use of two mating contacts on the cartridge 114 and vaporizer body 101 respectively for both data exchange and power delivery. It will be understood that the fluctuations in baseline resistance discussed above in reference to FIG. 6A represents one option for combining data exchange and power delivery via a single pair of mating electrical contacts. For example, within the scope of the current subject matter data exchanges may be encoded in a power circuit via fluctuations or modulations of one or more of frequencies, resistances (as noted above), current pulses, voltages, or the like.

The baseline (which may also be referred to as the resistance of the resistive heater at ambient temperature) may also be used to calculate the target resistance. A vaporizer temperature can be used to calculate an absolute target coil temperature as opposed to a target temperature rise. For example, the vaporizer temperature may be used to calculate an absolute target coil temperature for more precise temperature control.

The circuit shown in FIG. 6B is one embodiment of a resistance measurement (or comparison) circuit. As before, in this example, the resistance of the heating element may be a function of the temperature of the heating element (and the output of the cartridge memory in parallel with the heating coil) such that the temperature may be determined from resistance measurements, and the output of the cartridge memory may be detected by analyzing the relatively small changes in resistance within a particular frequency (time) range; these changes may be ignored or filtered out when calculating the temperature. The resistance of the heating element is roughly linear with the temperature of the heating element.

In FIG. 6B, the vaporizer sensing circuit includes a Wheatstone bridge connected to a differential op amp circuit. The measurement circuit is powered when Q2 is held on via the RM_PWR signal from the microcontroller (RM=Resistance Measurement). Q2 may be normally off to save battery life. In general, the apparatuses described herein may stop applying power to the resistive heater to measure the resistance of the resistive heater. In FIG. 6B, when heating, the vaporizer can stop heating periodically (turn Q1 off) to measure coil resistance. One voltage divider in the bridge is between the Coil and R1, the other voltage divider is between R2 and R3 and optionally R4, R5, and R6. R4, R5, and R6 are each connected to open drain outputs from the microcontroller so that the R3 can be in parallel with any combination of R4, R5, and R6 to tune the R2/R3 voltage divider. An algorithm tunes the R2/R3 voltage divider via open drain control of RM_SCALE_0, RM_SCALE_1, and RM_SCALE_2 so that the voltage at the R2/R3 divider is just below the voltage of the R_COIL/R1 divider, so that the output of the op amp is between positive battery voltage and ground, which allows small changes in coil resistance to result in measureable changes in the op amp's output voltage. U2, R7, R8, R9, and R10 comprise the differential op amp circuit. As is standard in differential op amp circuits, R9/R7=R10/R8, R9>>R7, and the circuit has a voltage gain, A=R9/R7, such that the op amp outputs HM_OUT=A(V$^+$−V$^-$) when $0 \leq A(V^+ - V^-) \leq V\_BAT$, where V$^+$ is the R_COIL/R1 divider voltage, V$^-$ is the tuned R2/R3 divider voltage, and V_BAT is the positive battery voltage.

In this example, the microcontroller performs an analog to digital conversion to measure HM_OUT, and then based on the values of R1 through R10 and the selected measurement scale, calculates resistance of the coil. When the coil has not been heated for some amount of time (e.g., greater than 10 sec, 20 sec, 30 sec, 1 min, 2 min, 3 min, 4 min, 5 min, 6 min, 7 min, 8 min, 9 min, 10 min, 15 min, 20 min, 30 min, etc.) and/or the resistance of the coil is steady, the microcontroller may save calculated resistance as the baseline resistance for the coil. A target resistance for the coil is calculated by adding a percentage change of baseline resistance to the baseline resistance. When the microcontroller detects via a pressure (or flow) sensor that the user is drawing from the vaporizer, it may output a PWM signal on HEATER to power the coil through Q1. PWM duty cycle can be limited to a max duty cycle that corresponds to a set maximum average power in the coil calculated using battery voltage measurements and coil resistance measurements. This allows for consistent heat-up performance throughout a battery discharge cycle. A PID control algorithm can use the difference between target coil resistance and measured coil resistance to set PWM duty cycle (limited by max duty cycle) to hold measured resistance at target resistance. The PID control algorithm then holds the coil at a controlled temperature regardless of air flow rate and wicking performance to ensure a consistent experience (e.g., vaporization experience, including "flavor") across the full range of use cases and allow for higher power at faster draw rates. In general, the control law may update at any appropriate rate. For example, in some embodiments, the control law updates at 20 Hz. In this example, when heating, PWM control of Q1 is disabled and Q1 is held off for 2 ms every 50 ms to allow for stable coil resistance measurements. In another embodiment, the control law may update at 250-1000 Hz.

In the example shown in FIG. 6B, the number of steps between max and min measureable analog voltage may be controlled by the configuration. For example, precise temperature control (+/−1° C. or better) maybe achieved with a few hundred steps between measured baseline resistance and target resistance. In some implementations of the current subject matter, the number of steps may be approximately 4096. With variations in resistance between cartridges (e.g., +/−10% nominal coil resistance) and potential running changes to nominal cartridge resistance, it may be advantageous to have several narrower measurement scales so that resistance can be measured at higher resolution than could be achieved if one fixed measurement scale had to be wide enough to measure all cartridges that a vaporizer might encounter. For example, R4, R5, and R6 may have values that allow for eight overlapping resistance measurement scales that allow for roughly five times the sensitivity of a single fixed scale covering the same range of resistances that are measurable by eight scales combined. More or less than eight measurement ranges may be used.

In the example shown in FIG. 6B, the measurement circuit may have a total range of 1.31-2.61 Ohm and a sensitivity of roughly 0.3 mOhm, which may allow for temperature setting increments and average coil temperature control to within +/−0.75° C. (e.g., a nominal coil resistance*temperature coefficient of resistance (TCR)=1.5 Ohm*0.00014/° C.=0.21 mOhm/° C., 0.3 mOhm/(0.21 mOhm/° C.)=1.4° C. sensitivity). In some implementations of the current subject matter, R_COIL is 1.5 Ohm nominally, R1=100 Ohm, R2=162 Ohm, R3=10 kOhm, R4=28.7 kOhm, R5=57.6 kOhm, R6=115 kOhm, R7=R9=2 kOhm, R8=R10=698 kOhm. These ranges may also be sufficient to read the output of the memory from the cartridge identity circuit.

As mentioned above, heater resistance is roughly linear with temperature. Changes in heater resistance may be roughly proportional to changes in temperature. With a coil at some resistance, $R_{baseline}$, at some initial temperature, $\Delta T=(R_{coil}/R_{baseline}-1)/TCR$ is a good approximation of coil temperature rise. Using an amplified Wheatstone bridge configuration similar to that shown in FIG. 6B, the vaporizer and/or vaporizer system may calculate target resistance using baseline resistance and a fixed target percentage change in resistance, 4.0%. For coils with TCR of, as an example, 0.00014/° C., this may correspond to a 285° C. temperature rise (e.g., 0.04/(0.00014/° C.)=285° C.).

In general, a vaporizer and/or vaporizer system does not necessarily need to calculate temperature. Instead, these calculations can be done beforehand, and the vaporizer and/or vaporizer system can simply use a target percentage change in resistance to control temperature. For some baseline resistance, coil TCR, and target temperature change, target heater resistance may be: $R_{target}=R_{baseline}(1+TCR*\Delta T)$. Solved for $\Delta T$, this is $\Delta T=(R_{target}/R_{baseline}-1)/TCR$. Some device variations may calculate and provide (e.g., display, transmit, etc.) actual temperature so users can see actual temperatures during heat up or set a temperature in the vaporizer and/or vaporizer system instead of setting a target percentage change in resistance.

Alternatively or additionally, a vaporizer and/or vaporizer system may use measured ambient temperature and a target temperature (e.g., a temperature set point) to calculate a target resistance that corresponds to the target temperature. The target resistance may be determined from a baseline resistance at ambient temperature, coil TCR, target temperature, and ambient temperature. For example, a target heater resistance may be expressed as $R_{target}=R_{baseline}(1+TCR*(T_{set}-T_{amb}))$. Solved for $T_{set}$, this gives: $T_{set}=(R_{target}/R_{baseline}-1)/TCR+T_{amb}$. Some device variations may calculate and provide (e.g., display, transmit, etc.) actual temperature so users can see actual temperatures during heat up or set a temperature in the device instead of setting a target resistance or target percentage change in resistance.

For the voltage divider approach, if $R_{reference}$ is sufficiently close to $R_{baseline}$, temperature change is approximately $\Delta T=(R_{coil}/R_{reference}-R_{baseline}/R_{reference})/TCR$.

As mentioned above, any of the vaporizer and/or vaporizer system variations described herein may be configured to control the temperature only after a sensor indicates that vaporization is required. For example, a pressure sensor (e.g., "puff sensor") may be used to determine when the coil should be heated. This sensor may function as essentially an on off switch for heating under PID control. Additionally, in some embodiments, the sensor may also control baseline resistance determination. For example baseline resistance may be prevented until at least some predetermined time period (e.g., 10 sec, 15 sec, 20 sec, 30 sec, 45 sec, 1 min, 2 min, etc.) after the last puff.

As just described, a vaporizer sensing circuit may be sufficiently precise to detect the change in resistance from the EEPROM I/O output changing state. Thus, this circuit may detect the difference in resistance between (in reference to a cartridge identity circuit such as the one shown in FIG. 4) the $R_1$ resistor (e.g., at approximately 2 KOhms) and a second (e.g., 1 KOhm) resistance.

In the exemplary cartridge identity circuit shown in FIG. 4, only two input contacts (heater electrode contacts 401, 403) are used; additional inputs (contacts) could also be used, which may obviate the need, for example, for the H-Bridge circuit 413, and may allow for other types of memory (including other EEPROM types) to be used. In operation a cartridge with a cartridge identity circuit may be filled, and programmed thereafter to include information about the filling material and/or cartridge. As mentioned above, the information programmed into the memory may include an indication of the type of vaporizable material (e.g., nicotine, cannabis, etc.), the concentration of vaporizable material, the amount of vaporizable material, the configuration of the cartridge (e.g., heater, electrical properties, etc.), properties of the vaporizable material (e.g., thermal properties, viscosity, suggested vaporization temperatures, etc.), the lot number of the cartridge, the date of manufacture of the cartridge, expiration date, usage time to date, energy applied to the cartridge to date, etc. This information may be written digitally in the memory, and may be directly written or may be written as a reference number for which the vaporizer or an additional processor to which the vaporizer may communicate (e.g. a computing device that is part of a vaporizer system) is in communication. The reference number may be used to look up the relevant information.

The same cartridge identity circuit may also be written with information about the cartridge, vaporizable material, and history of the cartridge, including, for example: the usage time and/or total energy applied, etc.

Information stored on the memory (read and/or written) may be encoded, including the use of encryption, error-correction encoding (e.g., hamming code, etc.), or the like. In operation, when the cartridge is first inserted into the vaporizer body, the vaporizer microcontroller may be configured to first determine if a signal can be read off of the cartridge encoding information about the cartridge and/or identifying the cartridge as compatible with the vaporizer. Information may be read using the measurement circuit of the vaporizer. In some embodiments, even when a cartridge may not be read (e.g., may not include a cartridge identity circuit or is unable to read from the cartridge identity circuit) the vaporizer may use a default setting.

During operation, the vaporizer may periodically (e.g., after each puff, etc.) write to the memory in the cartridge identity circuit, if detected. Writing may be performed by the vaporizer by applying power for a predetermined timer period, to power the capacitive circuit, as shown in FIG. 4. The vaporizer microcontroller may then apply a bit pattern on the contacts, by applying a high voltage to one of the contacts at a controlled rate that will be received by the I/O line of the memory 405.

The vaporizer may signal to the memory to request a read from the memory similar to how the device writes to memory, and may then disconnect the battery voltage applied to the heater contacts to allow the memory (e.g., EEPROM) to take control of the I/O line and use it to output data, providing a digital output (switching the I/O line low/high) transmitting an output that the vaporizer detects through the resistance measurement circuit. Typically, if the memory is transmitting, it may affect the absolute accuracy of the temperature control; the vaporizer may be configured so that the device does not heat when the memory is transmitting (outputting) and normal heating operation may not trigger the memory into transmitting data.

Figure 5:
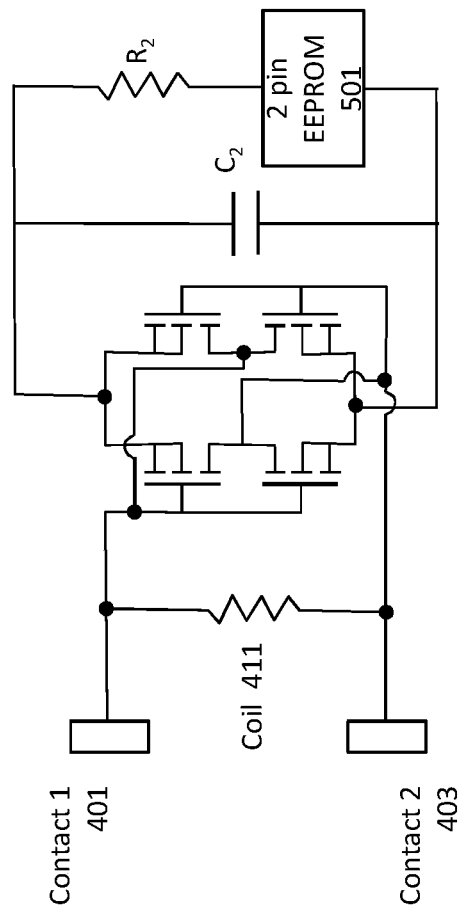
FIG. 5 illustrates features of an additional exemplary cartridge identification circuit consistent with implementations of the current subject matter.

FIG. 5 shows another example of a cartridge identity circuit similar to the one shown in FIG. 4, but with a memory 501 including a two-pin EEPROM. In this case, the cartridge identity circuit is still rectified allowing the cartridge to be connected to the vaporizer in multiple orientations.

A cartridge identity circuit consistent with one or more implementations of the current subject matter may be integrated and/or combined into a custom chip (e.g., ASIC). Such specialized circuit may be included as the identifier (e.g., the identifier 138 shown in FIG. 1A).

Alternatively or additionally, a vaporizer may incorporate a LDS (laser direct structuring) method and resulting structure. In LDS, circuit tracks are integrated here into one or more mechanical components of the vaporizer, such as the housing of a vaporizer and/or a vaporizer body housing, as a substitute for a conventional printed circuit board. As a result, weight and fitting space can be effectively reduced. For example, the three-dimensional circuit carrier may be injection molded from a modified polymer material, allowing laser activation of circuit tracks on the surface of the circuit carrier. A laser may be used to inscribe the circuit layout directly onto the plastic component, typically right after injection molding of the component (without the need for tools or masks). The activated areas may become metallized in a chemical metallization bath in order to build conductive tracks. Other similar process may alternatively or additionally be used, such as molded interconnect device, or MID, formation, in which injection molding and hot stamping are used to integrate conductive structures. Thus, any of the components described herein may comprise an LDS-doped material compatible with the LDS methods for forming the circuitry. In particular, electrical traces for the cartridge (e.g., the identifier 138 embodied as and/or within circuitry) may be formed directly on the plastic parts of the cartridge, without requiring additional PCBs.

As will be described in greater detail below, the information stored in the memory of a cartridge identity circuit such as those described herein may be useful for dose control (e.g., calculating and storing dosing information), as well as for security, communications and storage of operational parameters, particularly in devices including a wireless capability. However, cartridge identification may be useful even in the absence of wireless communication capabilities.

As discussed, the memory (e.g., an EEPROM) may store information about the vaporizable material and/or the cartridge. One example of the information that may be stored may include values related to the specific properties of the heating element, such as the nominal heater R (resistance) for the cartridge, including the heating element of the cartridge. This value may be determined and stored at the factory, at the time the device is manufactured/produced, and/or it may be done later. Storing a specific R value for each cartridge in the memory affiliated with that cartridge may be useful for the accurate temperature control for the device, including determining baseline resistance at ambient temperature, as described above. Although resistance/baseline measurement on the manufacturing line may be slightly different from the measurement the device gets for use, a baseline adjustment (determined by algorithm) may also be used. Alternatively or additionally, once a reliable baseline for a cartridge has been determined, this baseline may be related (e.g., in a remote database, on a remote server, etc.) to an ID affiliated with the specific cartridge, so that if the cartridge is removed and reinserted, the same baseline value can also be used (as soon as the cartridge ID is confirmed) which could be a faster check than waiting for stable baseline to be detected.

In general, storing a cartridge characteristic such as the resistance of the heater in the cartridge itself may be also useful for confirming that the connection between the vaporizer and the cartridge is good, and that the vaporizer's resistance measurement circuit is working normally. Thus, in any of the methods and apparatuses described herein, a nominal cartridge resistance may be stored in the cartridge's memory (or may be stored on a remote server/device and retrieved based on a unique cartridge ID) and may be used to confirm that the connection between the device and pod is good, and/or that the device's resistance measurement circuit is working normally, and/or that the cartridge's resistance has not changed since the cartridge was assembled or filled.

As mentioned above, in some embodiments, the vaporizer may write usage information to the cartridge's memory; usage information can be used to estimate the amount of vaporizable material that has been removed from the cartridge and the amount of vaporizable material remaining. Usage information may include number of puffs/draws, the dosage delivered, or the like.

APPLICATION/CONNECTIVITY. A vaporizer and/or vaporizer system may include software, firmware or hardware that is separate or separable from the vaporizer and that wirelessly communicates with the vaporizer. For example, applications ("apps") may be executed on a processor of a portable and/or wearable device, including smartphones, smartwatches, and the like, which may be referred to as a personal digital device or optionally just a device (e.g., user device 305 in FIG. 3) that is part of a vaporizer system. These digital devices may provide an interface for the user to engage and interact with functions related to the vaporizer, including communication of data to and from the vaporizer to the digital device or the like and/or additional third party processor (e.g., servers such as the server 307 in FIG. 3). For example, a user may control some aspects of the vaporizer (temperature, dosage, etc.) and/or data transmission and data receiving to and from vaporizer, optionally over a wireless communication channel between first communication hardware of the device and second communication hardware of the vaporizer. Data may be communicated in response to one or more actions of the user (e.g. including interactions with a user interface displayed on the device), and/or as a background operation such that the user does not have to initiate or authorize the data communication process.

User interfaces may be deployed on a digital device and may aid the user in operating the vaporizer. For example, the user interface operating on a digital device may include icons and text elements that may inform the user of various ways that vaporizer settings can be adjusted or configured by the user. In this manner (or in others consistent with the current subject matter) information about a vaporizer can be presented using a user interface displayed by the communication device. Icons and/or text elements may be provided to allow a user to see information about vaporizer status, such as battery information (charge remaining, vapor draws remaining, time to charge, charging, etc.), cartridge status (e.g., type of cartridge and vaporizable material, fill status of cartridge, etc.), and similar device status. Icons and/or text elements may be provided to allow a user to update internal software (a.k.a., firmware) in the vaporizer. Icons and text elements may be provided to allow a user to set security and/or authorization features of vaporizer, such as setting a PIN code to activate the device or the use of personal biometric information as a means of authentication. Icons and text elements may be provided to allow a user to configure foreground data sharing and related settings.

A vaporizer may include or incorporate one or more authentication features. For example, the user interface ("app") may include, for example, PIN-based authentication, biometric authentication (which can include fingerprint based authentication, iris scan based authentication, facial recognition based authentication, and/or the like). Authorization may include age-analysis, such as an estimation or calculation of user age based on analysis of facial features. Authorization may be used to lock/unlock the vaporizer.

The authentication process can be embodied as a feature of an application that is installed and running on a personal digital device capable of communicating data through the use of wired or wireless methods (e.g. as part of a vaporizer system as described herein). The personal digital device (e.g., smartphone) may have an operating system capable of running application(s).

A vaporizer may be rendered inactive after a period of inactivity, for example by entering into a "sleep mode" when there is no usage detected for a predetermined and/or preset period of time. In some implementations of the current subject matter, in order for the vaporizer to be activated, and thereby be capable of being used by the user for the purpose of generating vapor, the user must be authenticated to ensure that the device is being utilized by the intended end user, and to prevent unauthorized use, or accidental or unintended activation of the device, or use of the device by an individual not of legal age to ingest the active component, including nicotine or cannabis. Personal identification number (PIN) based authentication may apply a user selected PIN code to authenticate the end use. Biometric authentication may be used, optionally using one or more approaches. For example, a fingerprint based authentication process may authenticate the end user. An iris scan based authentication process may use an eye or iris scan, or the like, to authenticate the end user. Facial recognition based authentication may use a face scan or image processing algorithm to authenticate the end user. Iris scan based authentication and facial recognition based authentication may be particularly useful if the personal digital device has a camera, such as a forward facing camera.

A personal vaporizer may be deactivated following a threshold criteria being met. For example, the vaporizer may be rendered inactive after a period of inactivity. The period of inactivity may be preset and/or selected by the user (e.g., using the control software of running on the personal digital device). Thus, the period of inactivity may be a configurable parameter of the vaporizer. The application software/firmware may include functionality to unlock or activate the vaporizer using authentication, as mentioned above.

An authentication process may be performed. If the authentication process is unsuccessful, the vaporizer may remain deactivated. If the authentication process is successful, the vaporizer may be unlocked and made ready for use.

A vaporizer may perform onboard data gathering, data analysis, and/or data transmission methods. As mentioned, a vaporizer having wired or wireless communication capability may interface with digital consumer technology products such as smart phones, tablet computers, laptop/netbook/desktop computers, wearable wireless technologies such as "smart watches," and other wearable technology such as Google "Glass," or similar through the use of programming, software, firmware, GUI, wireless communication, wired communication, and/or software commonly referred to as application(s) or "apps." A wired communication connection can be used to interface the vaporizer to digital consumer technology products for the purpose of the transmission and exchange of data to/from the vaporizer from/to the digital consumer technology products (and thereby also interfacing with apps running on the digital consumer technology products.) A wireless communication connection can be used to interface the vaporizer to digital consumer technology products for the transmission and exchange of data to/from the vaporizer from/to the digital wireless interface. The vaporizer may use a wireless interface that includes one or more of an infrared (IR) transmitter, a Bluetooth interface, an 802.11 specified interface, and/or communications with a cellular telephone network in order to communicate with consumer technology.

A vaporizer can interface (e.g., communicate) with digital consumer technology products and with apps as a way of relaying information and data to add additional functionality. This additional functionality may include (but is not limited to): (a) setting and/or specifying a desired number of activation cycles over a period of time; (b) setting and/or specifying one or more reminders, alarms, or similar to notifications for a user; (c) setting and/or specifying a user-desired dose Or doses for delivery of active substance(s) per inhalation; (d) setting and/or specifying a desired total delivered dose active substance(s) over a period of time—such as a total daily dose; (e) setting and/or specifying one or more power settings of the vaporizer to modulate a vapor and/or aerosol strength, a vapor and/or aerosol density, a vapor and/or aerosol volume, a vapor and/or aerosol flavor, a vapor and/or aerosol temperature, and/or other vapor and/or aerosol characteristics of a vapor and/or aerosol generated by the vaporizer; (f) setting and/or specifying power settings of the vaporizer to modulate, adjust, configure or similar the settings of the device as they relate to battery life and/or performance; (g) setting and/or specifying configurations of the vaporizer related to the liquid components and formulation; (h) setting and/or specifying ambient temperature based environmental configurations; (i) setting and/or specifying humidity based environmental configurations; (j) setting and/or specifying altitude based environmental configurations; (k) setting and/or specifying temporal (e.g., time) based configurations; (l) setting and/or specifying parameters to minimize, maximize, and/or modulate the functional effects of the taste and/or flavor component of the vapor product; (m) setting and/or specifying functional effect parameters to minimize or maximize the functional effects related to pharmacodynamics and pharmacokinetics of an active ingredient or drug component of the vapor or aerosol product; (n) receiving and/or providing to a user, vaporizer alerts and notifications; (o) receiving and/or providing to a user, vaporizer alerts and notifications related to recharging (e.g., whether a battery (e.g., power source 103 in FIG. 1) needs to be recharged); (p) receiving and/or providing to a user, vaporizer alerts and notifications related to charge status (e.g., whether a battery is fully or partially charged); (q) receiving and/or providing to a user, vaporizer alerts and notifications related to liquid cartridge usage status—such as a number of usages or inhalations taken from a cartridge; (r) receiving and/or providing to a user, vaporizer alerts and notifications related to liquid cartridge remaining status—such as a number of usages or inhalations remaining in a cartridge; (s) receiving and/or providing to a user, alerts and notifications related to time-based liquid cartridge usage status—such as number of usages or inhalations taken over a preset and/or predetermined period of time, for example number of usages or inhalations taken per day; (t) receiving and/or providing to a user, alerts and notifications related to liquid cartridge contents—such as active component(s), strength, dosage (or similar), flavor profile (or similar), and general formulation (or similar); (u) receiving and/or providing to a user, alerts and notifications related to liquid cartridge, liquid cartridge assembly, or similar, requiring replacement; (v) receiving and/or providing to a user, alerts and notifications related to preset times for usage of the vaporizer; and, (w) receiving and/or providing to a user, heating element alerts and notifications status or "health"—such as number of cycles performed, and/or number of cycles remaining before suggested and/or required replacement of a heating element or heating element assembly.

The power settings of the vaporizer may be set and/or specified to modulate or configure the activation energy delivered to the heating element(s) as well as modulating or configuring the parameters of the heating element(s) being energized in relation to the time to peak activation or "warm up" or "ramp", and/or the time of maximum or peak activation, and/or the time of the heating element being deactivated or the "cool down" to effect and modulate vapor and/or aerosol strength, vapor and/or aerosol density, vapor and/or aerosol volume, vapor and/or aerosol flavor, vapor and/or aerosol temperature, and/or similar vapor and aerosol characteristics of the vapor or aerosol generated by the vaporizer. In an embodiment, the power settings of the vaporizer may be set and/or specified such that the user can make setting adjustments to the vaporizer to maximize battery life. In this case, the vaporizer may resultantly operate at lower energy output to preserve the maximum number of cycles that can be sustained per battery charge cycle. Conversely the power settings of the vaporizer may be set and/or specified such that the user can maximize performance in relation to the energy output of the device per cycle.

Cartridge-related settings of the vaporizer can be based on information about the cartridge, including liquid components and/or formulation, or similar such that the information relating to the liquid may be vaporized or aerosolized. The liquid related settings of the vaporizer can have predetermined as well as user configurable settings to modulate, configure, adjust or otherwise configure the device activation parameters. In an embodiment, settings related to user specific environmental configurations can be made such that the vaporizer optimizes heating element activation and activation parameters to optimize performance based on ambient temperature, humidity, and/or altitude. For example, the vaporizer may have configurations such as cold weather or warm weather settings, humidity settings, and/or altitude settings.

A vaporizer may be configured (programmed) with time based settings, such as for example, user specific temporal configurations such as the user preferring higher active component delivery per inhalation at specific times of the day. A vaporizer can be configured such that the vaporizer delivers dosages of an active component based on the time of day. For example, the vaporizer can be configured such that the dosage delivered to the user is highest, or at maximum value (or similar) in the evening and is held at a lower delivered dose per inhalation, or minimum value (or similar) earlier in the day. The user can program these settings (and others described herein) based on personal preference.

Taste and/or flavor related settings of the vaporizer can minimize, maximize, and or modulate functional effects of the taste and/or flavor component of the vapor product. For example, the vaporizer can be configured to activate in such a way that the flavor delivered from the vapor or aerosol is minimized, maximized, or modulated over the period of an inhalation. Some components of the liquid being vaporized that may contribute to the flavor characteristics of the vapor or aerosol may be more profound, more prevalent, or more substantial when the vaporizer is activated with higher temperature ranges being generated by the heating element than when lower temperature ranges are being generated by the heating element (within the range of temperatures that the heating element may operate in order to generate a vapor or aerosol for inhalation by the user). For example, the user may set the vaporizer to perform for maximal, minimal, moderate, or another interim value of flavor for the vapor or aerosol product. The vaporizer may modulate the heating element activation cycle accordingly.

Functional effect-related setting of the vaporizer can minimize, maximize, or modulate the functional effects related to pharmacodynamics and pharmacokinetics of an active ingredient or drug component of the vapor or aerosol product. For example, the vaporizer can be configured to activate in such a way that the active component or drug delivered from the vapor or aerosol is minimized or maximized in terms of target tissue or organ delivery. Particle size may be modulated. A user may be using a vaporizer for the delivery of nicotine as the active or drug component in the vapor or aerosol. It may be desirable for (or by) the user to have an option for more rapid delivery of the nicotine to the bloodstream—such as after a period of not having nicotine (when the user's urge or craving is likely to be elevated). Alternatively, at times it may be desirable for (or by) the user to have a slower absorption of nicotine into the blood stream such as at times when: (i) the user's craving or urge is low, (ii) when the user wants to have a more prolonged period of time before they have the urge or craving for nicotine—such as prior to going to sleep, or an event where they will be unable to use the device for dosing or administration of the nicotine. The vaporizer settings relating to the activation of the device and the temperature of the heating element and heating element activation characteristics may be modulated such that, for example, at lower temperature activation the particle size of the drug component is larger than at times of a higher temperature activation of the heating element. Thus, by modulating the input of thermal or heat energy inputted into the vaporization chamber by the heating element to volatize or vaporize the liquid containing the active component(s) or drug(s), the characteristics of the vapor or aerosol in relation to the particle size of the active component(s) or drug(s) can be wholly or partially modulated by the user. These settings can also be used by the end user or healthcare provider (or similar) to reduce dependence on the active component(s) or drug(s) such as nicotine. This transition can also be used in conjunction with nicotine dosage reduction for reducing or mitigating the user's nicotine dependence or addiction.

An app may receive alerts and notifications associated with the vaporizer. These alerts and notifications can include, for example: battery life status, battery condition data (such as number of battery cycles), and battery "health" (such that the user can be notified, as desired, to the current and "real time" overall condition of the vaporizer internal battery(ies)).

A vaporizer and/or an associated application (app) running on a digital consumer technology product (e.g. a device that forms or is part of a vaporizer system as described above) may share data with a manufacturer, manufacturer affiliate, or other entity (retailer, healthcare provider, supplier, marketing entity, etc.). A vaporizer and/or an associated application may gather, receive, log, store, transmit, extrapolate, and/or the like, anonymous or user specific usage data—such as frequency of use. A vaporizer and/or an associated application can gather, receive, log, store, transmit, extrapolate, and/or the like, user specific usage data such as activation cycle characteristics, such as duration of activations and user specified activation settings (if applicable.) A vaporizer and/or an associated application can gather, receive, log, store, transmit, extrapolate, and/or the like, user specific demographic information. A vaporizer and/or an associated application can gather, receive, log, store, transmit, extrapolate, and/or the like, user specific socioeconomic information. A vaporizer and/or an associated application can gather, receive, log, store, transmit, extrapolate, and/or the like, user specific information. A vaporizer and/or an associated application can gather, receive, log, store, transmit, extrapolate, and/or the like, user specific feedback information. A vaporizer and/or an associated application can gather, receive, log, store, transmit, extrapolate, and/or the like, user specific demographic information. A vaporizer and/or an associated application can gather, receive, log, store, transmit, extrapolate, and/or the like, user specific feedback information using surveys, polls, and the like, and/or data analytics.

A vaporizer and/or an associated application can gather, receive, log, store, transmit, extrapolate, and/or the like, anonymous and/or user specific usage and/or reliability data such as device errors or malfunctions. A vaporizer and/or an associated application can gather, receive, log, store, transmit, extrapolate, and/or the like, user specific usage and/or reliability data such as requests for warranty services, repairs, and or replacements, etc. A vaporizer and/or an associated application can gather, receive, log, store, transmit, extrapolate, and/or the like, user specific customer satisfaction data such as requests for technical support. A vaporizer and/or an associated application can gather, receive, log, store, transmit, extrapolate, and/or the like, user specific sales lead data such as requests for product information. A vaporizer and/or an associated application can gather, receive, log, store, transmit, extrapolate, and/or the like, user specific usability data such as requests for usage instructions. A vaporizer and/or an associated application can gather, receive, log, store, transmit, extrapolate, and/or the like, user specific information such as requests for information on product features or functions. A vaporizer and/or an associated application can gather, receive, log, store, transmit, extrapolate, and/or the like, user specific marketing data such as requests for information on purchasing a vaporizer and/or acquiring a vaporizer by way of a prescription from a physician or healthcare provider.

A vaporizer and/or an associated application can gather, receive, log, store, transmit, extrapolate, and/or the like, vaporizer data indicating misuse or abuse of the vaporizer. A vaporizer and/or an associated application can gather, receive, log, store, transmit, extrapolate, and/or the like, vaporizer and/or use data and/or data transmission features that can be used to locate the vaporizer. The vaporizer and/or an associated application can gather, receive, log, store, transmit, extrapolate, and/or the like, data and/or data transmission features that can be used to locate the vaporizer if it is lost or stolen. A vaporizer, via an associated application, can gather, receive, log, store, transmit, extrapolate, and/or the like, notifications regarding product recalls or similar issues and/or inform the user of such recalls or issues. A vaporizer, via an associated application, can gather, receive, log, store, transmit, extrapolate, data sharing, and/or the like, notifications regarding manufacturer terms and conditions (e.g., cartridge manufacturer) and/or inform the user of such terms and conditions, and/or receive approval of such terms and conditions from the user.

A vaporizer, via an associated application running on a device that is part of a vaporizer system, can gather, receive, log, store, transmit, extrapolate, data share, and/or the like, data from a network that may be used to identify, contact, or connect with other users of vaporizers, and may, via an associated application, gather, receive, log, store, transmit, extrapolate, data share, and/or the like, data from a network that may be used to identify, contact, or connect with other users within the network. The vaporizer may select and/or authorize the sharing of all or some of the data gathered, received, logged, stored, transmitted, extrapolated, shared, or the like by the vaporizer, or gathered directly from the user using applications associated with the vaporizer. A vaporizer may select and/or authorize the sharing, via a network, of all or some of the data gathered, received, logged, stored, transmitted, extrapolated, shared, or the like by the vaporizer, or gathered directly from the user using applications associated with the vaporizer. The network may comprise social media. The social media membership may comprise a user's family. The social media membership may comprise a user's friends. The social media membership may comprise a support group or similar (e.g., quit smoking group). The social media membership may comprise a third-party service, company, organization (e.g., church), other users of the vaporizer, or the like.

A vaporizer, and/or an associated application can gather, receive, log, store, transmit, extrapolate, and/or the like, data useful to perform software configuration of the device and or the device application(s). A vaporizer and/or an associated application can gather, receive, log, store, transmit, extrapolate, and/or the like, data useful or required to perform software configuration of the vaporizer and/or the associated application(s). A vaporizer and/or an associated application can gather, receive, log, store, transmit, extrapolate, and/or the like, data useful or required to perform software configuration of the vaporizer, and/or the associated application(s) where the software is configured by the manufacturer or manufacturer's subsidiary or representatives or third party or similar. A vaporizer and/or an associated application can gather, receive, log, store, transmit, extrapolate, and/or the like, data useful or required to perform third party software configuration of a vaporizer and/or the associated application(s). A vaporizer and/or an associated application can gather, receive, log, store, transmit, extrapolate, and/or the like, data useful or required to perform firmware updates of the vaporizer, and/or the associated application(s). A vaporizer and/or an associated application can provide for the notification of the user via a vaporizer, and/or an associated application that a firmware or similar updates to the vaporizer and/or an associated application is available and/or required for trouble shooting the device or remediating a problem or issue with the vaporizer, and/or an associated application which is preventing some aspect of intended or proper function(s) of the vaporizer and/or an associated application. A vaporizer and/or an associated application can provide for the notification of the user via the vaporizer and/or an associated application that a firmware or similar update to the vaporizer and/or an associated application is available and/or required for providing additional functions relating to or intended to improved vaporizer performance, enhance user experience, or similarly improve some aspect of intended or proper function(s) of the vaporizer and/or an associated application.

A vaporizer and/or an associated application can share data gathered by the vaporizer, or gathered directly from the user using the application with the user's healthcare provider. A vaporizer and/or an associated application can share data gathered by the vaporizer, or gathered directly from the user using the application with the user's healthcare network. A vaporizer and/or an associated application can share data gathered by the vaporizer or gathered directly from the user using the application with the user's insurance provider. A vaporizer and/or an associated application can share data gathered by the vaporizer, or gathered directly from the user using the application with the user's pharmacy and/or prescription drug provider, or the like. A vaporizer and/or an associated application can depersonalize or otherwise make anonymous data gathered by the vaporizer or gathered directly from the user so that the depersonalized data can be shared or used for purposes such as research, analysis, publication, or similar purposes.

A vaporizer and/or an associated application can provide for the notification of the user via the vaporizer and/or the associated application of the availability of a prescription issued or written for the end user being ready for pick-up, delivery, shipment to the user or similar of a prescription component intended for delivery to the patient by a vaporizer. For example, a pharmacy may send a notification to the user, via the vaporizer and/or an associated application, such as to notify the user that their prescription for a vaporizer or vaporizable material (e.g., cartridges or liquids) is available for the user to pick up from the pharmacy (other commercial venues, not limited to pharmacies, may also do this, including shops, dispensaries, etc.). A vaporizer and/or an associated application can allow for healthcare providers, networks, agents, authorized third parties or similar entities to send alerts, messages, surveys, or similar to the user via the vaporizer and/or the associated application. A vaporizer and/or an associated application can allow for healthcare providers, networks, agents, authorized third parties or similar entities to access data that is generated as a result of surveys, or similar through the vaporizer and/or the associated application.

A vaporizer and/or an associated application can authorize (e.g., allow) a healthcare provider to configure, adjust, modulate, and/or manipulate vaporizer settings. A vaporizer and/or an associated application can authorize a healthcare provider to configure, adjust, modulate, and/or manipulate vaporizer settings which the user is not authorized to change, alter, reconfigure or change the settings, configurations, etc. made by the healthcare provider. A vaporizer and/or an associated application can authorize a representative or agent of the healthcare provider to configure, adjust, modulate, and/or manipulate vaporizer settings which the user is not authorized to change, alter, reconfigure or change the settings, configurations, etc. made by the representative or agent of the healthcare provider.

A vaporizer and/or an associated application can share user specific information, such as end user ownership of products relating to the device, device components, device accessories or similar data, gathered by the vaporizer or gathered directly from the user through the use of the application. A vaporizer and/or an associated application can share user specific information, such as end user purchasing of products relating to the device, device components, device accessories or similar data, gathered by the vaporizer or gathered directly from the user through the use of the application. A vaporizer and/or an associated application can provide for the notification of the user via the vaporizer and/or the associated application of notifications from retailer(s) or similar regarding product promotions. A vaporizer and/or an associated application can provide for the notification of the user via the vaporizer and/or the associated application similar of notifications from retailer(s) or similar regarding product availability. A vaporizer and/or an associated application can provide for the notification of the user via the vaporizer and/or the associated application similar of notifications from retailer(s) or similar regarding release of new product or accessories.

A vaporizer and/or an associated application can use demographic or similar location services to find retail locations in geographic proximity of the user. A vaporizer and/or an associated application can gather, receive, log, store, transmit, extrapolate, and/or the like, data relating to device purchasing, device accessories purchasing, vaporizer liquid and associated packaging or assembly purchasing, frequency of purchasing, point of sale, discounts applied by user when purchasing, and related or similar information. A vaporizer and/or an associated application can gather, receive, log, store, transmit, extrapolate, and/or the like, data relating to device purchasing, device accessories purchasing, vaporizer liquid and associated packaging or assembly purchasing, frequency of purchasing, point of sale, discounts applied, and related or similar information.

A vaporizer and/or an associated application can provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar. A vaporizer and/or an associated application can provide for the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar.

A vaporizer and/or an associated application can render the vaporizer inactive and unable to be used, as mentioned above. For example, a vaporizer and/or an associated application can render the vaporizer inactive and unable to be used if a malfunction or similar has occurred. A vaporizer and/or an associated application can render the vaporizer inactive and unable to be used until the authorized user enters a Personal Identification Number (PIN) using the application which then activates the vaporizer. A vaporizer and/or an associated application can render the vaporizer inactive and unable to be used until the authorized user has a biometric identifier that when recognized or confirmed or verified or similar, using the application, activates the vaporizer. As discussed above, unauthorized use of a vaporizer and/or an associated application can be prevented by using PIN and/or unique biometric identifier. A vaporizer and/or an associated application can save device data and personal settings for individual users so that more than one user may use the vaporizer. A vaporizer and/or an associated application can save device data and personal settings to be saved for individual users where the settings for device data and personal settings for different users can be applied to the vaporizer and the intended user through the application. The user may select their saved configurations for a vaporizer and the respective device will operate under that user selected configuration. A vaporizer and/or an associated application can have the ability for the user or users to have one or more of user settings and/or configurations that are saved and can be selected by users. A vaporizer and/or an associated application can have the ability to allow saved user settings and personal settings or configurations to be shared by the user through the application and/or an associated network. A vaporizer and/or an associated application can allow other user settings and/or configurations to be shared with the user through the application or an associated network.

A vaporizer and/or an associated application can facilitate, prompt, or the like, a user to rate (such as through common methods such a 1-10 where "10" is the best, or 1-5 "stars" where "5" stars is the best) their vaporizer, vaporizer configurations, cartridge (e.g., particular flavor or brand of cartridges, etc.), or the like. A vaporizer and/or an associated application can facilitate, prompt, or the like, the user to rate other user configurations. A vaporizer and/or an associated application can share and access a database of user configurations that may or may not have ratings and be able to access the user configurations through the application and download user configurations for use in the user's own device. A vaporizer and/or an associated application can have the ability to share and access a database of user configurations that may or may not have ratings and be able to access the user configurations through the application and upload their user configurations for use in other users' devices.

A vaporizer and/or an associated application can share user data with the manufacturer, manufacturers subsidiaries, manufactures agents, or a third party for generating user profiles based on user specific usage data, demographic data, socioeconomic data or similar. A vaporizer and/or an associated application can have the ability to utilize user data shared with the manufacturer, manufacturer's subsidiaries, manufacturer's agents, or a third party to determine specific user profiles.

A vaporizer and/or an associated application can allow, facilitate, authorize, confirm or similar the sharing of data between the associated application and other application(s) that may be installed or a component of the user's personal digital device. A vaporizer and/or an associated application can share information and/or data with a social media application. A vaporizer and/or an associated application can share information and/or data with email service, email provider, email hosting, or similar applications. A vaporizer and/or an associated application can share information and/or data with text message, short message service (SMS), or similar applications. A vaporizer and/or an associated application can share information and/or data with a location based services application. A vaporizer and/or an associated application can share information and/or data with a map or mapping, navigation, location or similar application. A vaporizer and/or an associated application can share information and/or data with healthcare, healthcare provider, healthcare services, healthcare network or similar application. A vaporizer and/or an associated application can share information and/or data with pharmacy, pharmacy type service provider or similar application. A vaporizer and/or an associated application can share information and/or data with a weather, weather forecasting, weather reporting or similar application. A vaporizer and/or an associated application can share information and/or data with the device manufacturer's application. A vaporizer and/or an associated application can share information and/or data with a research or a research orientated application. A vaporizer and/or an associated application can share information and/or data with a vaporizer retailer or similar consumer device application.

A vaporizer and/or an associated application can have the ability to authorize or allow data gathering, receiving, logging, storing, transmission, extrapolation or similar for the purpose of the device or associated application sending error codes or error reports to the manufacturer, manufacturer's subsidiaries, manufacturer's agents, or a third party for the purpose of addressing problems with device performance or function. A vaporizer and/or an associated application can have the ability to authorize or allow data gathering, receiving, logging, storing, transmission, extrapolation or similar for the device or associated application to send error codes or error reports to the manufacturer, manufacturer's subsidiaries, manufacturer's agents, or a third party for the purpose of addressing problems with device application(s). A vaporizer and/or an associated application can have the ability to authorize or allow data gathering, receiving, logging, storing, transmission, extrapolation or similar for the device or device application to send error codes or error reports to the manufacturer, manufacturer's subsidiaries, manufacturer's agents, or a third party for the purpose of extrapolating data metrics that relate to device malfunctioning. A vaporizer and/or an associated application can have the ability to authorize or allow data gathering, receiving, logging, storing, transmission, extrapolation or similar for the purpose of the device or associated application sending error codes or error reports to the manufacturer, manufacturer's subsidiaries, manufacturer's agents, or a third party for the purpose of gathering, receiving, logging, storing, transmission, extrapolation or similar of data that may relate to manufacturing, quality control or similar issues or potential problems related to the device, device components, or liquid being used in the device. A vaporizer and/or an associated application can have the ability to gather, receive, log, store, transmit, extrapolate, or similar, data for troubleshooting device issues or problems. A vaporizer and/or an associated application can have the ability to gather, receive, log, store, transmit, extrapolate, or similar, data for troubleshooting device issues or problems that may relate to user error.

A vaporizer and/or an associated application can have the ability to use methods of data transmission such as wireless and wired technologies. A vaporizer and/or an associated application can have the ability to use methods of data transmission such as wireless and wired technologies to perform one or more of the functions, capabilities, methods, abilities, etc., described herein. A vaporizer and/or an associated application can have the ability to use methods of data transmission such as WiFi, Bluetooth, cellular, 3G, 4G, near field communication (NFC), or similar for the transmission of data to the user's personal digital device. Such communications, may occur through establishment of a wireless communication channel between first communication hardware of a device and second communication hardware of a vaporizer. A vaporizer and/or an associated application can have the ability to use methods of data transmission such as Wi-Fi, Bluetooth, cellular, 3G, 4G, near field communication (NFC), or similar for the transmission of data to a network. Accordingly, the first communication hardware and the second communication hardware can include circuitry and one or more transceivers configured for at least one of these (or other comparable) communication approaches. A vaporizer and/or an associated application can have the ability to use methods of data transmission such as text messaging or SMS. A vaporizer and/or an associated application can have the ability to use methods of data transmission such as electronic mail or email. A vaporizer and/or an associated application can have the ability to use methods of data transmission such as notifications or push notifications to the user's digital device, which can include the first communication hardware.

A vaporizer and/or an associated application can include features (e.g. software-based buttons or controls and/or physical input devices or controls) that enable user control of the functionality, features, configurations etc. of a vaporizer and/or an associated application using various features of the application referred to as configurations or settings. These settings can include, but are not limited to exemplary general usage settings such as: (a) desired number of activations cycles over a period of time; (b) configuring and or setting reminders, alarms, or similar to notify the user; (c) desired dose delivery of active substance per inhalation; (d) desired total delivered dose over a period of time, such as a total daily dose; (e) power settings of vaporizer to modulate the vapor or aerosol strength, vapor or aerosol density, vapor or aerosol volume, vapor or aerosol flavor, vapor or aerosol temperature or similar vapor or aerosol characteristics of the vapor or aerosol generated by the device (the power settings could modulate or configure the activation energy delivered to the heating element(s) as well as modulate or configure the parameters of the heating element(s) being energized in relation to the time to peak activation or "warm up" or "ramp", and or the time of maximum or peak activation, and or the time of the heating element being deactivated or the "cool down" to effect and modulate the vapor or aerosol strength, vapor or aerosol density, vapor or aerosol volume, vapor or aerosol flavor, vapor or aerosol temperature or similar characteristics of the vapor or aerosol generated by the device); (f) power settings of vaporizer to modulate, adjust, configure or similar the settings of the device as they relate to battery life and performance such that the user can make setting adjustment to the device to maximize battery life and the device will resultantly operate at lower energy output to preserve the maximum number of cycles that be sustained per battery charge cycle (conversely the user could modulate, adjust, configure or similar the settings of the device to maximize performance in relation to the energy output of the device per cycle); (g) settings related to the liquid components and formulation or similar such that the information relating to the liquid to be vaporized or aerosolized can have predetermined as well as user configurable settings to modulate, configure, adjust or similar vaporizer activation parameters; (h) settings related to user specific environmental configurations such as cold weather or warm weather settings such that the device optimizes heating element activation and activation parameters to optimize performance based on ambient temperature; (i) settings related to user specific environmental configurations such as high or low humidity settings such that vaporizer optimizes heating element activation and activation parameters to optimize performance based on user locale humidity values or ranges; (j) settings related to user specific environmental configurations such as user locale altitude settings such that vaporizer optimizes heating element activation and activation parameters to optimize performance based on end user altitude; (k) settings related to user specific temporal configurations such as the user preferring higher active component delivery per inhalation at specific times of the day (for example, vaporizer can be configured such that it delivers higher dosage of active component related to a time of day such that the dosage delivered to the user is highest, or at maximum value or similar, in the morning and tapers down to a lower delivered dose per inhalation, or minimum value, or similar at the end of the evening); (l) settings related to modulating vaporizer performance and activation parameters to minimize or maximize the functional effects of the taste or flavor component of the vapor product such that the vaporizer can be configured to activate in such a way that the flavor delivered from the vapor or aerosol is minimized or maximized (for example components of the liquid being vaporized that may contribute to the flavor characteristics of the vapor or aerosol may be more profound, or more prevalent, or more substantial when vaporizer is activated with higher temperature ranges being generated by the heating element than when lower temperature ranges are being generated by the heating element within the range of temperatures that the heating element may operate within in order to generate a vapor or aerosol for inhalation by the user); for example the user may set vaporizer to perform for maximal, minimal, moderate, or another interim value of flavor for the vapor or aerosol product and the heating element activation cycle will be modulated accordingly; (m) settings related to modulating vaporizer performance and activation parameters to minimize or maximize the functional effects related to pharmacodynamics and pharmacokinetics of the active or drug component of the vapor or aerosol product such that vaporizer can be configured to activate in such a way that the active component or drug delivered from the vapor or aerosol is minimized or maximized in terms of target tissue or organ delivery; (n) device alerts and notifications such as battery life status and battery condition(s) data such as number of battery cycles and battery "health" such that the user can be notified as desired to the current in real time and overall condition of the device's internal battery, and the device's charging case internal battery; (o) device alerts and notifications such as the vaporizer battery requiring recharging; (p) device alerts and notifications such as vaporizer battery being fully charged; (q) device alerts and notifications such as liquid cartridge status, such as number of usages or inhalations taken and number or usages remaining; (r) device alerts and notifications such as liquid cartridge contents such as active component(s) and strength or dosage or similar, and flavor profile or similar, and general formulation; (s) device alerts and notifications such as liquid cartridge or liquid cartridge assembly or similar requiring replacement; (t) device alerts and notifications such as predetermined or preset times for usage of vaporizer; (u) device alerts and notifications such as device heating element status or "health" such as number of cycles performed and number of cycles remaining before suggested or required replacement of heating element or heating element assembly.

Settings can include, but are not limited to device manufacturer data sharing settings such as: (a) Anonymous or user specific usage data such as frequency of use; (b) Anonymous or user specific usage data such as activation cycle characteristics such as duration of activations and user specified activation settings if applicable; (c) User specific data such as demographic information; (d) User specific data such as socioeconomic information; (e) User specific data such as user feedback through the use of surveys or similar; (f) Anonymous or user specific usage data such device errors or malfunctions; (g) User specific data such as requests for warranty services or repairs or replacements or similar; (h) User specific data such as requests for technical support; (i) User specific data such as requests for product information; (j) User specific data such as requests for usage instructions; (k) User specific data such as requests for information on product features or functions; (l) User specific data such as requests for information on purchasing product or acquiring the product through a prescription from a physician or healthcare provider; (m) Device data indicating misuse or abuse of the device; (n) Device data and data transmission features used to locate the device if the device is lost or stolen; (o) Notifications to the user through the device or application(s) relating to product recall(s) or similar issues; (p) General data sharing to manufacture terms and conditions recognition and user agreement to said terms.

Settings can include, but are not limited to user, usage, system, device, and operational data settings such as: (a) Settings relating to selecting and authorizing the sharing of all or some of the data gathered by the device or gathered directly from the user through the use of an application(s) to a network(s); (b) Where network(s) may be social media; (c) Where network(s) may be comprised of the user's family and or friends; (d) Where network(s) may be comprised of a support group or similar; (e) Settings relating to the use of the sharing of data over a network(s) that may be used to identify, contact, or connect with other users of the device; (f) Where other network(s) may be a third party service, company, organization or similar.

Settings can include, but are not limited to software configuration and firmware updating settings such as: (a) Settings relating to the sharing and transmission of data required or useful to perform software configuration of the device and or the device application(s); (b) Settings relating to the sharing and transmission of data required to perform software configuration of the device and or the device application(s) where the software is configured by the manufacturer or manufacturers subsidiary or representatives or third party or similar; (c) Settings relating to the sharing and transmission of data required to perform software configuration of the device and or the device application(s) where the software is configured by a third party; (d) Settings relating to the authorization for the sharing and transmission of data required to perform firmware or similar updates to the device and or application; (e) Settings relating to the notification of the user through the device or application(s) that a firmware or similar updates to the device and or application(s) is available and or required; (f) Settings relating to the notification of the user through the device or application(s) that a firmware or similar updates to the device and or application(s) is available and or required as a means of trouble shooting the device or remediating a problem or issue with the device or application(s) preventing some aspect of intended or proper function(s).

Settings can include, but are not limited to healthcare system data sharing settings such as: (a) Settings relating to the sharing of all or some of the data gathered by the device or gathered directly from the user through the use of application(s) to the user's healthcare provider; (b) Settings relating to the sharing of all or some of the data gathered by the device or gathered directly from the user through the use of application(s) to the user's healthcare network; (c) Settings relating to the sharing of all or some of the data gathered by the device or gathered directly from the user through the use of application(s) to the user's insurance provider; (d) Settings relating to the sharing of all or some of the data gathered by the device or gathered directly from the user through the use of application(s) to the user's pharmacy or prescription drug provider or similar; (e) Settings relating to the notification of the availability of a prescription issued or written for the end user being ready for pick-up, delivery, and/or shipment to the user or similar of a prescription component intended for delivery to the patient by the device. For example, a pharmacy could send a notification to the user, through the device application, such as to notify the user that their prescription for the device or device components is available for the user to pick up from the pharmacy; (f) Settings relating to the authorization of a healthcare provider to configure, adjust, modulate, manipulate or similar the device settings; (g) Settings relating to the authorization of a healthcare provider to configure, adjust, modulate, manipulate or similar the device settings where the user is not authorized to change, alter, reconfigure or similar the settings, configurations, or similar made by the healthcare provider; (h) Settings authorizing a representative or agent or similar of the healthcare provider to configure, adjust, modulate, manipulate or similar the device settings where the user is not authorized to change, alter, reconfigure or similar the settings, configurations, or similar made by the healthcare representative or agent or similar; (i) Settings allowing for data shared with the healthcare provider or network to be depersonalized or otherwise made anonymous and used for other purposes such as research, analysis, publication, or similar purposes; (j) Settings allowing for healthcare providers, networks, agents, authorized third parties or similar to send alerts, messages, surveys, or similar through the device application(s); (k) Settings allowing for healthcare providers, networks, agents, authorized third parties or similar to access data that is generated as a result of surveys, or similar through the device application(s).

Settings can include, but are not limited to retailer and/or consumer facing data settings such as: (a) Settings relating to the sharing user specific information such as product, device, component, accessories or similar details; (b) Settings relating to receiving notifications from retailer(s) or similar regarding product promotions; (c) Settings relating to receiving notifications from retailer(s) or similar regarding product availability; (d) Settings relating to receiving notifications from retailer(s) or similar regarding release of new product or accessories; (e) Settings relating to using demographic or similar location services to find retail locations in geographic proximity of the user; (f) Settings relating to the sharing of data that may be used for demographic, socioeconomic, or similar marketing or promotional activities; (g) Settings relating to the gathering of data relating to device purchasing, device accessories purchasing, vaporizer liquid and associated packaging or assembly purchasing, frequency of purchasing, point of sale, discounts applied by user when purchasing, and related or similar information; (h) Settings relating to the sharing of data relating to device purchasing, device accessories purchasing, vaporizer liquid and associated packaging or assembly purchasing, frequency of purchasing, point of sale, discounts applied, and related or similar information; (i) The use of the application to provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar; (j) Settings relating to the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar.

Settings can include, but are not limited to device access settings such as: (a) Settings relating to rendering the device inactive and unable to be used; (b) Settings relating to rendering the device inactive and unable to be used where the authorized user has a Personal Identification Number (PIN) that when entered using the application activates the device; (c) Settings relating to rendering the device inactive and unable to be used where the authorized user has a biometric identifier that when recognized or confirmed or verified or similar using the application activates the device; (d) Settings relating to rendering the device inactive and unable to be used where the authorized user has a biometric identifier that when recognized or confirmed or verified using the application activates the device where the biometric identifier is a fingerprint; (e) Settings relating to rendering the device inactive and unable to be used where the authorized user has a biometric identifier that when recognized or confirmed or verified using the application activates the device where the biometric identifier is an eye or iris or similar scan; (f) Settings relating to rendering the device inactive and unable to be used where the authorized user has a biometric identifier that when recognized or confirmed or verified using the application activates the device where the biometric identifier is facial recognition; (g) Settings where unauthorized use of the device is prevented by using PIN or unique biometric identifier; (h) Settings relating to the sharing of data relating to the attempted unauthorized use of the device; (i) Settings relating to the sharing of data over a network to authorize the user and activate the device; (j) Settings relating to sharing of data such that biometric authentication can be performed through the use of a network; (k) Settings related to the time or duration of time that passes after use before the device is rendered inactive and authentication is required to authorize the device; (l) Settings related to the resetting or changing of user specific authentication information such as the PIN.

Settings can include, but are not limited to multiple user settings such as: (a) Settings relating to the sharing and transmission of data required or useful to perform software configuration of the device and or the device application(s); (b) Settings relating to the sharing and transmission of data required to perform software configuration of the device and or the device application(s) where the software is configured by the manufacturer or manufacturer's subsidiary or representatives or third party or similar; (c) Settings relating to the sharing and transmission of data required to perform software configuration of the device and or the device application(s) where the software is configured by a third party; (d) Settings relating to the authorization for the sharing and transmission of data required to perform firmware or similar updates to the device and or application; (e) Settings relating to the notification of the user through the device or application(s) that a firmware or similar updates to the device and or application(s) is available and/or required; (f) Settings relating to the notification of the user through the device or application(s) that a firmware or similar updates to the device and or application(s) is available and or required as a means of trouble shooting the device or remediating a problem or issue with the device or application(s) preventing some aspect of intended or proper function(s).

Settings can include, but are not limited to defined usage profile settings such as: (a) Settings related to the sharing of user data to the manufacturer, manufacturer's subsidiaries, manufacturer's agents, or a third party for the purpose of generating user profiles based on user specific usage data, demographic data, socioeconomic data or similar; (b) Where the use of user data shared with or sent to the manufacturer, manufacturer's subsidiaries, manufacturer's agents, or a third party for the purpose of generating user profiles based on user specific usage data, demographic data, socioeconomic data or similar is utilized to determine specific user profiles; (c) Where the user profiles are a group of setting configurations that correlate to a specific subset of users; (d) Where a subset of users may be based on demographic data, socioeconomic, personal data gathered through the use of the application, device usage data or similar; (e) Where user profiles may be specific to the subset of users and recommended device configuration based on user profile data could be available to the user of the device based on the user's similarities to a subset of users; (f) Where the user experience is optimized by using cumulative data from similar users to establish a default setting configuration for the device based on the user's demographic data, socioeconomic data or similar.

Settings can include, but are not limited to settings related to integration with other applications such as: (a) Settings to allow, facilitate, authorize, confirm or similar the sharing of data between the device application and other application(s) that may be installed or a component of the user's personal digital device; (b) Where other application(s) that the device application shares information with may be social media application(s); (c) Where other application(s) that the device application shares information with may be email service, email provider, email hosting, or similar application(s); (d) Where other application(s) that the device application shares information with may be text message, SMS, or similar application(s); (e) Where other application(s) that the device application shares information with may be location services application(s); (f) Where other application(s) that the device application shares information with may be map or mapping, navigation, location or similar application(s); (g) Where other application(s) that the device application shares information with may be healthcare, healthcare provider, healthcare services, healthcare network or similar application(s); (h) Where other application(s) that the device application shares information with may be pharmacy, or pharmacy type service provider or similar application(s); (i) Where other application(s) that the device application shares information with may be weather, or weather forecasting, or weather reporting or similar application(s); (j) Where other application(s) that the device application shares information with may be the device manufacturers application(s); (k) Where other application(s) that the device application shares information with may be research or research orientated application(s); (l) Where other application(s) that the device application shares information with may be device retailer or similar consumer device application(s).

Settings can include, but are not limited to error code and troubleshooting such as: (a) Settings relating to the authorization or allowance of data sharing for the purpose of the device or device application sending error codes or error reports to the manufacturer, manufacturer's subsidiaries, manufacturer's agents, or a third party for the purpose of addressing problems with device performance or function; (b) Settings relating to the authorization or allowance of data sharing for the purpose of the device or device application sending error codes or error reports to the manufacturer, manufacturer's subsidiaries, manufacturer's agents, or a third party for the purpose of addressing problems with device application(s); (c) Settings relating to the authorization or allowance of data sharing for the purpose of the device or device application sending error codes or error reports to the manufacturer, manufacturer's subsidiaries, manufacturer's agents, or a third party for the purpose of extrapolating data metrics that relate to device malfunctioning; (d) Settings relating to the authorization or allowance of data sharing for the purpose of the device or device application sending error codes or error reports to the manufacturer, manufacturer's subsidiaries, manufacturer's agents, or a third party for the purpose of gathering data that may relate to manufacturing, or quality control or similar issues or potential problems related to the device, device components, or liquid being used in the device; (e) Settings relating to the sharing of data for the purpose of troubleshooting device issues or problems. (f) Settings relating to the sharing of data for the purpose of troubleshooting device issues or problems that may relate to user error.

Settings can include, but are not limited to settings related to methods of communication such as: (a) Settings relating to the device or device application using methods of data transmission such as wireless and wired technologies; (b) Settings relating to the device or device application using methods of data transmission such as WiFi, Bluetooth, or similar for the transmission of data to the user's personal digital device; (c) Settings relating to the device or device application using methods of data transmission such as wired or wireless methods or similar for the transmission of data to a network; (d) Settings relating to the device or device application using methods of data transmission such as text messaging or SMS; (e) Settings relating to the device or device application using methods of data transmission such as electronic mail or email; (f) Settings relating to the device or device application using methods of data transmission such as notifications or push notifications on the user's digital device.

The application can be used to provide information on trouble shooting the device in the event of a performance issue or malfunction. The application can be used to provide safety information relating to the device or to the user. The application can be used to provide safety information relating to the maintenance, cleaning, or similar activities for the device. The application can be used to provide storage information for the device. The application can be used to provide information relating to the disposal or recycling of the device. The application can be used to provide information on the proper disassembly and assembly of the device. The application can be used to provide information such as the manufacturers, distributors, retailers, or similar website and or contact information. The application can be used to provide information such as a website uniform resource locator (URL) or link for internet forums that may relate to the use, troubleshooting, user experience, user reviews or similar. The application can be used to provide safety information relating to the device to the user. The application can be used to provide information on available products, accessories, or similar that may be related to the device. The application can be used to provide a space for advertising consumer products or services that may be related to the device. The application can be used to provide functions relating to personal user goals for device usage and to track usage as it relates to the users defined goals and to present the data in the forms of charts, graphs, or similar.

The systems, controller, and functions described above may be implemented with or executed by one or more computer systems. The methods described herein may be stored on a computer readable medium.

DOSE CONTROL. A vaporizer and/or vaporizer system may include dose control and/or dose metering. In general, dose control is described in U.S. patent application Ser. No. 14/960,259, filed on Dec. 4, 2015, and herein incorporated by reference in its entirety.

As described above, a vaporizer and/or a device that is part of a vaporizer system as defined above may include a user interface (e.g., including an app or application software) that may be executed on a device in communication, which may be configured to determine, display, enforce and/or meter dosing. For example, a vaporizer may have a "unit dose" mode/indicator that is displayed on the vaporizer and/or an application. The unit dose could be changed by the connected application and/or by directly controlling the vaporizer. For example, a user may want to go from 1 mg nicotine per dose to 2 mg of nicotine per dose.

The dose unit may be programmable. For example, a user may program a dose based on previous (recorded) use; e.g., the user may press a "start" button on the app, take enough puffs until satisfied, and then press "stop" on the app. In addition, the user may input user-specific data that may be helpful in determining and/or metering dosing. For example, the user may input body weight, gender, and any other relevant data. Such info can be used for adjusting dose of therapeutic drugs such as pain killer, sleep aid, etc. accordingly.

As mentioned, in some implementations of the current subject matter, the vaporizer and/or app running on a device that is connected (or connectable) to the vaporizer may record use or operation of the device and may play back this use later. In general, the vaporizer or app may record a first operational parameter (e.g., temperature setting, ramp time to heat, etc.) and a second use parameter (e.g., number of puffs, cumulative dose, use time, etc.), may store the recorded operational parameter and use parameter as a use profile, may associate the recorded use profile with a control, button, icon, etc., and may program the device operation based on the use profile, so that the operational parameter is modified automatically as the actual operational parameter tracks with the recorded operational parameter.

For example, the user may record a use profile including the number of puffs (e.g., draw events, inhalations, etc.) between changes in the temperature, as well as the temperature so that this use profile may be replayed later, e.g., by selecting a button or other indicator associated with the recorded/programmed use profile. In some embodiments, the vaporizer and/or app may record the temperature and one or more second use parameters, such as one or more of: puff time (duration), puff count (number of puffs), energy applied to vaporizable material (e.g., cumulative joules of energy), dosage/exposure, etc. Playback may be indexed on any of the recorded use parameters such as the number of puffs, cumulative duration of puffing, cumulative energy applied, cumulative dose, etc. and may set or modify the operational parameter (e.g., applied vaporization temperature, energy applied, etc.) of the vaporizer to the recorded temperature to match the recorded and/or programmed temperature as the vaporizer is operated, so that the same use profile will be followed. For example, a user may record a use profile while operating the device at a first temperature (e.g., 150° C.) for 5 draws (puffs), then increasing the temperature to 180° C. for five more puffs, then increasing the temperature to 200° C. for 10 puffs. The recorded operational profile may be stored on the vaporizer, app, or some other connected memory, and associated with a control (e.g., icon, graphic, text, button, etc.) on the vaporizer, app and/or a remote processor or memory. The recorded operational profile may then be played back, e.g., by selecting an icon (or button, control, text, etc.) on the app or vaporizer that has been associated with the recorded/programmed profile. During playback, the vaporizer may wait until the same or a similar operational parameter (e.g., puffs, time of use, applied power, dose, etc.) is matched or exceeded and may control the heater based on the recorded profile. In the example above, the recorded operational profile may be played back later by pressing the icon; the vaporizer and/or app may compare the use parameter (number of puffs, etc.) to the current operation of the vaporizer and may adjust the operational parameter accordingly to match the use profile.

Figure 20:
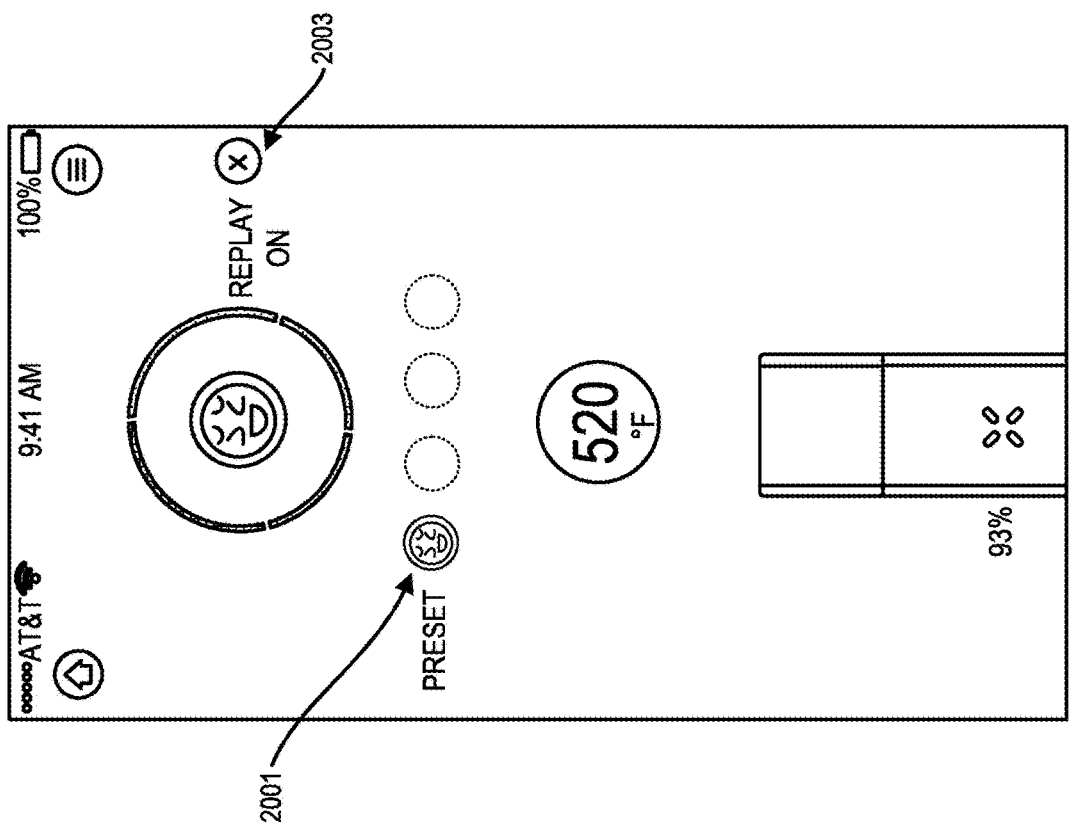
FIG. 20 illustrates features of an example user interface for programming /recording a use profile consistent with implementations of the current subject matter.
Figure 19F:
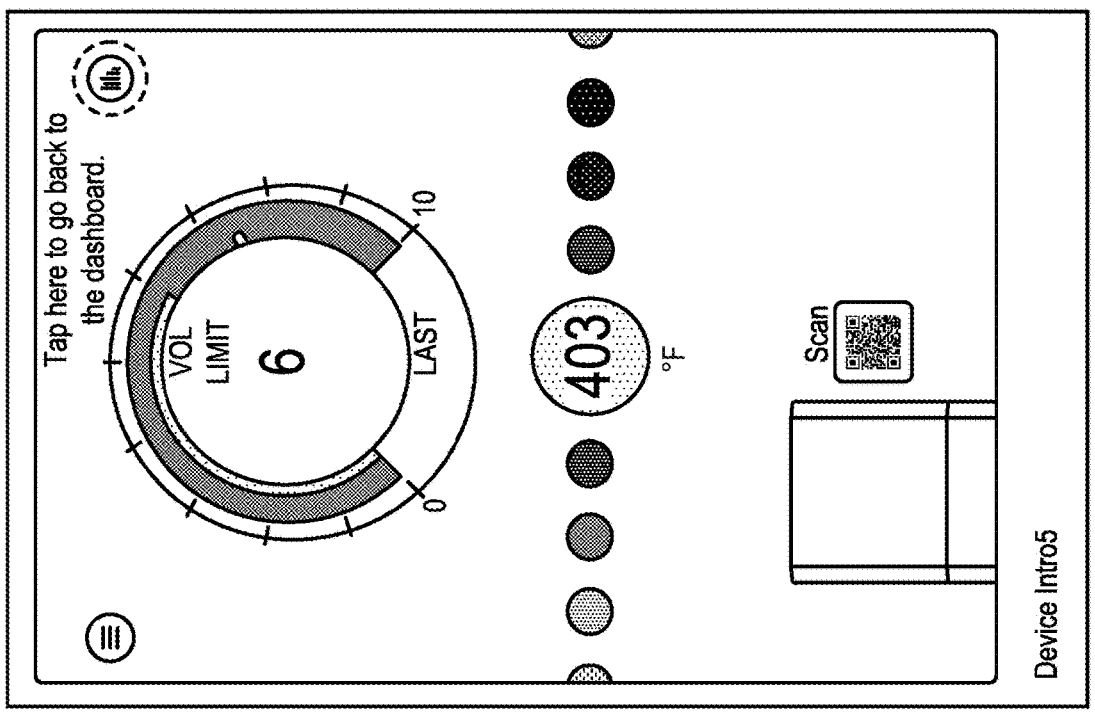

For example, FIG. 20 illustrates a screen of a user interface including an icon 2001 that has been associated with a use profile; by touching the icon 2001, the use profile may be replayed as indicated at 2003. Playback may be stopped by pressing another button/icon 2003.

The use profile may be recorded, or it may be programmed, or both (e.g., a recorded use profile may be modified by a user on the vaporizer and/or app, etc.).

In some examples, dose (e.g., cumulative dose) may be the use parameter that is monitored. In some implementations of the current subject matter, dose may be calculated as described in U.S. patent application Ser. No. 14/960,259, filed on Dec. 4, 2015, previously incorporated by reference in its entirety. The cumulative dose may be stored for transmission and/or display. Further, the dose may be used to control operation of the vaporizer.

In one example of a nicotine dose control, the user could set a target cap for how much nicotine he/she wants in a day. In some embodiments, the device won't lock the user out from having more, but it will notify if a target has been exceeded. Alternatively, the device may lock the user out.

In an example of THC dose regulation, the dose control may allow a user to treat symptoms without having too much psychoactive effect. For example, usage data can be shared with a doctor to allow for better prescription/administration. In general, for medical use, the vaporizer or app can correlate dose with logged symptoms. Alternatively or additionally, for recreational use, the vaporizer or app may allow a user to more easily figure out the right amount for them and then repeatedly deliver that dose.

In some implementations of the current subject matter, the application or vaporizer may inform the users of the driving under the influence (DUI) limit of THC in their state and set warning/alert when one time usage exceeds the limit based on estimated blood level (e.g., 5 ng/mL blood level in Colorado or 3.5-5 ng/mL blood level according to this report http://www.canorml.org/healthfacts/DUICreport.2005.pdf). The vaporizer or app may also include a table similar to the number of drinks vs. blood alcohol content (BAC) table included in department of motor vehicles (DMV) letters. The vaporizer and/or app may alternatively or additionally estimate blood THC concentration based on the user's body weight and gender info.

In some implementations, upon the app or vaporizer recognizing the cartridge, relevant and/or customized dosing information may be provided. For example, in one instance a comparison may be provided to alert a user of how a new cartridge compares in strength to other previously-used cartridges, providing the user with helpful information to control the amount consumed (e.g., by equating a dose across different strengths). Additionally, user preferences and behaviors may be used to enable the app or vaporizer to recommend a suggested dose. Such recommendations may also be tailored to create a customized experience based on other factors, such as day of the week, time of day, etc.

MONITORING—HEALTH and CESSATION. A vaporizer and/or applications running on a device that is part of a vaporizer system consistent with implementations of the current subject matter may also be configured to monitor usage for a digital health regimen, and/or smoking cessation, etc. For example, similar to weight loss monitoring devices, a vaporizer or an app or both may be useful for people who want to reduce nicotine consumption, and/or keep track of how much nicotine consumed within a certain amount of time. For example, the vaporizer and/or app may be configured to allow cigarette-e-cigarette dual users to log in how many cigarettes they consume and compare the total amount of HPHCs and nicotine they get on different days when they use different combinations.

The app and/or vaporizer may also provide additional motivation by providing messaging such as reporting how much of X compound is consumed, and may show how much money the former smoker is saving by reducing or eliminating smoking. This would be most relevant for nicotine, although it may be used for other substances as well. In some embodiments, the user may enter their usual price per pack of cigarettes, which may be used as the baseline. This may also be relevant for THC, since vaping is a more effective means of consumption. From anecdotal data, there may be a 5-10× multiplier between smoking and vaping; for example, someone who would vape x mg of THC would otherwise smoke 10× mg of THC in a given time interval. Based on dosage monitoring by the device, the vaporizer and/or app may report on savings relative to how much the user otherwise smokes.

In some implementations of the current subject matter, the app may also allow a user to log other health related activities, such as from a fitness app, and/or may suggest correlations between nicotine or THC usage and alcohol consumption, heart rate, blood pressure, workout time or weight changes, etc. For example, a user may enter a preferred unit dose (using presets, or estimated/recorded/ programmable data as described above), and a dosage interval or total daily target. The vaporizer and/or app may then lock out after each dosage, and an alert may pop up on a user computing device (e.g., phone, smartwatch, tablet, etc.) when it's time for a next dosage, and the vaporizer automatically unlocks for this next dosage. This could be used as a user-elected reduction approach (step-down or cessation), or to maintain a prescribed therapeutic regimen (e.g., X mg of agent every Y hours, not to exceed Z mg/day).

In some embodiments, the vaporizer and/or an affiliated app may have a dashboard style user-interface, in which users can log on and tabulate their progress over time. Data may be some based on individual and/or group data. For example, the group data can show as a population of what the mean smoking-vaping switch rate is at any given time since starting to use a vaporizer. The apparatus may provide a view in which the user can select other users to define a group (cohort) based on their starting conditions: e.g., packs per day, age, gender, etc.

USER PREFERENCES. In some embodiments, the vaporizer and/or an affiliated app may be customized based on user preferences, and may provide reminders (including for recreational users, including THC users). For example, in some embodiments, the apparatus may save preferences for cartridges (e.g., "pods") of different strains and strength that may be preferred by the user. The app and/or vaporizer may save preferences for different use cases (e.g. 'going for a hike', 'bedtime', 'party time', etc.). In some embodiments, in which cartridges come with different THC/CBD ratios, the apparatus (e.g., vaporizer and/or app) may set a reminder of using high or low THC cartridges based on user usage pattern and preferences.

In conjunction with cartridge sensing (as described above, and see FIG. 14E), in any of the embodiments described herein, the vaporizer and/or app may also or alternatively suggest one or more use profiles (e.g., heating profiles). For example, based on the type of cartridge and/or based on user input on the type of vaporizable material (strain, concentration, etc.) even in embodiments not including cartridge detection, the vaporizer and/or app may suggest a use profile (e.g., "Other users enjoy this strain with profile X", or "Other users enjoy this strain at an initial temperature of 155° C.").

DEVICE CONTROL AND CUSTOMIZATION. As mentioned above, the vaporizer may be controlled in part by user input to an affiliated app. For example, particular aspects of the vaporizer that may be controlled may include changing a temperature set-point, for example to allows users to get less vapor if they need to be less conspicuous. This may also allow the user to reduce harshness and active ingredient consumption per puff.

The app may also provide a more precise indication of battery level beyond what is displayed on the vaporizer. For example, during charging, the app may indicate time remaining.

As mentioned above, the app may also provide firmware updates to the vaporizer.

For a device that accepts both nicotine and THC cartridges, the affiliated (connected) app may also allow the user to switch between nicotine and THC modes, which may likely have different temperature set points.

A vaporizer and/or a device that is part of a vaporizer system may use received signal strength indicator (rssi) to help a user locate a lost vaporizer. In addition, the app may allow the user to cause the vaporizer to vibrate, flash and/or emit sound(s) as an alarm, including for helping to locate a misplaced apparatus. For example, a temperature change, vibration or flash lights may also be the indicator of whether the vaporizer is hiding nearby. In some embodiments, the vaporizer may also help locate a misplaced phone when connected via changing LED colors depending on the distance between the vaporizer and the phone.

A vaporizer and/or an app may be used to adjust LED brightness and color of the vaporizer. For example, for vaporizers with multiple LEDs, a user may download personalized indicator patterns to the device. In addition to making the vaporizer feel more personalized, this may have enhanced utility as it may make it easy to identify which vaporizer belongs to a particular owner.

Figure 21C:
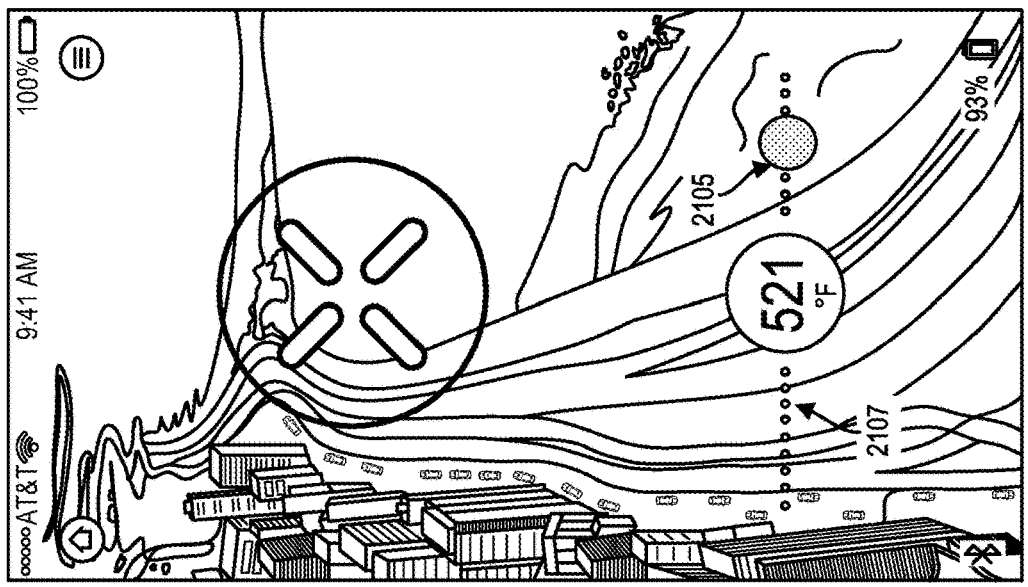
FIGS. 21A-21C illustrate features of exemplary user interfaces for use in controlling, setting, programming, etc. a temperature of a vaporizer using an application consistent with implementations of the current subject matter.
Figure 21B:
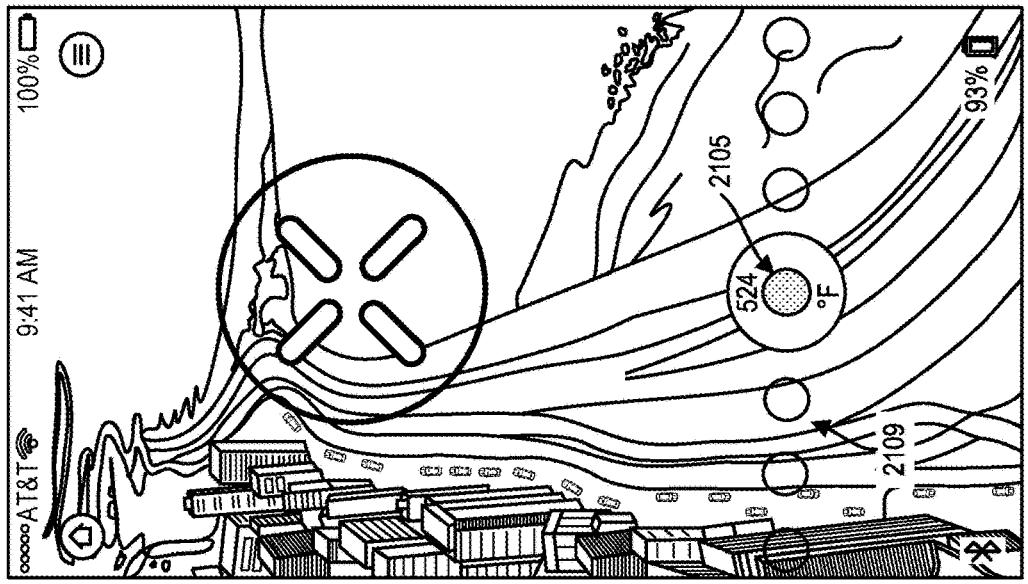
Figure 21A:
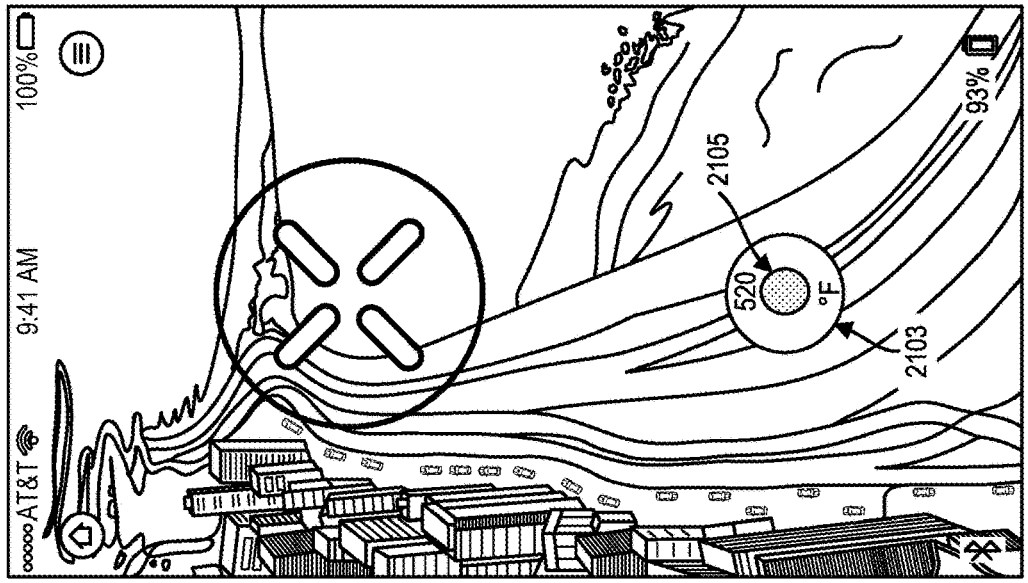

In some embodiments, the temperature of the vaporizer may be adjusted by using a graphical user interface that allows both gross and precise control of the vaporizer temperature with a single finger. For example, as shown in FIG. 21A, a graphical user interface (GUI) may include a display of the temperature (e.g., as part of an indicator 2103) visually indicating the current temperature and/or target temperature of the vaporizer; this temperature may be adjusted up or down (within a range). In this example, to adjust the temperature, the user may hold a fingertip in a location 2105 on or against the indicator 2103, causing indicators 2109 to appear on either side of the temperature when the vaporizing temperature may be adjusted up (on right side) or down (on left side), as shown in FIG. 21B. Quickly sliding a finger over the adjacent indicators 2109 may rapidly move the temperature setting in large intervals (e.g., by 3 degree, 5 degree, 10 degree, 15 degree, 20 degrees, 25 degrees, 30 degrees, 35 degrees, etc., intervals). Large interval adjustment is indicated by the large circles. Holding a fingertip on the temperature indicator (shown as location 2105 in FIGS. 21A and 21B) or adjacent indicators for a predetermined longer period of time (e.g., 1 second, 2 seconds, 3 seconds, 4 second, 5 seconds, etc.) may open a fine temperature control, as shown in FIG. 21C by the smaller indicators 2107; moving the figure along the fine temperature control may allow increasing/decreasing the selected temperature by fine amounts (e.g., 0.1 degrees, 0.5 degrees, 1 degree, 2 degrees, etc.). The temperature change is shown in the central temperature indicator.

SELF-CLEANING. A vaporizer may be configured to include a self-cleaning mode, in which the vaporizer is configured to operate the heater at a predetermined high temperature (e.g., $>=600°$ F.) for a self-cleaning time (e.g., greater than 1 min, greater than 2 min, greater than 3 min, greater than 4 min, greater than 5 min, greater than 6 min, greater than 7 min, greater than 8 min, greater than 9 min, greater than 10 min, greater than 12 min, greater than 15 min, etc.; or between 1 min and 20 min, between 1 min and 15 min, between 1 min and 10 min, etc.). The self-cleaning mode may be operated directly by the vaporizer, or it may be operated in conjunction with an application (app) or the like.

A self-cleaning mode may be operated in conjunction with an accelerometer or other sensor(s) of a vaporizer. For example, the accelerometer may be used to determine if the vaporizer is not held or carried by the user before entering the self-cleaning operation. For example, self-cleaning may be permitted only when the device has been "still" (e.g., set or held on a resting surface) for a predetermined time period, such as 30 seconds, 1 min, 1.5 min, 2 min, 2.5 min, 3 min, etc. The self-cleaning mode may also only be permitted in embodiments (such as shown in FIGS. 2A-2C) having an oven or heating chamber door when the door is secured over the device.

The self-cleaning mode may also be terminated, and the device allowed to cool if the device is picked up or moved (e.g., based on accelerometer input). During self-cleaning, the device may provide a visual, audible or tactile output indicating that self-cleaning is underway. For example, one or more indicators may illuminate or flash (e.g., Red, red and blue, white, etc.) to indicate self-cleaning is operating. In some embodiments, the vaporizer may also or alternatively indicate self-heating by emitting a tone, beep, or whine, or the like.

ANTI-THEFT/PARENTAL LOCK/CHILD-PROOFING. Any of the devices described herein may include a device lock, as mentioned above. For example, the app and or vaporizer may authenticate to a mobile device using encryption, as an anti-counterfeit mechanism. A similar scheme may be used to tie the vaporizer to the owner's mobile communications device (e.g., phone, smartwatch, pad, etc.), such that if stolen the device is disabled to prevent others from using it. In some embodiments, the vaporizer may connect periodically to the mobile communications device to verify.

The vaporizers described herein may also include parental lockout (e.g., child-proofing). For example, a device could be 'locked' for parents who want to make sure their children won't use the device. For parental lockout, in addition to Bluetooth or other relatively long range communications, the apparatus may also implement a near-field communications (NFC) tag on the vaporizer. NFC readers are built into many smartphones. One feature of NFC is that it only works in very short range. This would make unlocking very easy—you just tap the phone against the vaporizer. NFC tags are extremely cheap and small and may be used in addition to, or instead of, other wireless communication modes, such as Bluetooth. NFC could be used to implement some of the other features described above.

GPS FOR LOCATOR, ORDERING, AND SOCIAL NETWORKING. Any of the apparatuses described herein (e.g., vaporizers and/or an affiliated app) may include location services (GPS).

For example, a user buying cartridges for the vaporizer directly from a source may use an app to understand exactly how many cartridges that the user has and how many they have left. A retailer may use this information to offer the user to auto-order more when they are running low.

In any of the apparatuses described herein, the app and/or the vaporizer may include a GPS or may communicate with a GPS to determine location of the vaporizer. Locational information may be used to tell a user the closest retailer to buy more cartridges, to use location service for delivery, to order through a smart phone (e.g., usage tracker combined with auto-refill), and/or to inform the user of relevant local legislation about e-cig and cannabis use.

Locational information may also be used to link a vaporizer to a particular store, for example a store at which the vaporizer is purchased. By associating the purchase with a physical store location or point-of-sale, the store can be offered incentives based on the original purchase and/or subsequent purchases. Additionally, the store can be identified as a preferred store for the user and automatic updates relating to the store can be provided to the user through, for example, use of the app (e.g., special promotions, new devices, new cartridges, and the like). To link the store with the purchased vaporizer, physical beacon devices may be installed at the store (e.g., at the register or at a display). The vaporizer may be configured to listen for beaconing information, and once this information is detected (e.g., at the register when the vaporizer is being purchased), the association of the vaporizer with the store may be made.

Locational information may also be used to disable vaporizers that are determined to be positioned at or located in one or more areas in which vaporizer use is not permitted. For example, particular areas or zones may be established, and if a vaporizer enters such an area, or comes within a predefined range of the area, the vaporizer may be automatically disabled or disabled after an alert is given. Such areas may include, for example, a defined perimeter around schools or within particular locations (such as stores) that do not allow use of vaporizer. Additionally, specific locations in which vaporizer use is not permitted may be set up by one or more individuals (e.g., an individual's house). To establish the areas/zones/locations, physical beacon devices may be installed to identify the areas/zones/locations. When a vaporizer is within range of the beacons, the vaporizer would fail to turn on or would turn off Alternatively, geo-fencing can be used to establish the areas/zones/locations in which use of vaporizers is not permitted. With a vaporizer paired to a user's phone or mobile device, or by utilizing location services of the vaporizer, the vaporizer can be disabled when it is within any of the defined geo-fenced areas/zones/locations.

In addition, any of the vaporizers and apps described herein may be used to enhance the social experience of the user, including for interaction with other users, and communication with a particular user.

In some embodiments, the vaporizer and/or app may profile users and tell them how they compare to others. For example, the vaporizer and/or app may indicate what percentile a user's nicotine/THC consumption fall into and/or may recommend strains (cartridges) based on user behavior (e.g., 'We noticed that you are mostly using your vaporizer at night. Other people who use at night prefer this strain.') .The vaporizer or app may also include access to forums or chat areas where users may trade tips, and areas where physicians can discuss various topics.

In some instances, the vaporizer and/or app may allow forming of communities or groups among vaporizer users.

Through use of the app, users may be presented with an option to join or create one or more groups. Or groups may be created for a particular geographic area. The groups may allow users to vote (e.g., on preferred cartridges or other topics of interest), obtain data or statistics related to a use of certain devices or flavors, and/or data or statistics on a number of overall users in a particular area (such as a given city or zip code). In some instances, certain identifying characteristics of users may be kept anonymous for safety and/or privacy reasons.

In general, any of these apparatuses may permit users to engage in games either by gamification of usage or by including games that may be played by users (including multiple users) unrelated to vaporization of material. For example, gamification of usage (including purchasing of new components such as cartridges) may include awarding points, prizes, etc. and the creation of teams for switching or the like. Games may include the use of the accelerometer or other sensors in the apparatus that may be transmitted wirelessly to an app and/or to another user's vaporizer or app (e.g., directly or via a remote server) to permit game interaction.

The vaporizers and/or apps described herein may also facilitate sponsorships, for example, allowing a user to sign a friend or family member up, pay the cost for a vaporizer, and have it sent to them or even delivered immediately (e.g., by bike messenger). This may be used to provide incentives with sponsors for switching from traditional cigarettes to vaporizers and/or reward use (presumably in place of use of traditional cigarettes), e.g. if you stick with it you get prizes (e.g., gift cards, etc.).

Any of the apparatuses described herein (including the vaporizers and any affiliated apps) may also be used to collect and analyze user data. This may allow the vaporizer producers, providers and retailers to get to know users better, including understand where when and how they are using the vaporizer. Knowing where and when a consumer is using a vaporizer may allow better marketing to users and may improve the design for future products.

The vaporizers and apps described herein may also facilitate communication between the manufacturer and/or retailer and the consumer (user). For example, by interacting with consumers while they are using the product, there may be opportunities to encourage direct sales. Thus, for example an app may say: "If my calculations are correct, it looks like you only have one cartridge left in your pack. Would you like to buy another?"

The vaporizers and apps described herein may also have enhanced anti-counterfeit components, including registration (e.g., through use of the app) of the vaporizer and/or app. In some embodiments, the vaporizer could have a similar encryption handshake with the app and/or the charging dock.

In addition, the vaporizers and/or the app may permit or include device diagnostics. For example, the vaporizer and/or app may monitor component level failures (e.g., pressure sensor, battery, pogo pins, etc.), and may potentially identify a broken device in the field and ship warranty replacement without the need to return a device to customer service. This may also permit the faster collection of data on common problems to be used for rolling changes and future designs. For example, diagnostic information can be collected from various devices and submitted for analysis. The diagnostic and other operational information can be submitted through the app and stored at a central server, thus allowing for such information to be routinely updated without requiring it to be stored on the devices.

Moreover, the vaporizers and/or app may automatically send manufacturing level information (serial number, etc.), which may later be associated with the diagnostic and/or operational information of a particular device. Such information may also be associated with the location in which the device was sold (using the beaconing information as described above, for example). In some instances, the manufacturing level information is sent with the point-of-sale information to create a record for a particular vaporizer. Subsequent diagnostic information may later be added to the record. Additional information may include device lifeline, date of sale, purchase date, each without requiring information from a user. The collected information can be used in a variety of ways, such as future interactions with the user from the store (e.g., facilitating conversation between the store and the user).

Calibration data may be stored on a cartridge used with a vaporizer, transmitted to the vaporizer, and provided (via the app for example to a central sever) for storing and analysis. For example, such information may include strains, concentrations, and the like. The communication between the cartridge and the vaporizer in which it is used allows for suggestions and recommendations, for example, to be provided to the user. For example, the communicated information may be provided and analyzed to determine other types of cartridges that may be of interest (based on, for example, use information collected from other devices or known similarities/effects). The user may then be provided, via the app, with customized suggestions and recommendations.

EXAMPLE

Application Software/Hardware/Firmware ("App")

Examples of application software with many of the features described herein for use with one or more vaporizers are described with reference to FIGS. 7A to 21C. FIGS. 7A-7B show a user interface (UI) for an application (app) that may be used with a vaporizer as described herein, including an initial security control and/or authorization protocol for accessing a vaporizer and/or affiliated vaporizer data analysis, data collection and data processing systems, including the app itself. Any of the security features described above, including biometric and other data, may be incorporated.

FIG. 7A shows part of a security control and/or authorization for accessing a vaporizer and/or affiliated vaporizer data analysis, data collection and data processing systems, including an app. FIG. 7B is an exemplary user interface requesting input of client information to set up an account to be affiliated with a vaporizer.

The user may also customize the application or affiliated software/hardware/firmware. FIG. 7B shown an exemplary UI requesting input of client information to set up an account to be affiliated with a vaporizer.

Figure 8B:
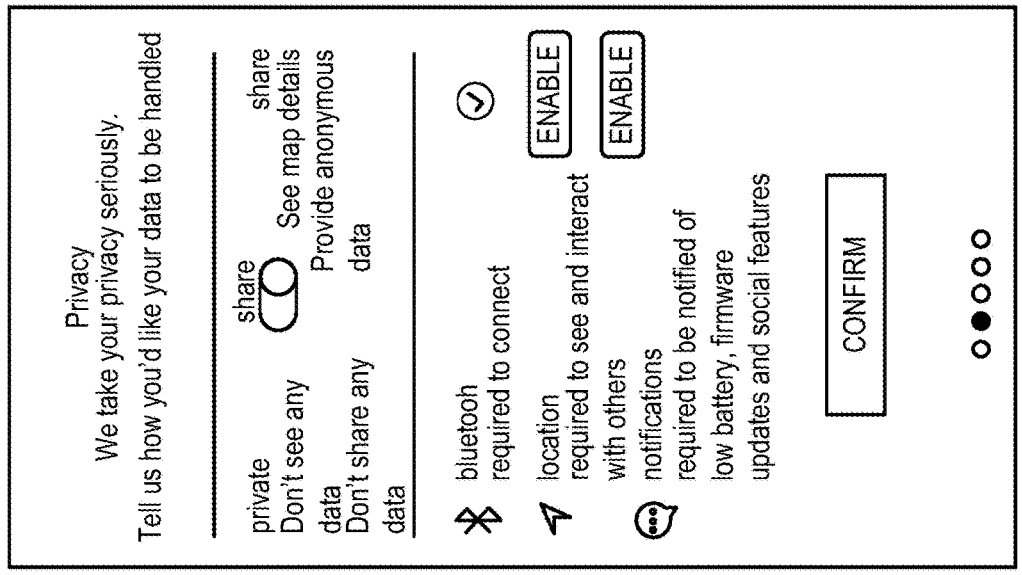
FIGS. 8A-8B illustrate features of exemplary user interfaces for use with a vaporizer or an application affiliated with the vaporizer consistent with implementations of the current subject matter.
Figure 8A:
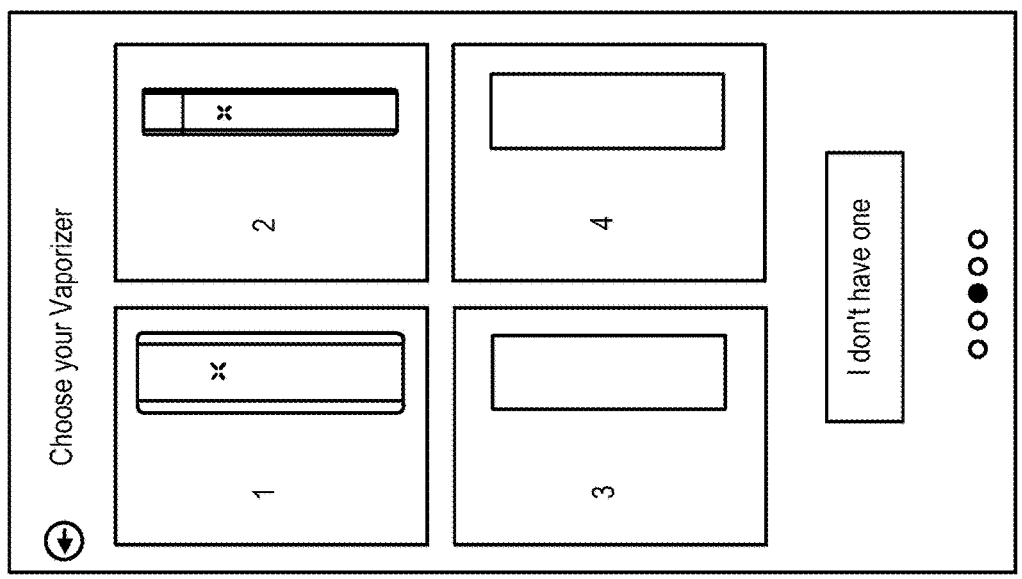

FIGS. 8A-8B illustrate exemplary UIs for use with a vaporizer, or an app affiliated with the vaporizer that may further customize/personalize the UI for the particular user. FIG. 8A illustrates a user interface for an app configured to allow the user to associate one or more vaporizers with the app, and FIG. 8B illustrates a user interface screen for an app that allows the user to control privacy settings.

Figure 9C:
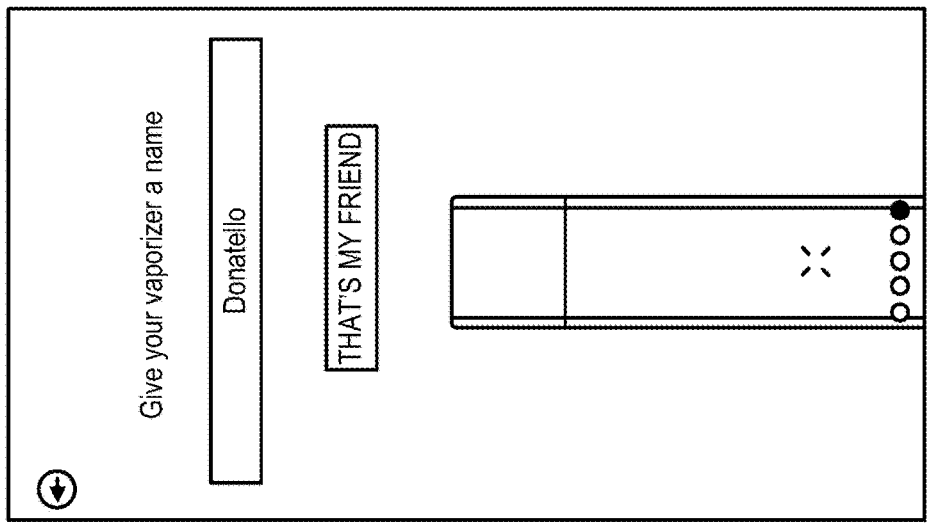
FIGS. 9A-9E illustrate features of exemplary user interfaces for use with a vaporizer that include identification and/or detection of a cartridge for use with the vaporizer consistent with implementations of the current subject matter.
Figure 9B:
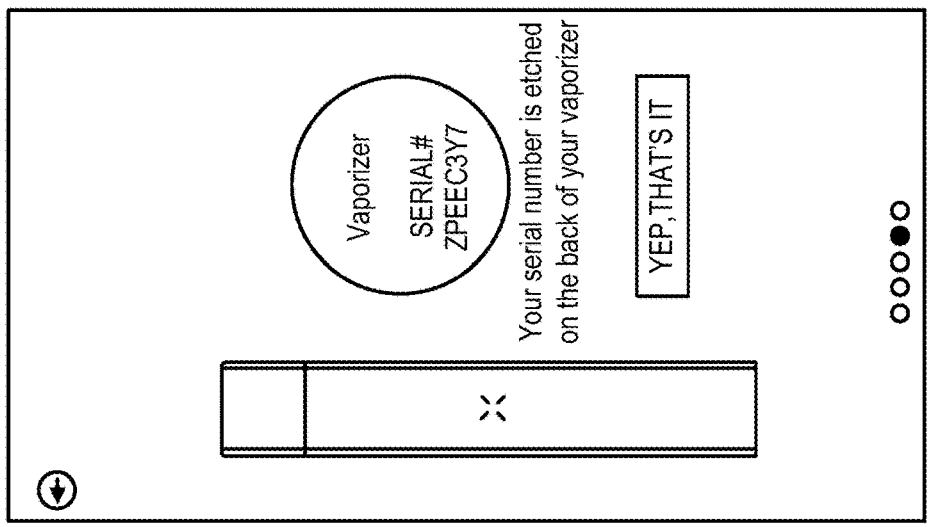
Figure 9A:
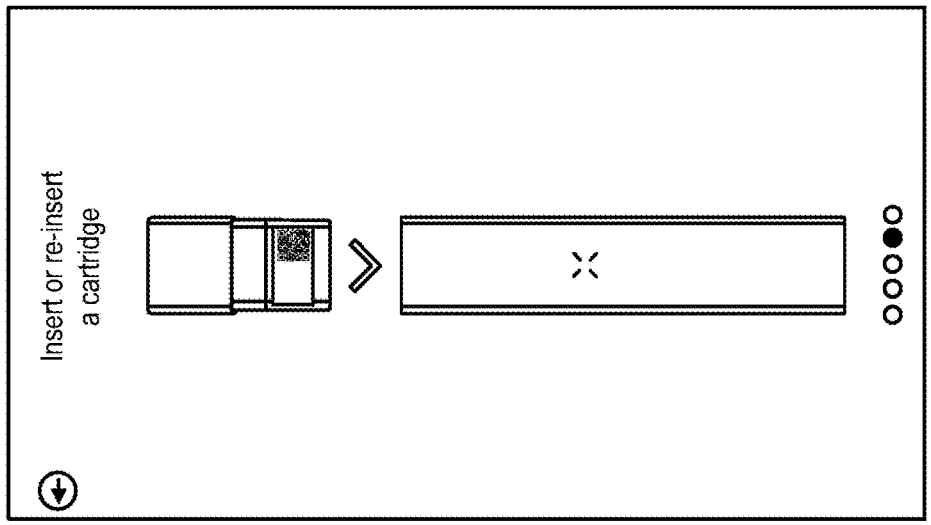
Figure 9E:
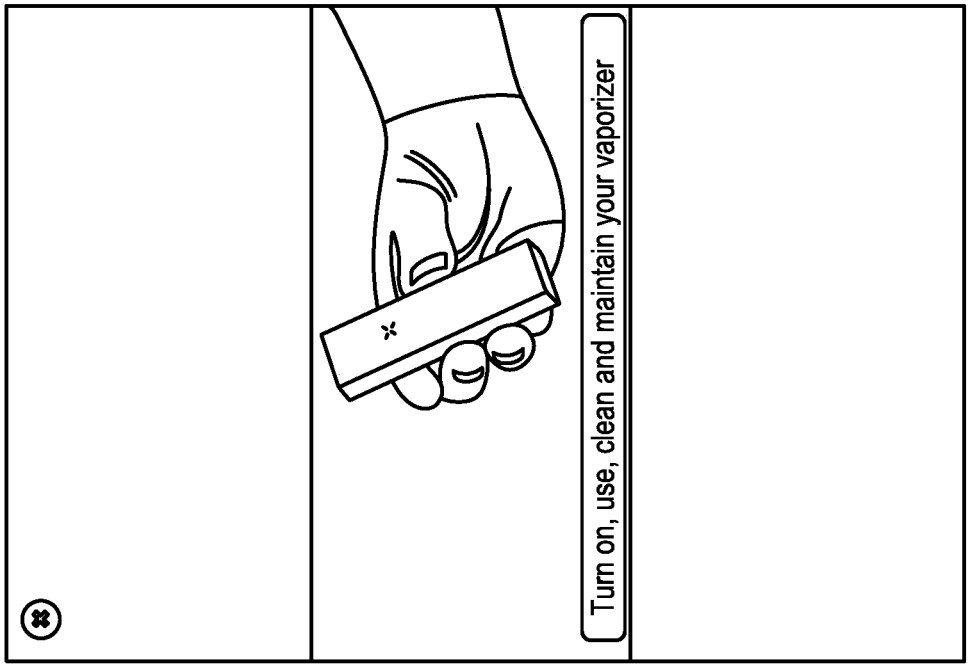
Figure 9D:
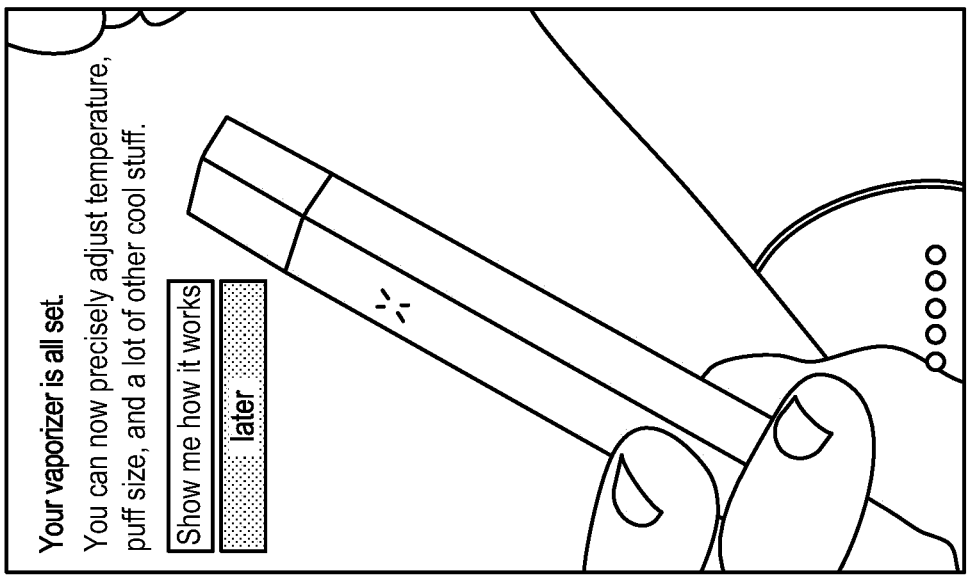

Any of the apps described herein may also be adapted for use with detection, including automatic detection, of the cartridge and/or vaporizable material. The app may provide instructions for detecting/identifying, or the operation of the app may be automatically adjusted/customized based on the detected cartridge. For example, FIGS. 9A-9E illustrate exemplary UIs for use with a vaporizer that include identification and/or detection (including automatic detection) of a cartridge for use with the vaporizer. FIGS. 9A and 9B illustrate user interface screens guiding a user in operation of the vaporizer, including detection (e.g., automatic detection) of the cartridge. FIG. 9C is a UI configured to allow the user to customize one or more of the vaporizers associated with the user account, including providing names (e.g., nicknames) to the one or more vaporizers. FIG. 9D illustrates a UI providing the option of instruction, by showing movies, diagrams, or the like, to guide the user through operation of the vaporizer, including operation of the vaporizer and app together, as shown in the exemplary UI of FIG. 9E ("how to"), illustrating animated instructions for use.

Figure 10:
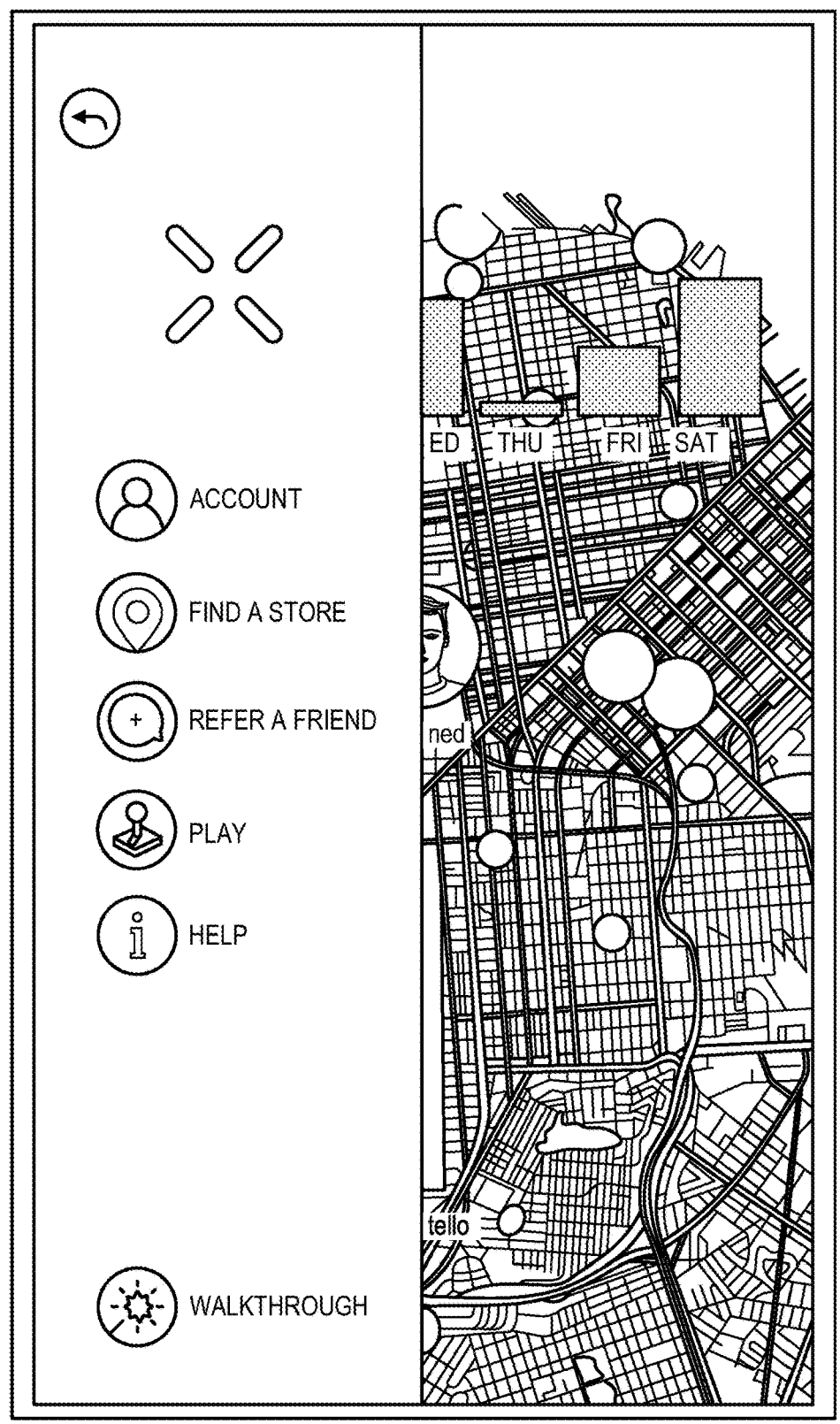
FIG. 10 illustrate features of an exemplary user interface for an application for use with a vaporizer including a menu of commands consistent with implementations of the current subject matter.

FIG. 10 is another example of a UI for an app including a menu of commands (including "account", "find a store", "refer a friend", "Play", "Help", and "walkthrough"). The UI for the menu of commands may be presented on demand on top of other UIs, including statistical/data displays (e.g., dose information, use information, etc.), as shown.

Figure 11A:
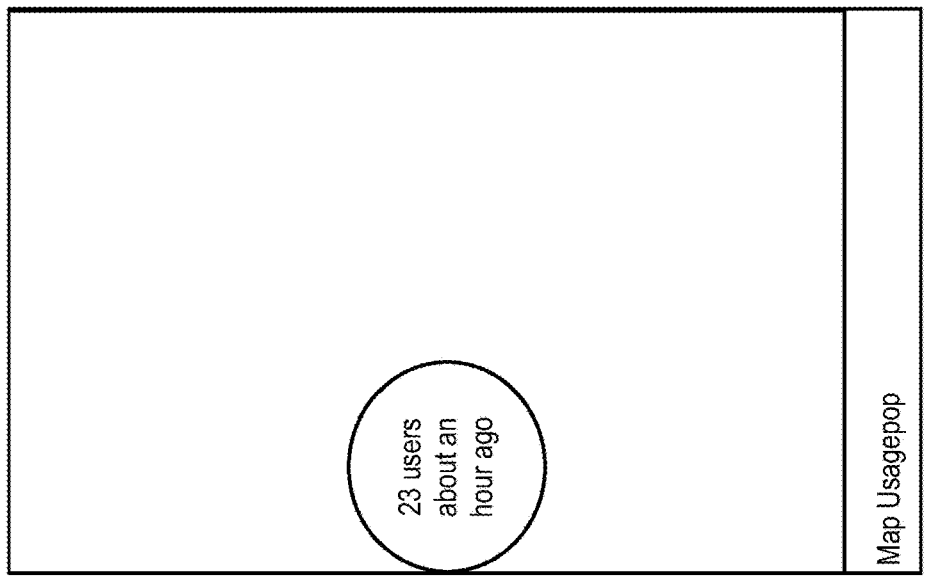
FIGS. 11A-11C illustrate features of exemplary user interface screens that may be used as part of an application interface consistent with implementations of the current subject matter.
Figure 11B:
Figure 11C:
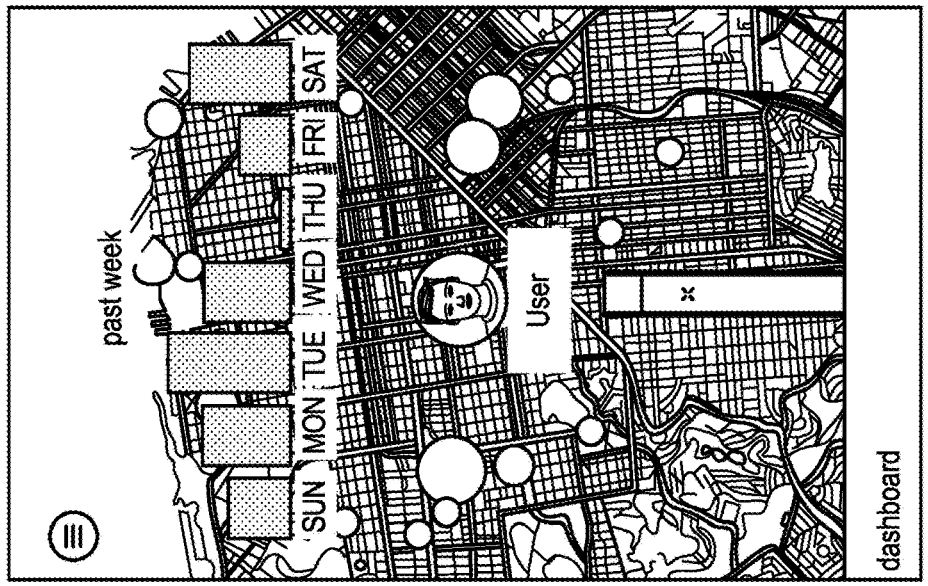

FIGS. 11A-11C illustrate UI screens that may be used as part of the app interface (e.g., for a handheld/wearable apparatus).

In FIG. 11A, the UI includes a user name/image, and statistical data (bar graph at top) of use information ("dashboard" information). FIG. 11B shows a map indicating user location (e.g., by accessing GPS information and/or user-indicated information); FIG. 11C illustrates an information icon that may be placed onto a Map screen showing information about other vaporizer users/groups.

Figure 12:
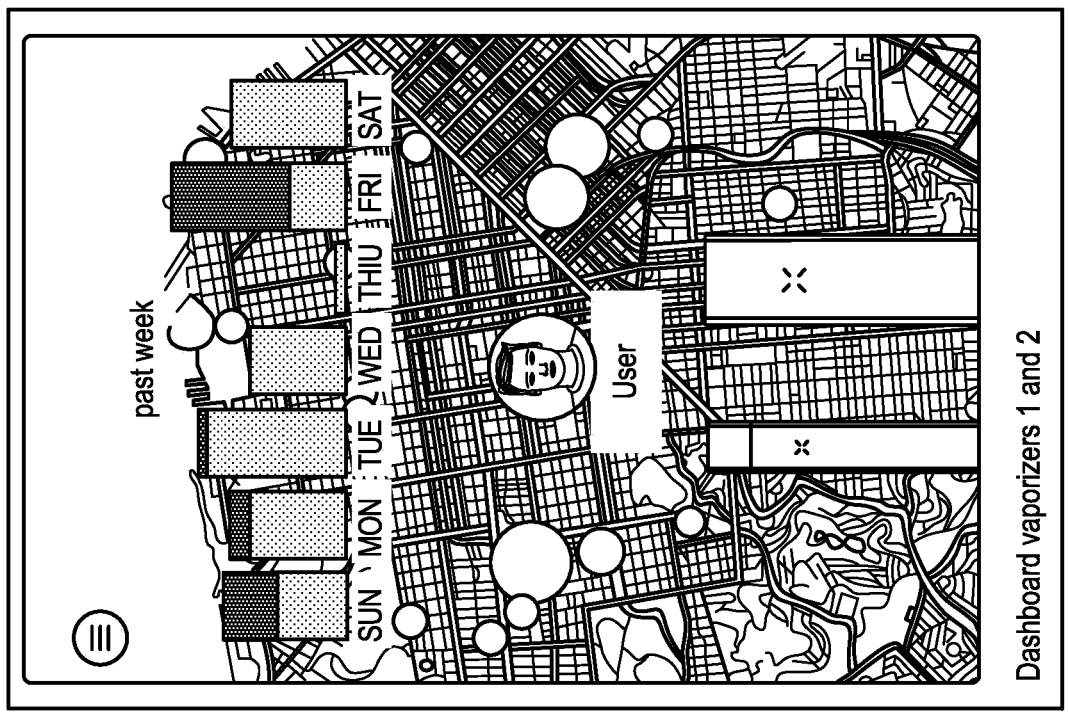
FIG. 12 illustrate features of an exemplary user interface showing a user information dashboard consistent with implementations of the current subject matter.

FIG. 12 is a UI showing a user information ("dashboard"), including graphical illustrations of the user and associated vaporizer devices.

Figure 13A:
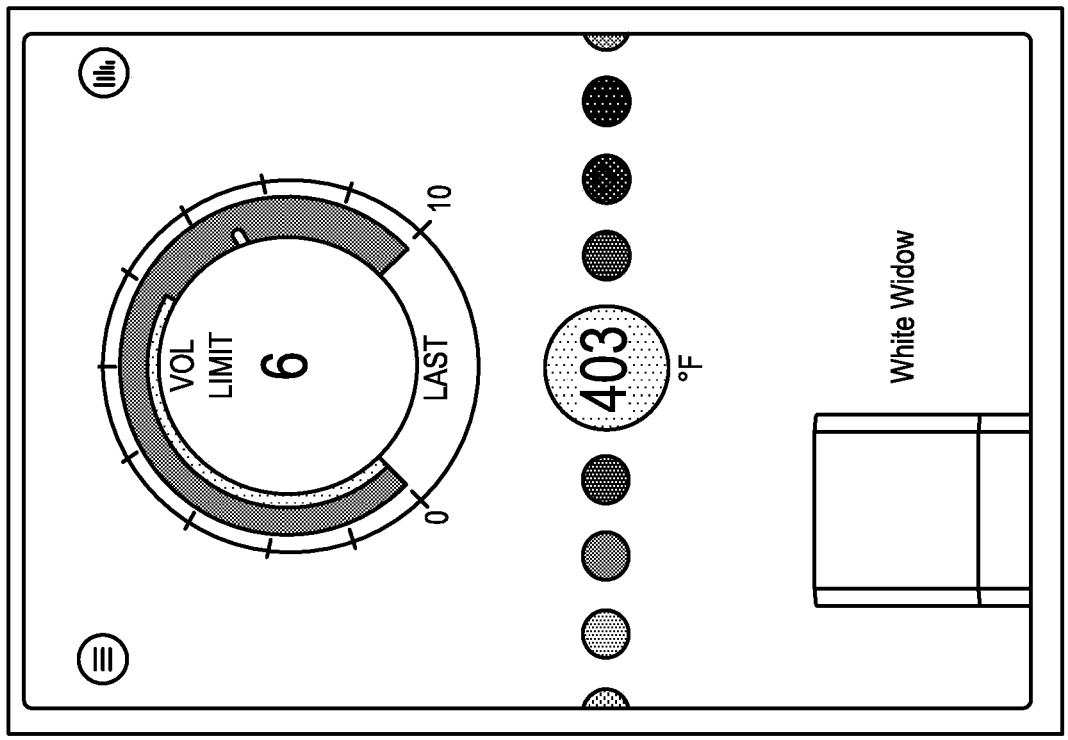
FIGS. 13A-13C illustrate features of exemplary user interfaces for controlling operation of an associated vaporizer consistent with implementations of the current subject matter.
Figure 13C:
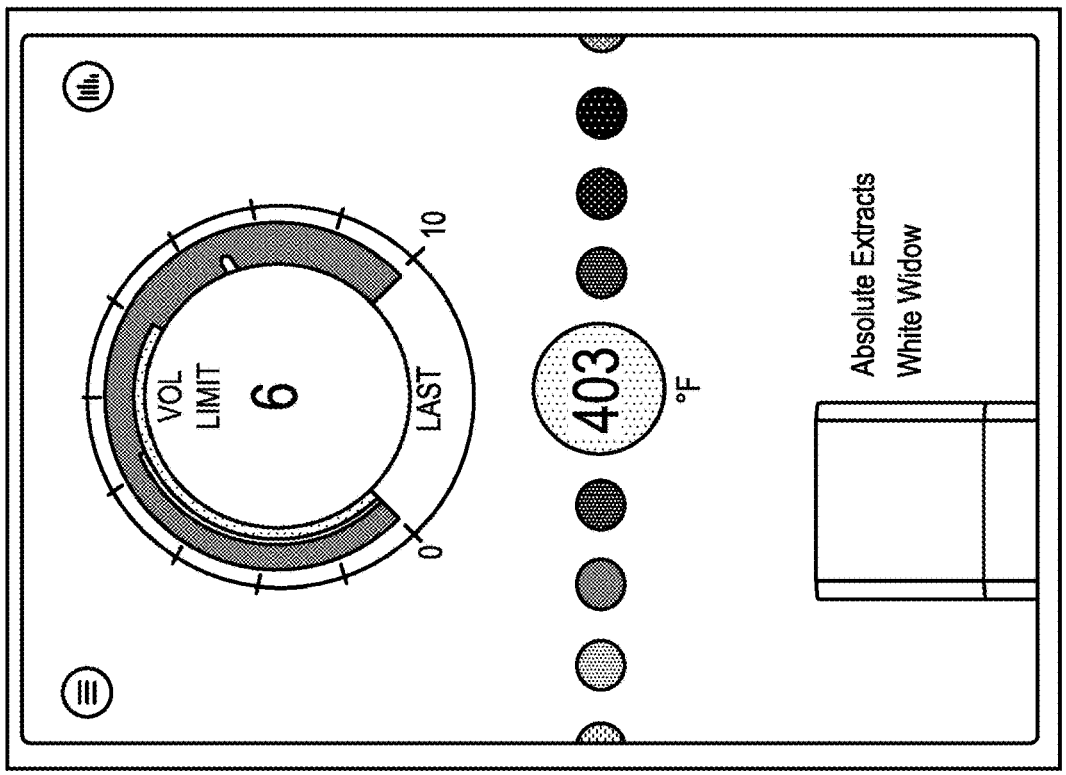
Figure 13B:
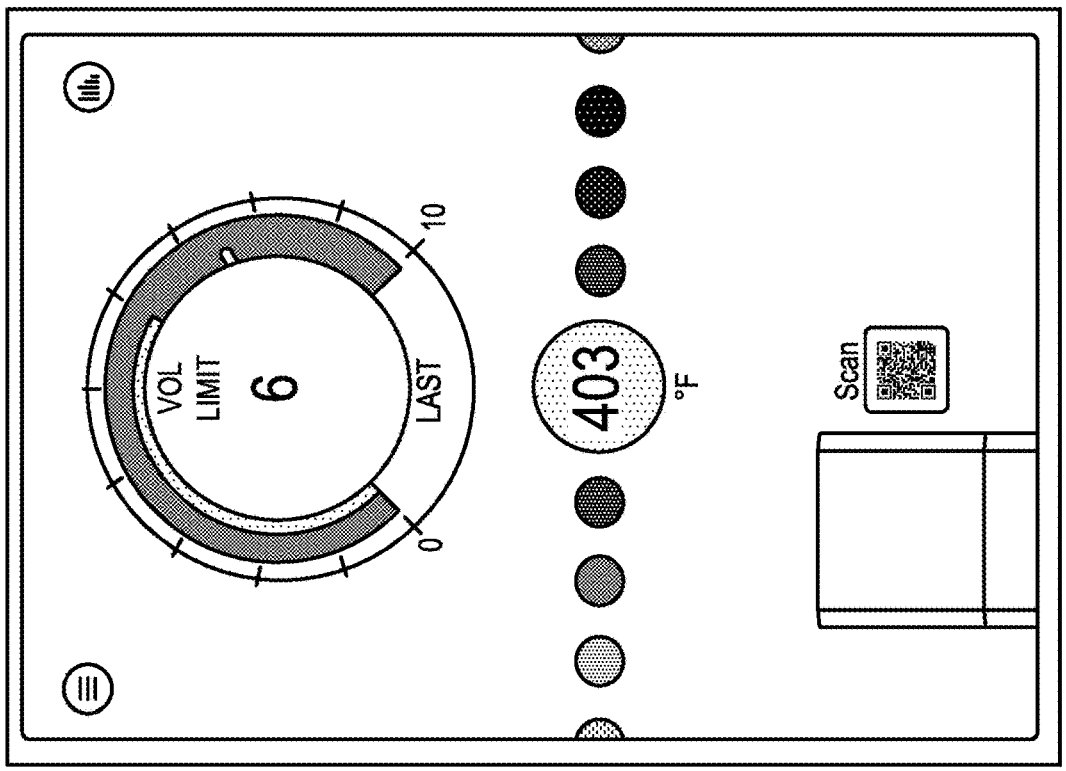

FIG. 13A is a UI for controlling operation of one of the associated vaporizers, showing a detected cartridge on the bottom, with information about the cartridge and/or contents that may be accessed by selecting/touching the image, a central temperature (e.g., oven/vaporization chamber) control allowing finger-tip selection and/or modification of temperature manually, or selection of one or more "programs" for setting temperature, and a monitor indicating the number of inhalations and/or doses taken from the vaporizer, either cumulatively for a 'session' or within a set time period. FIGS. 13B-13C illustrate alternative UIs or modified UI similar to that shown in FIG. 13A. As shown, in FIGS. 13A-13C, an indicator (e.g., a heart or other symbol) may be used to show a pre-set preference for the user.

Figure 14C:
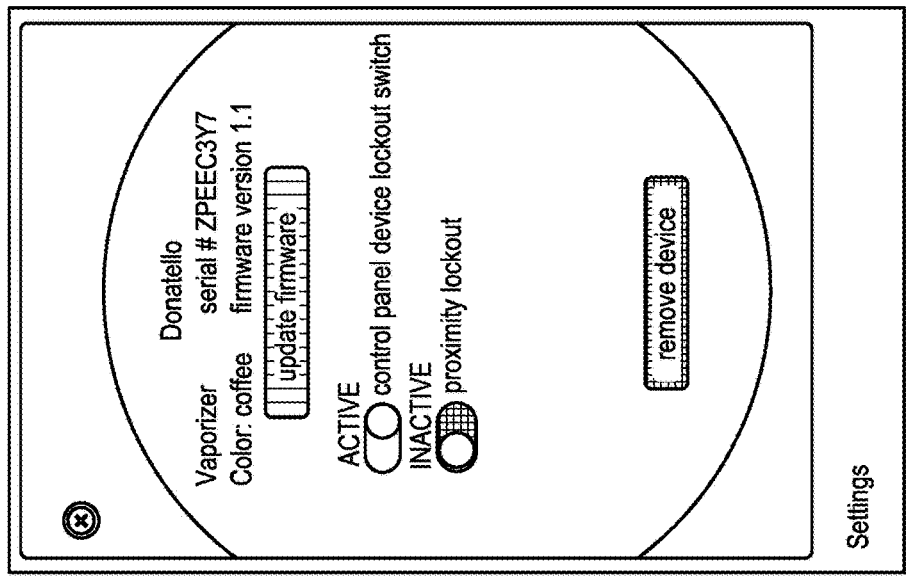
FIGS. 14A-14E illustrate features of exemplary user interface alerts/pop-ups that may be used consistent with implementations of the current subject matter.
Figure 14B:
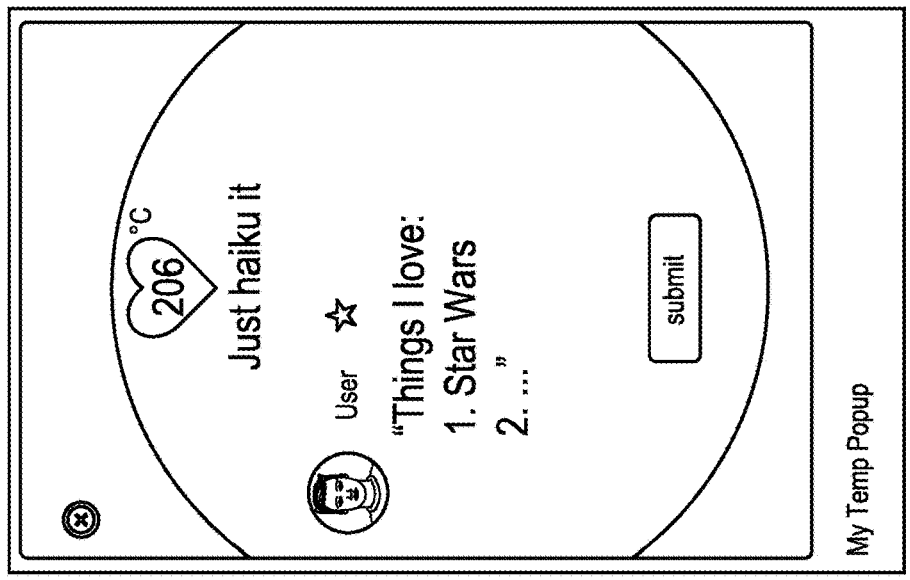
Figure 14A:
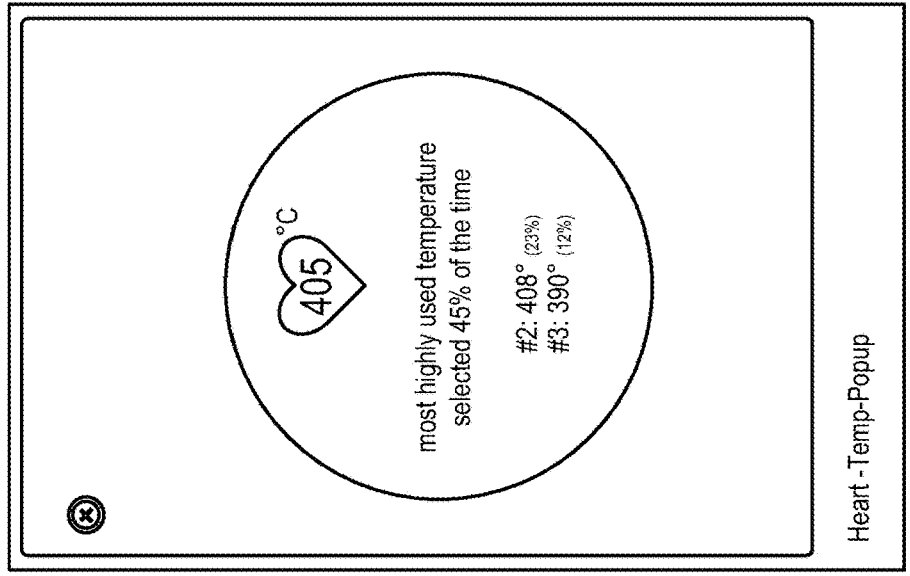
Figure 14E:
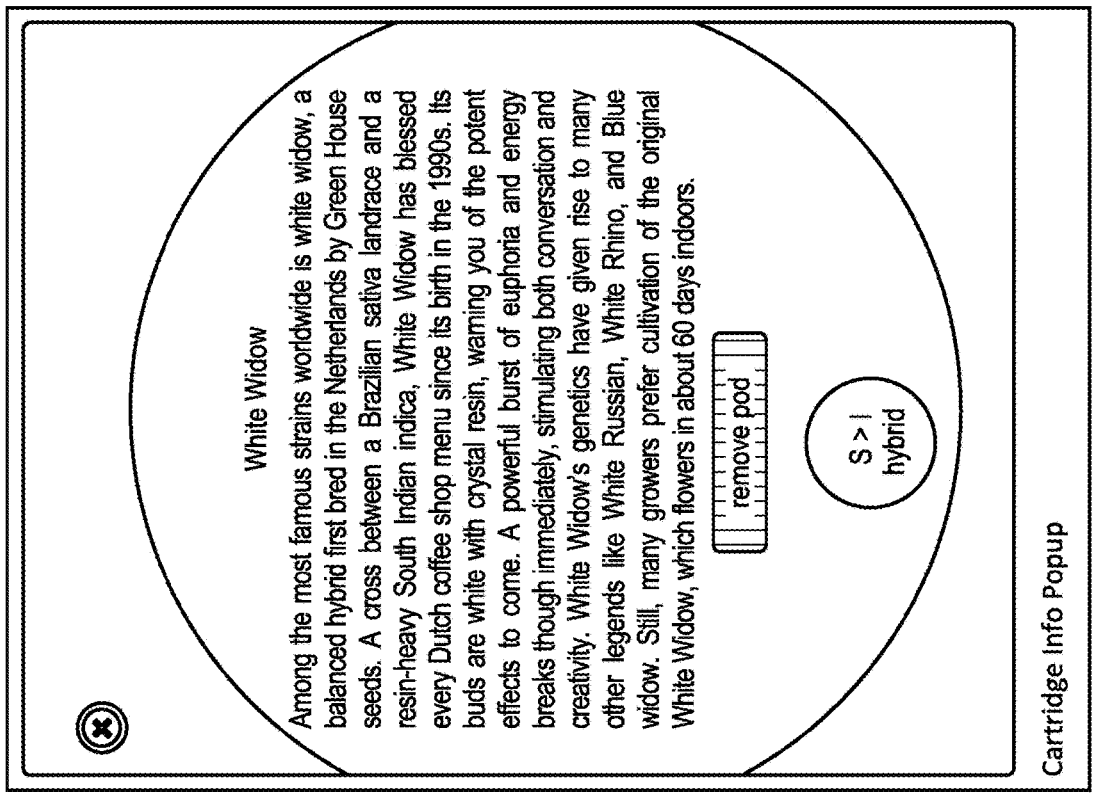
Figure 14D:
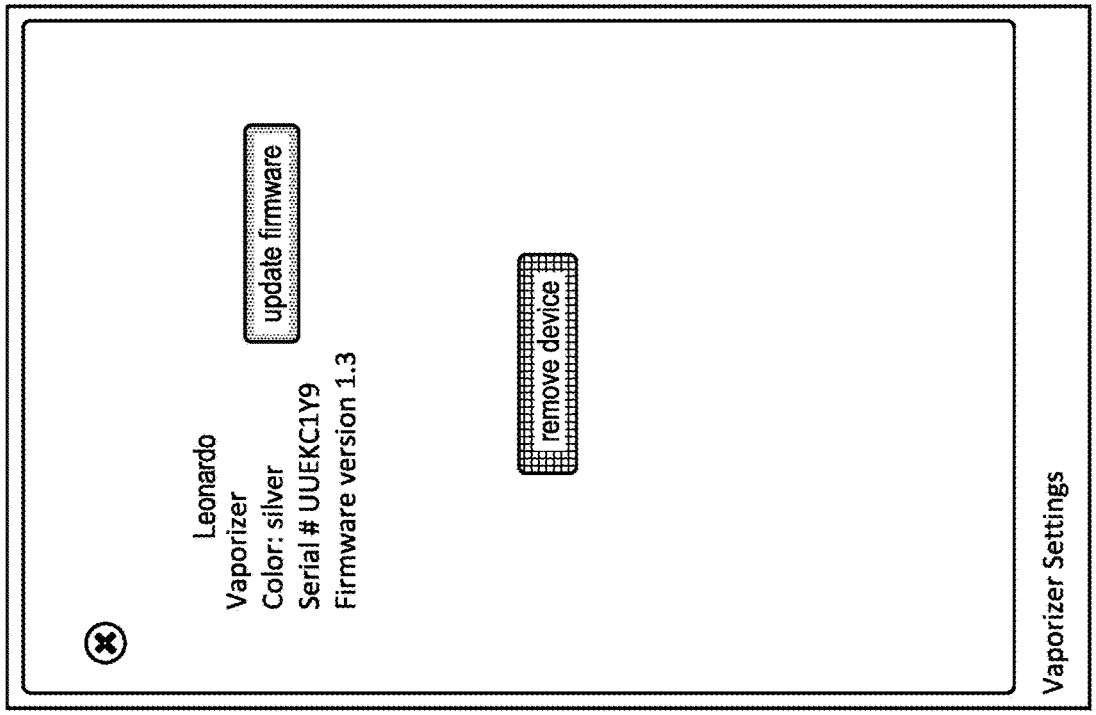

FIGS. 14A-14E illustrate UI alerts/pop-ups that may be used. FIG. 14A shows a user alert/pop-up that may indicate information about the operation of the vaporizer and/or a specific cartridge based on aggregate data from other users. FIG. 14B illustrates user-customized data that may be used. FIG. 14C illustrates user-specific settings for operation of the vaporizer and/or app, including downloaded updates to the firmware of the vaporizer via the app, similar to the UI in FIG. 14D. FIG. 14E illustrates an alert/pop-up specific to an inserted and detected cartridge referencing information about the vaporizable material.

Figure 15B:
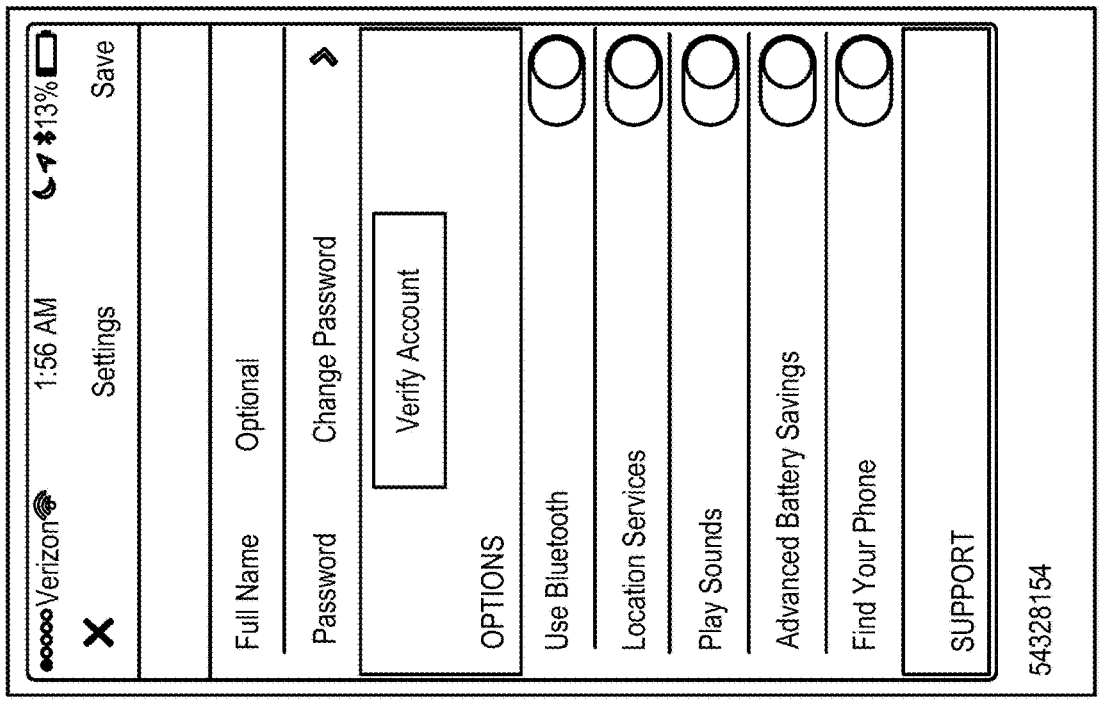
FIG. 15B illustrate features of another exemplary user interface for customizing the application and/or vaporizer consistent with implementations of the current subject matter.
Figure 15A:
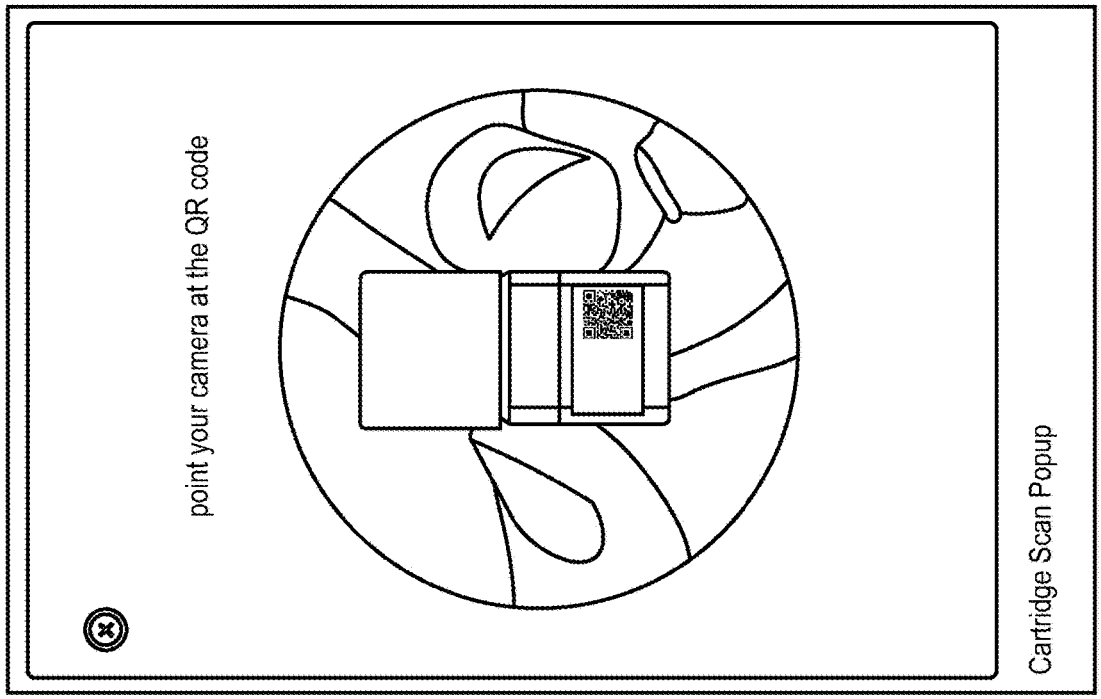
FIG. 15A illustrates features of an exemplary user interface for assisting a user in implementing a detection/determination of a cartridge consistent with implementations of the current subject matter.

FIG. 15A illustrates one method (and UI for assisting a user in implementing it) for detecting/determining a cartridge, using a QR code present on the cartridge, which may be scanned by a user electronic device (e.g., smartphone) in communication with the apparatus. FIG. 15B is another UI for customizing the app and/or vaporizer, showing options for control of the wireless communication (e.g., Bluetooth) and other features.

Figure 16C:
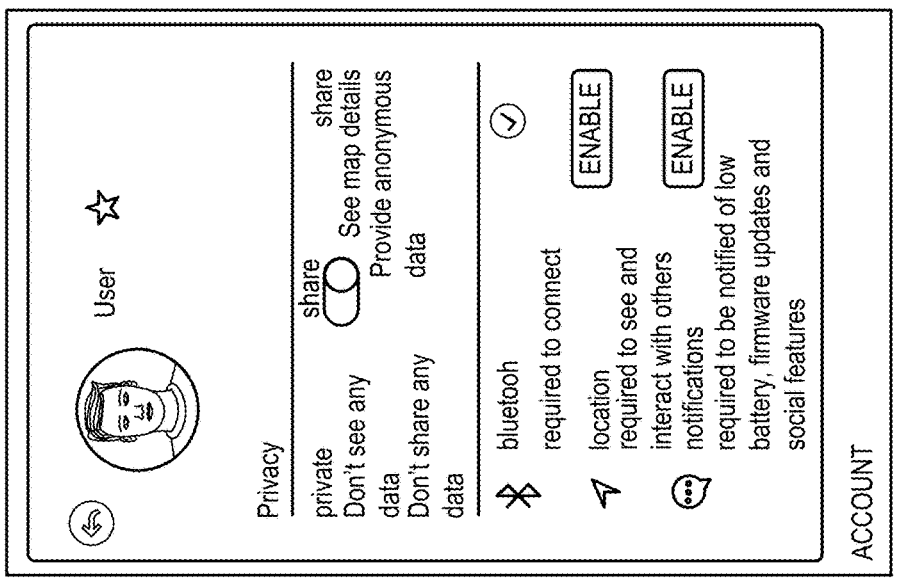
FIGS. 16A-16E illustrate features of exemplary user interfaces including a menu of commands and accessory user interfaces associated with each command/control consistent with implementations of the current subject matter.
Figure 16B:
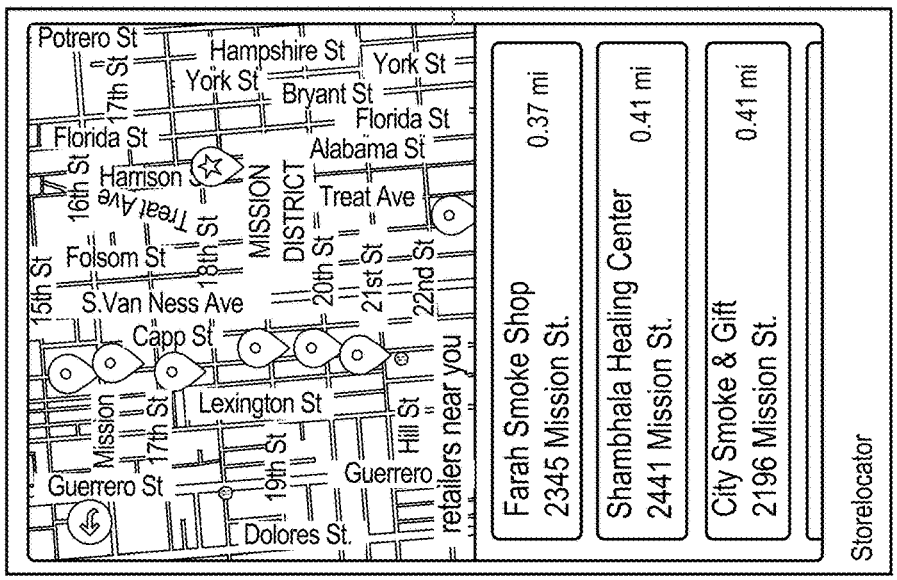
Figure 16A:
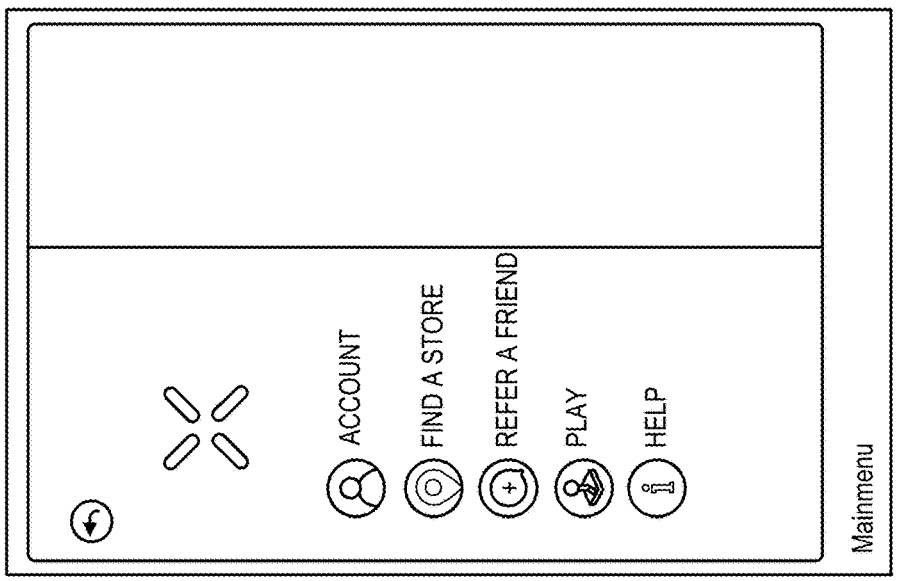
Figure 16E:
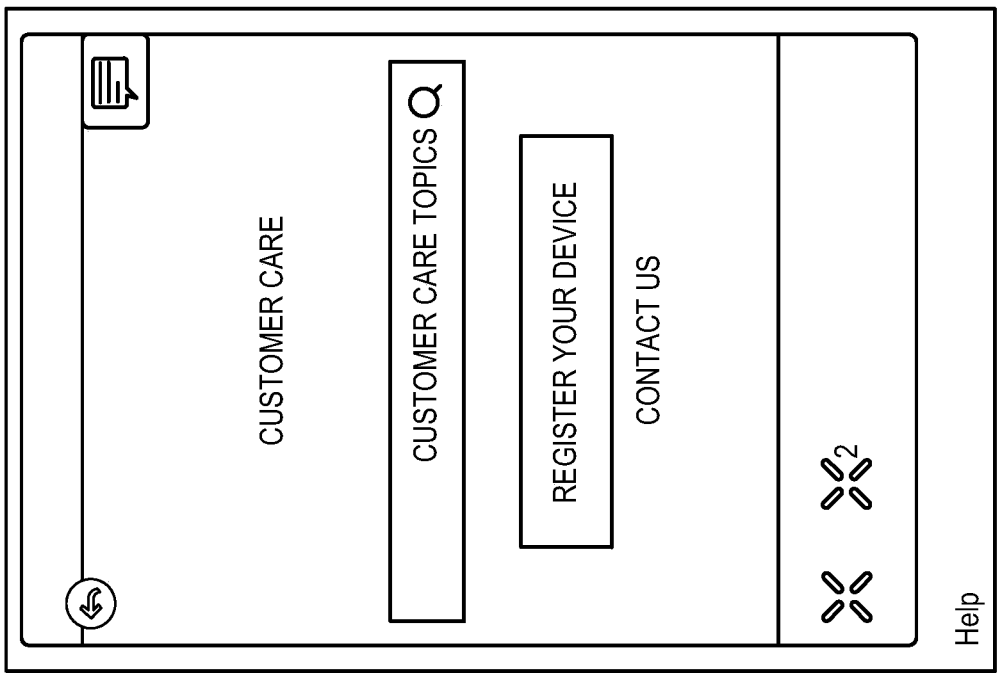
Figure 16D:
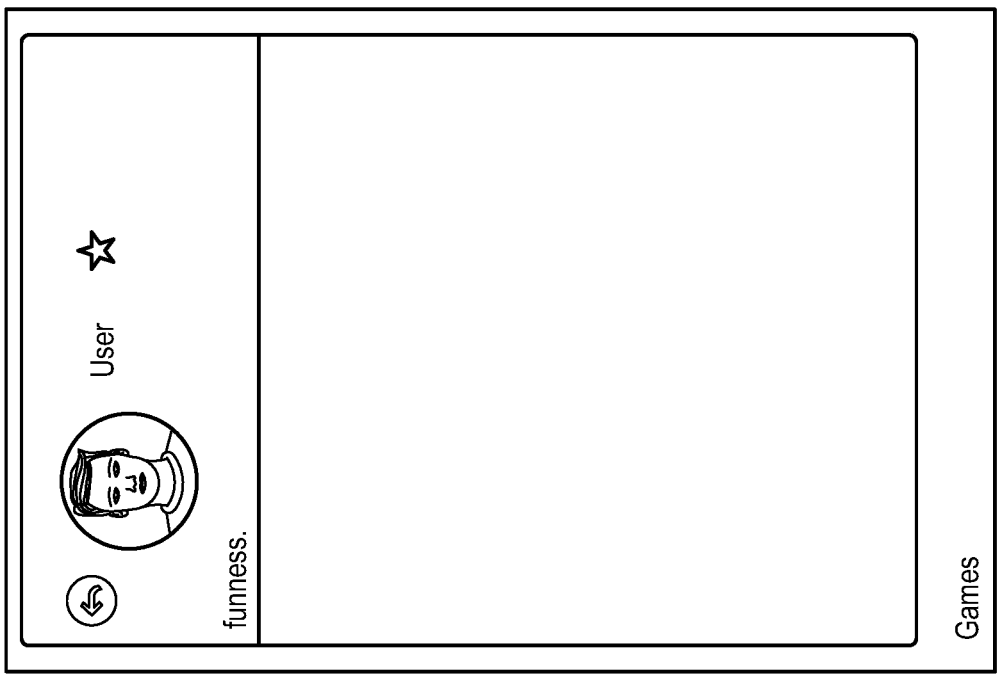

FIGS. 16A-16E illustrates a UI including a menu of commands (such as the one shown in FIG. 10), shown in FIG. 16A and accessory UIs associated with each command/control, shown in FIGS. 16B ("store locator"), 16C ("account"), 16D ("games"), 16E ("help"). Additional UIs and content may be provided or linked through these UIs.

Figure 17B:
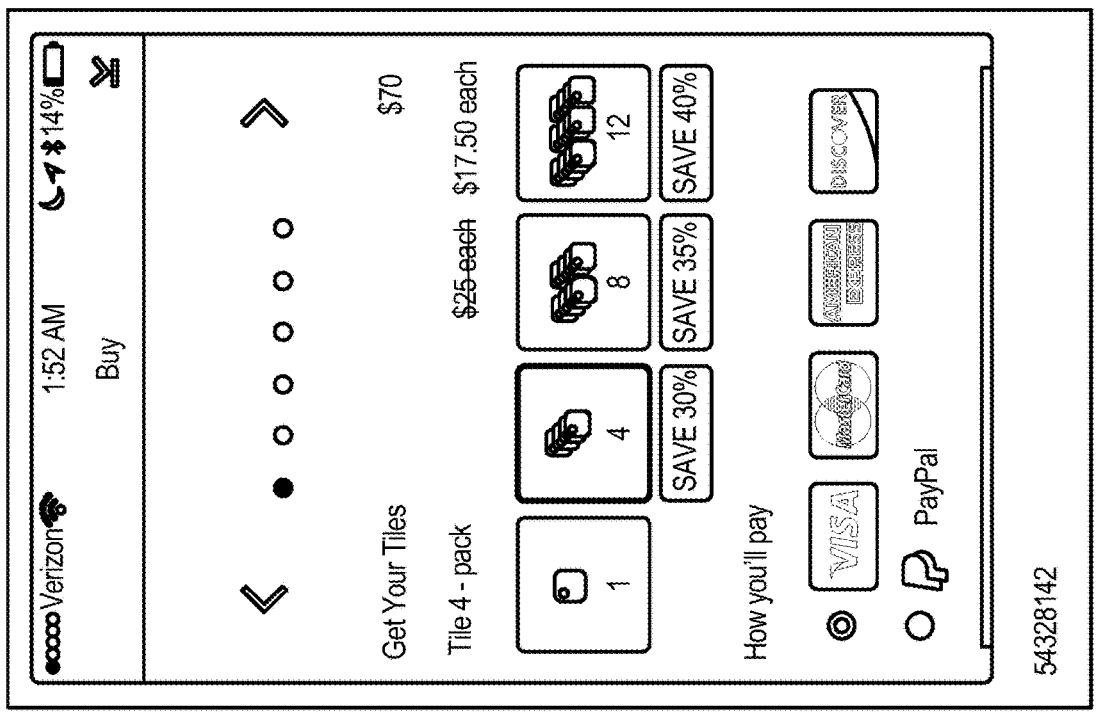
FIGS. 17A-17B illustrate features of exemplary user interfaces that may be presented by an application consistent with implementations of the current subject matter.
Figure 17A:
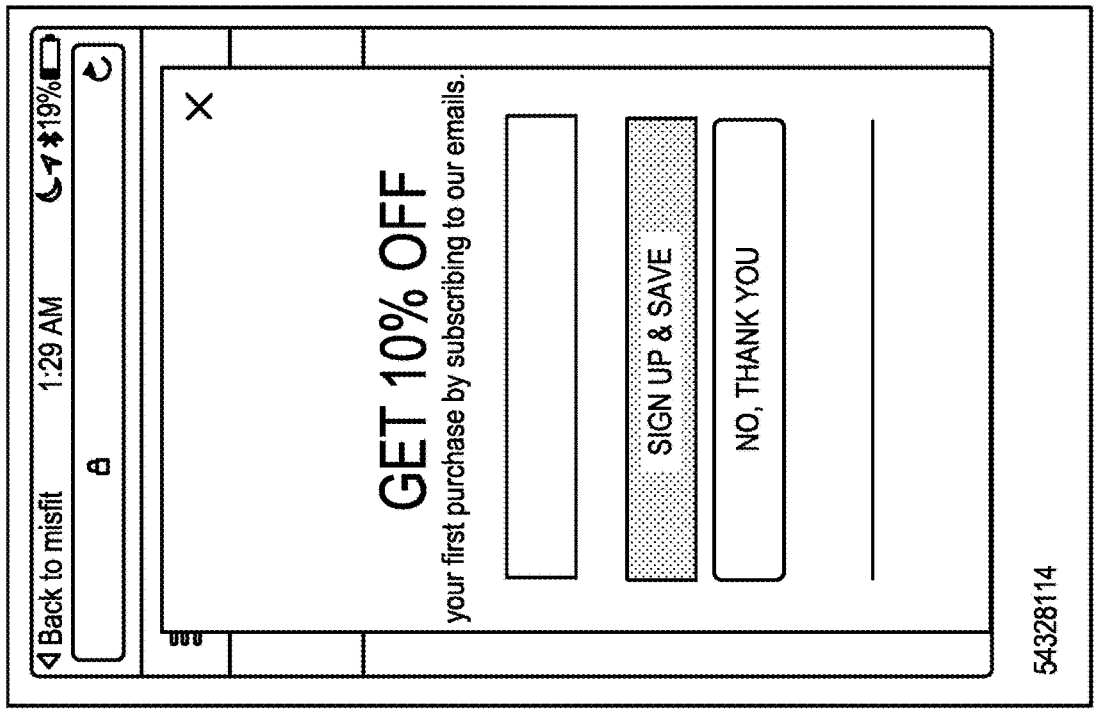
Figure 18E:
Figure 18D:
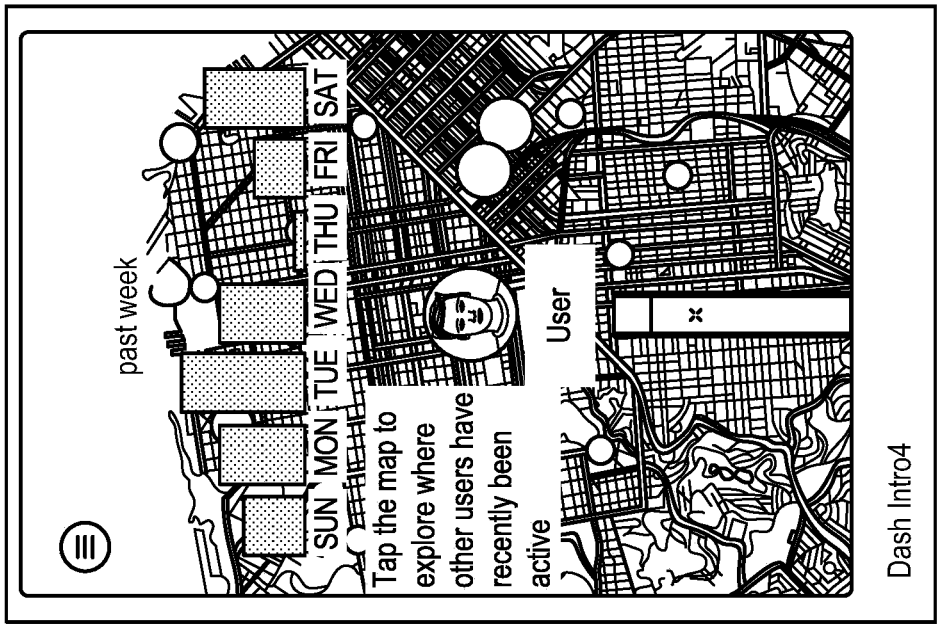

FIGS. 17A-17B illustrate UIs that may be presented by an app including coupons or ads (FIG. 17A) and purchase/reordering UIs (FIG. 17B).

FIGS. 18A-18E illustrate UIs that may be used to guide a user through the operation of the vaporizer and/or app, including describing/illustrating features of either or both.

Figure 19C:
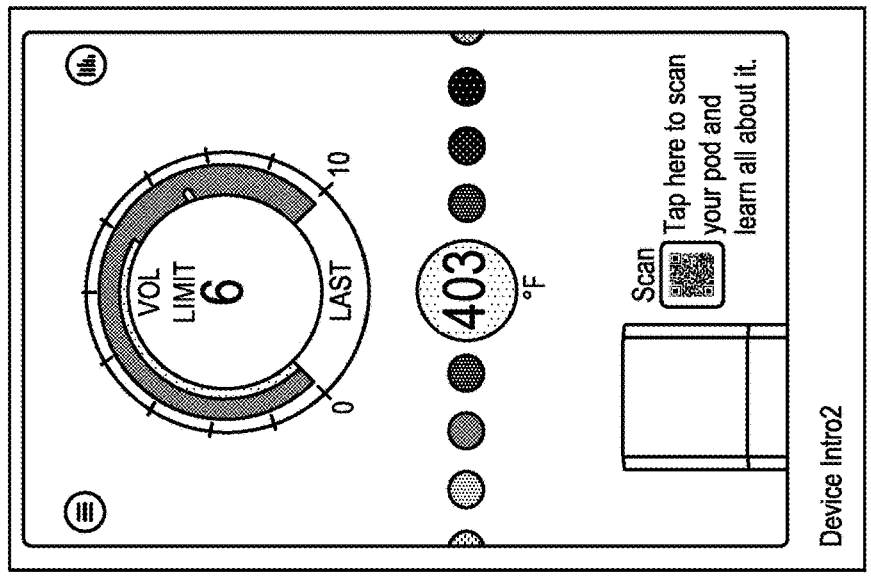
FIGS. 19A-19F illustrate features of exemplary user interfaces that may be used to instruct a user on controlling the vaporizer using an application consistent with implementations of the current subject matter.
Figure 19B:
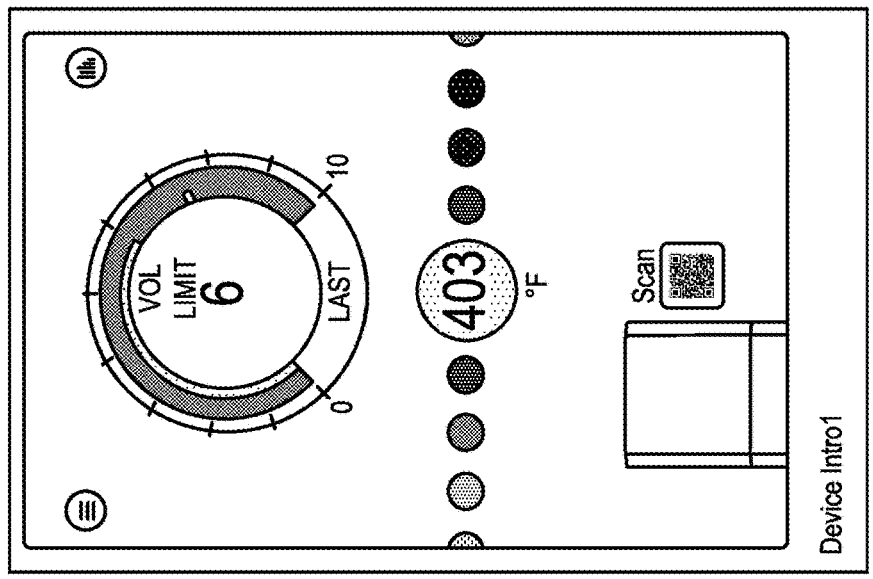
Figure 19A:
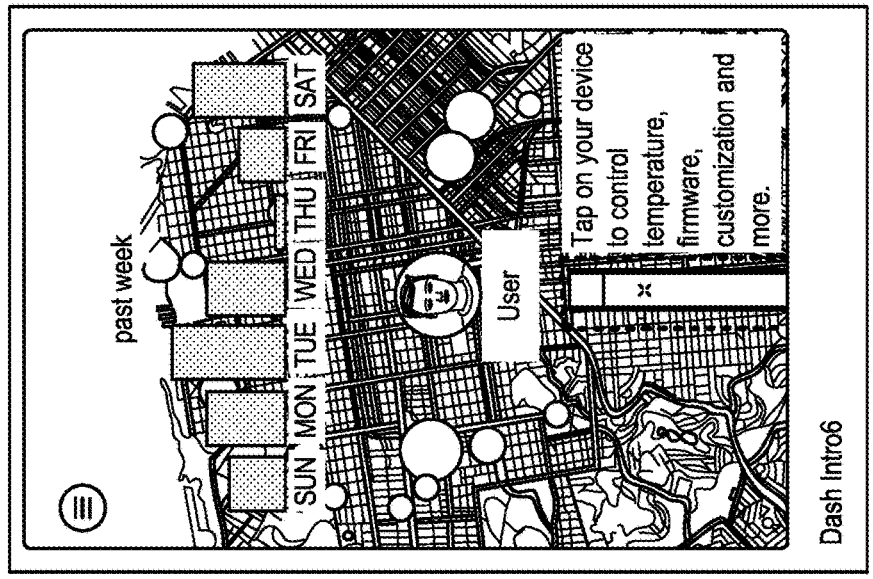
Figure 19E:
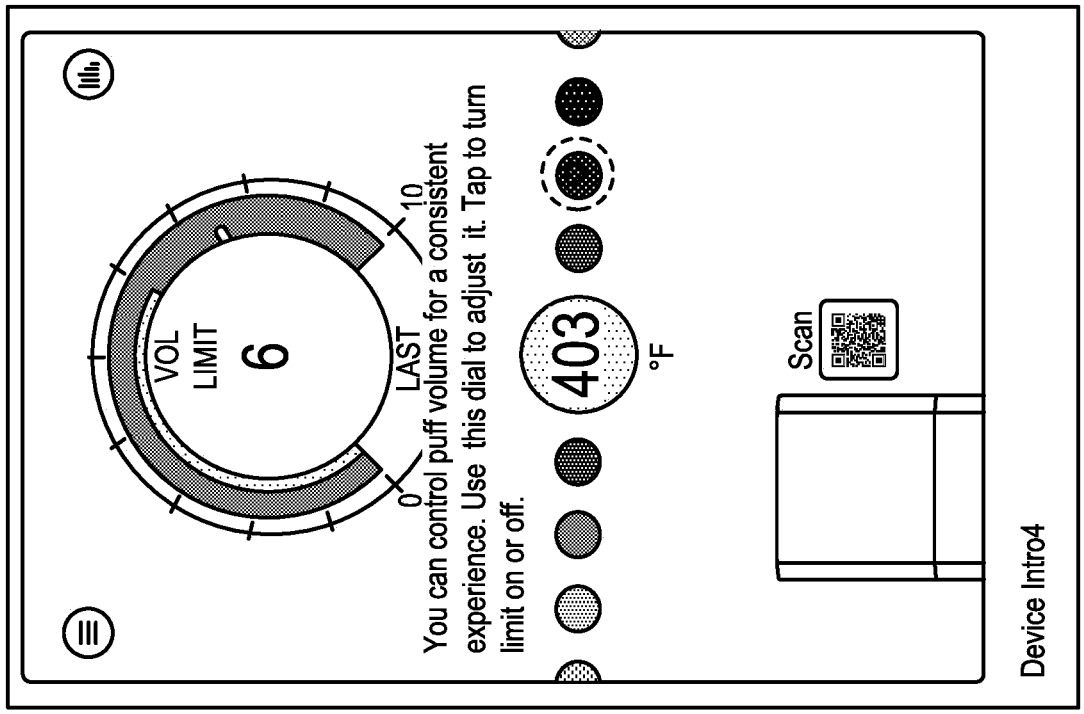
Figure 19D:
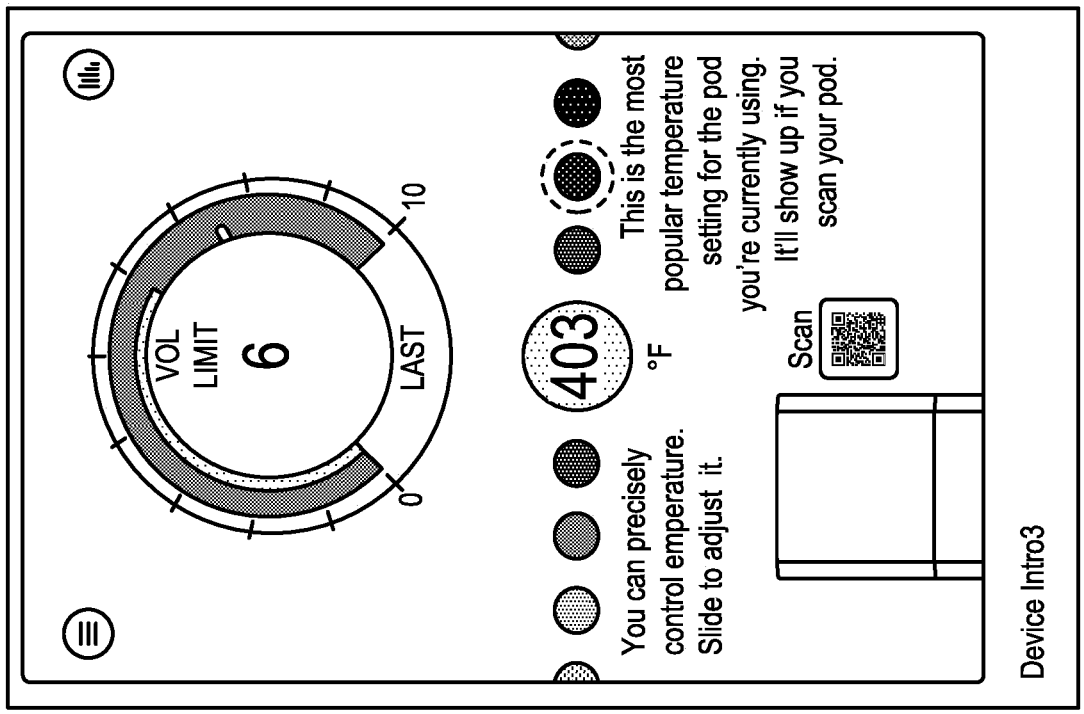

FIGS. 19A-19F illustrate UIs that may be used to instruct a user how to control the vaporizer using the app, cartridge identification (FIGS. 19B-19C), temperature control (FIG. 19D), puff/dose monitoring (FIGS. 19E-19F), etc. As shown in FIG. 19D, recommendations may be provided to show popular settings.

USER EXPERIENCES. FIGS. 25A-30 illustrate various UIs for creating a customized user experience, consistent with implementations of the current subject matter.

Figure 25C:
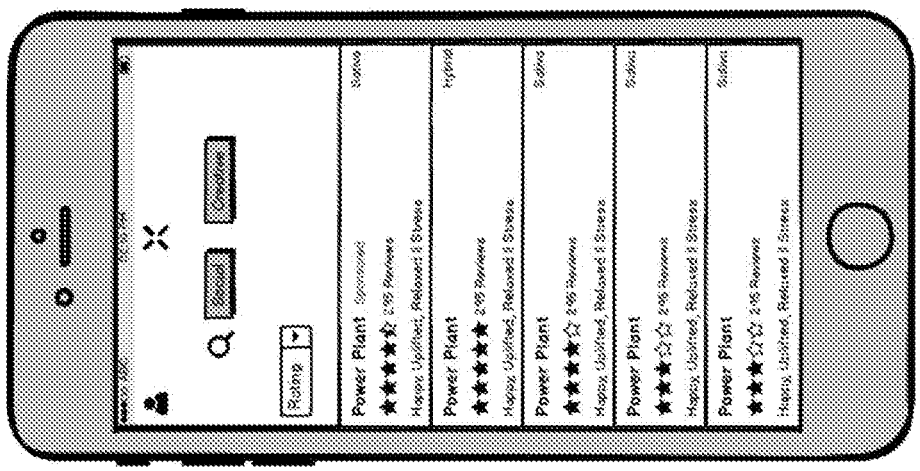
FIGS. 25A-25C and 26A-26C illustrate features of an exemplary user interface that may be used to identify an experience associated with a cartridge consistent with implementations of the current subject matter.
Figure 25B:
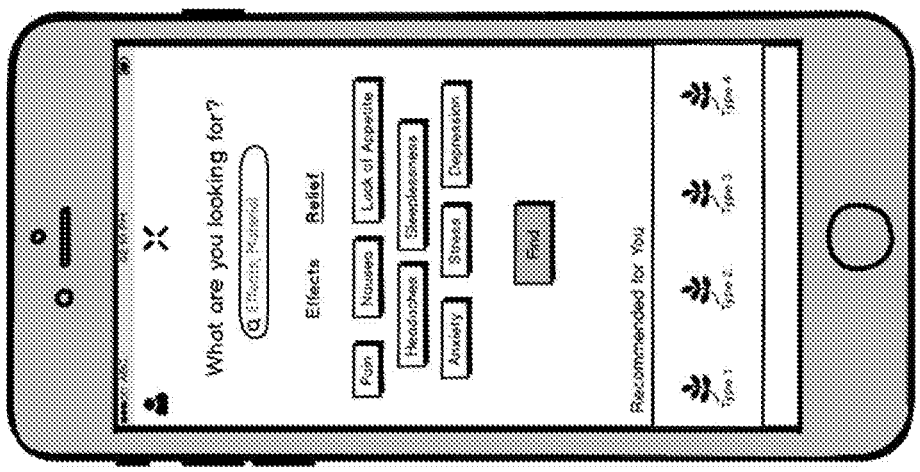
Figure 25A:
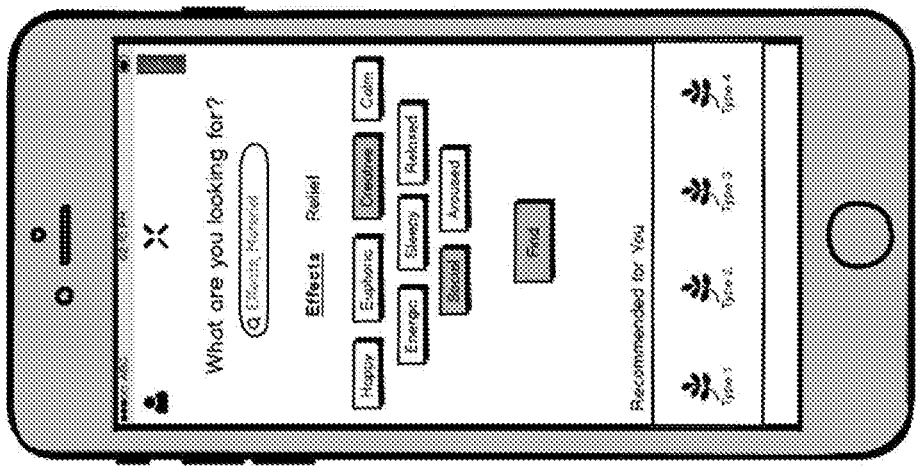

FIGS. 25A-25C illustrate UIs that allow a user to search for a specific experience, such as a desired effect. As shown, a user can selects desired effects (FIG. 25A) and/or desired reliefs (FIG. 25B) and then view a filtered list of cartridge types that meet the selected criteria (FIG. 25C). The filtered list may also include reviews or other information that may be relevant and helpful to the user.

Figure 26C:
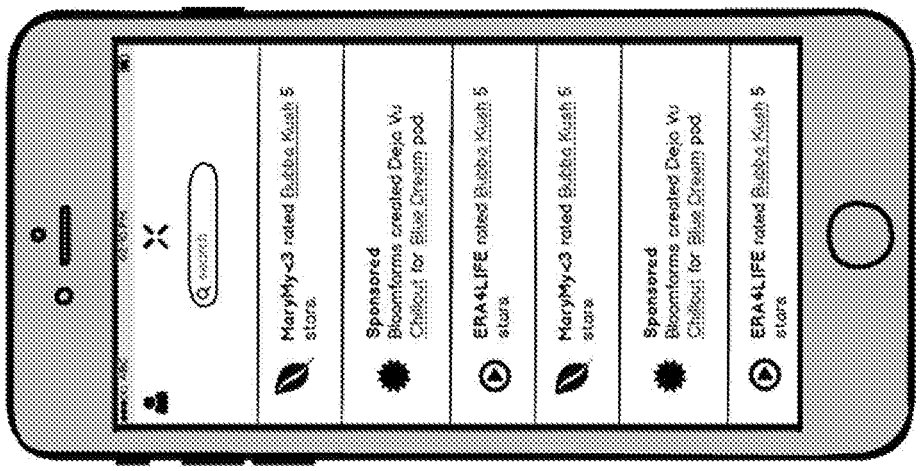
Figure 26B:
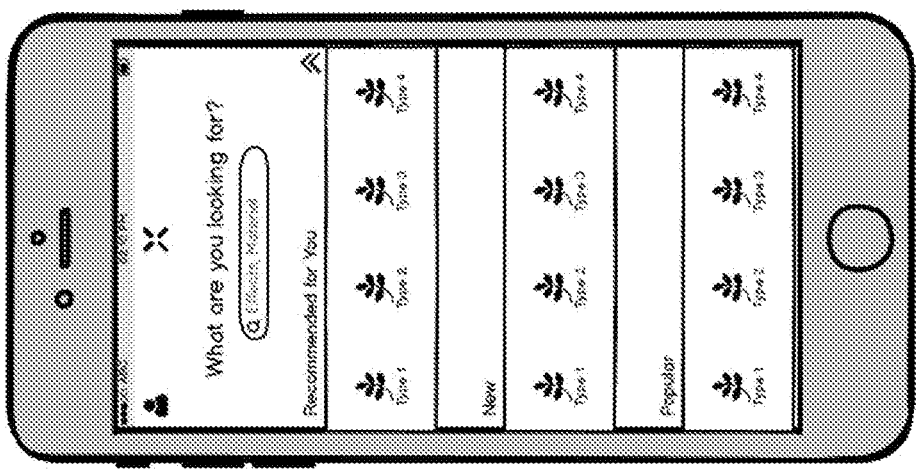
Figure 26A:
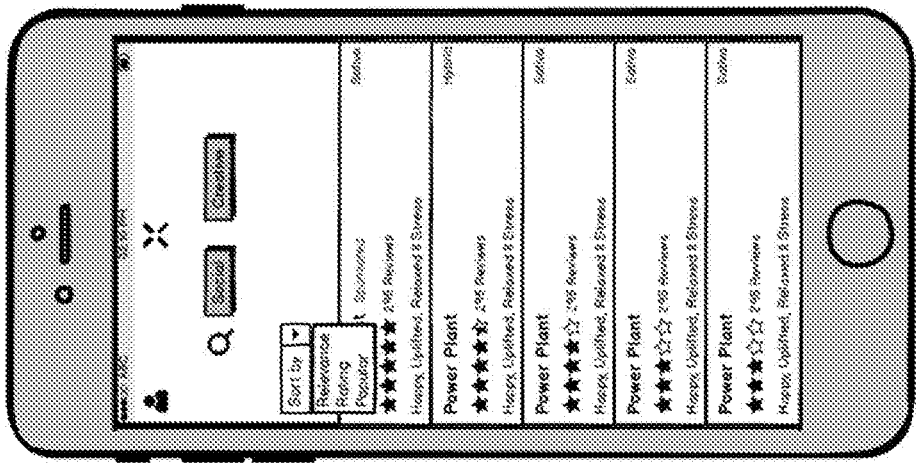

FIGS. 26A-26C illustrate UIs that allow a user to discover new experiences by discovering new cartridges and associated effects, based on indicated preferences (FIG. 26B) and other user ratings (FIG. 26A), for example.

FIGS. 27A-27D illustrate UIs that may be used to learn about various cartridges. For example, upon insertion of a cartridge, the cartridge may be auto-detected, as further described herein, and information about the composition and effects, as well as recommended uses (e.g., temperature) may be provided.

Figure 28C:
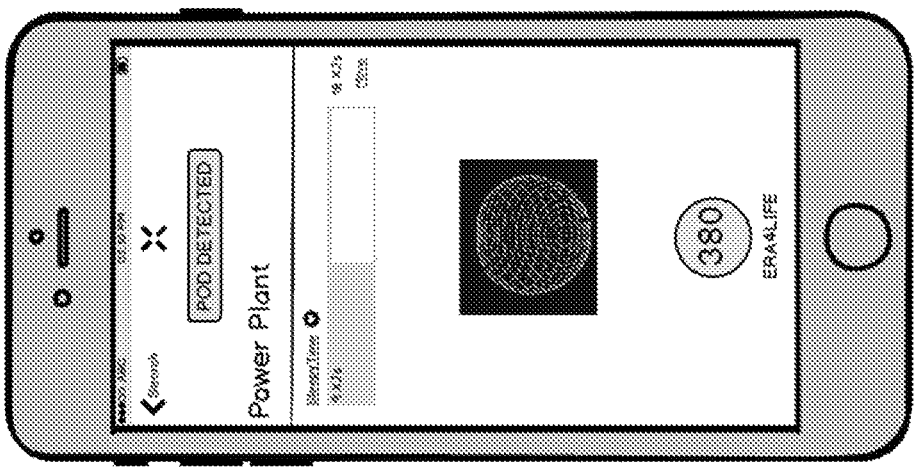
FIGS. 28A-28C illustrate features of an exemplary user interface that may be used to provide a user with recommendations on use consistent with implementations of the current subject matter.
Figure 28B:
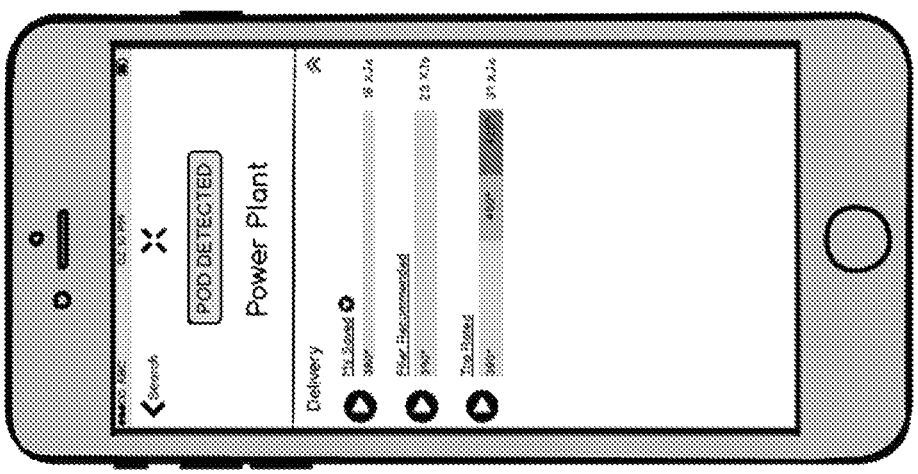
Figure 28A:
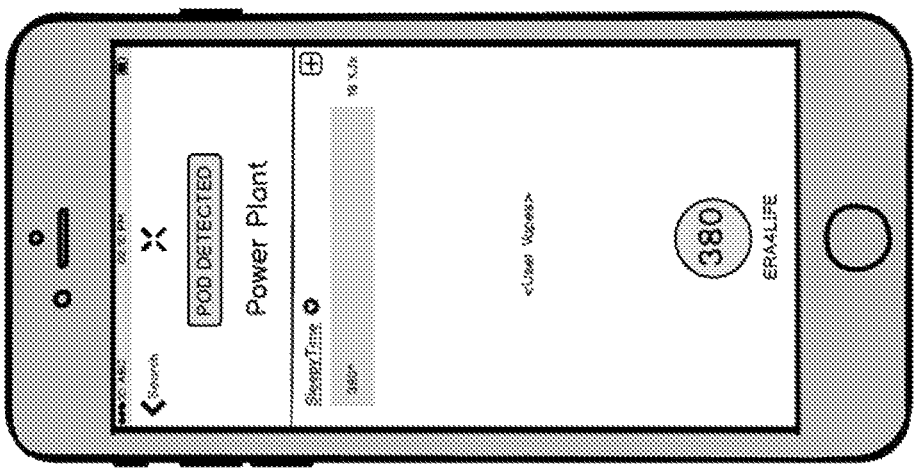

FIGS. 28A-28C illustrate UIs that may be used to provide a user with recommendations on use for optimized delivery. For example, upon detection of a cartridge, a recommended temperature may be provided (FIG. 28A). Additionally, saved preferences and other recommendations may be provided (FIG. 28B). The UIs allow a user to choose from recommended dose amounts, based on, for example, desired effects and past sensitivity.

Figure 29:
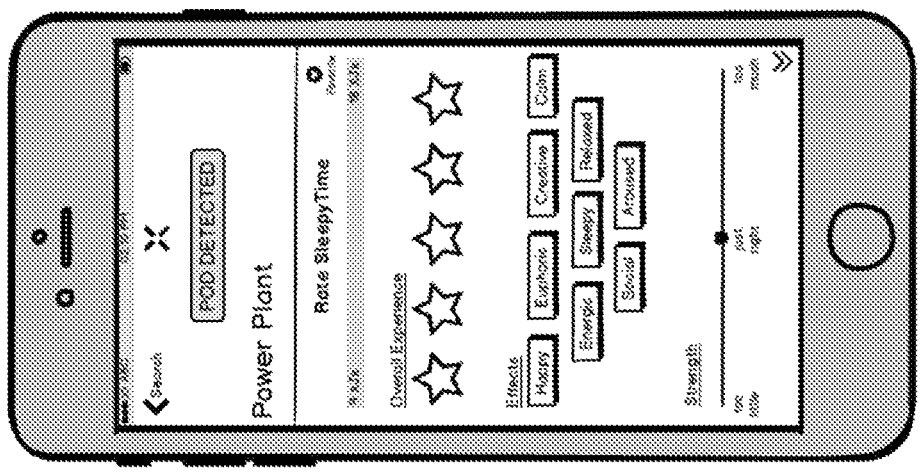
FIG. 29 illustrates features of an exemplary user interface that may be used to provide crowdsourced data consistent with implementations of the current subject matter.

FIG. 29 illustrates a UI that may be used to provide crowdsourced data, such as data on effects and efficacy of different cartridges.

Figure 30:
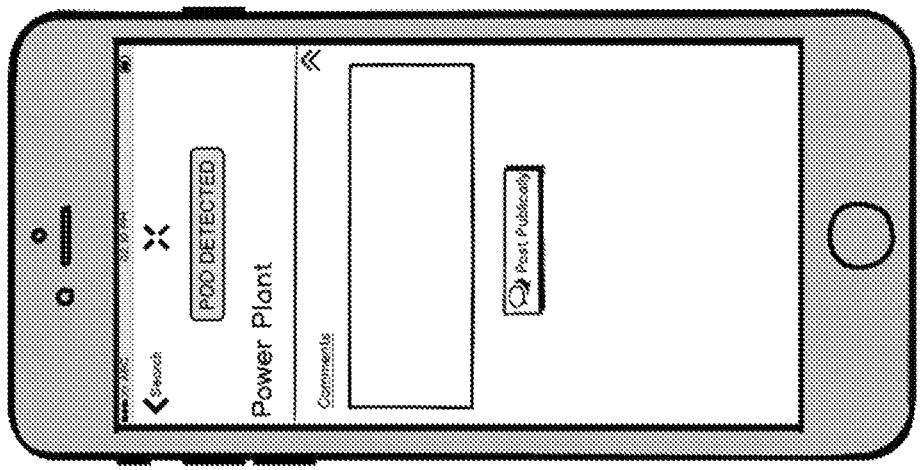
FIG. 30 illustrates features of an exemplary user interface that may be used to provide information on a user's experience consistent with implementations of the current subject matter.

FIG. 30 illustrates a UI that allows a user to provide information on a user's experience (dose, temperature, overall experience). The user can access the information later, to review and/or update it.

Figure 31:
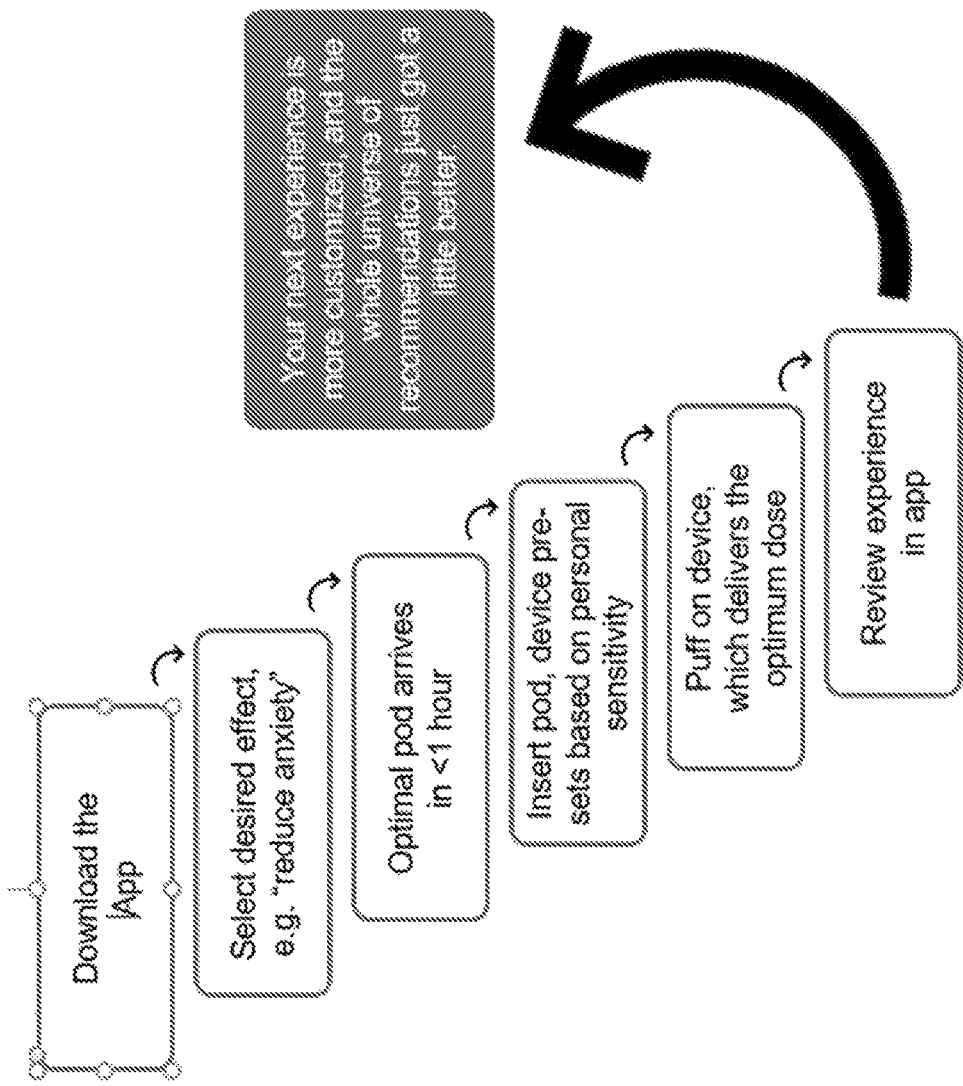
FIGS. 31-35 show flow charts illustrating features of implementing user experiences consistent with implementations of the current subject matter.
Figure 32:
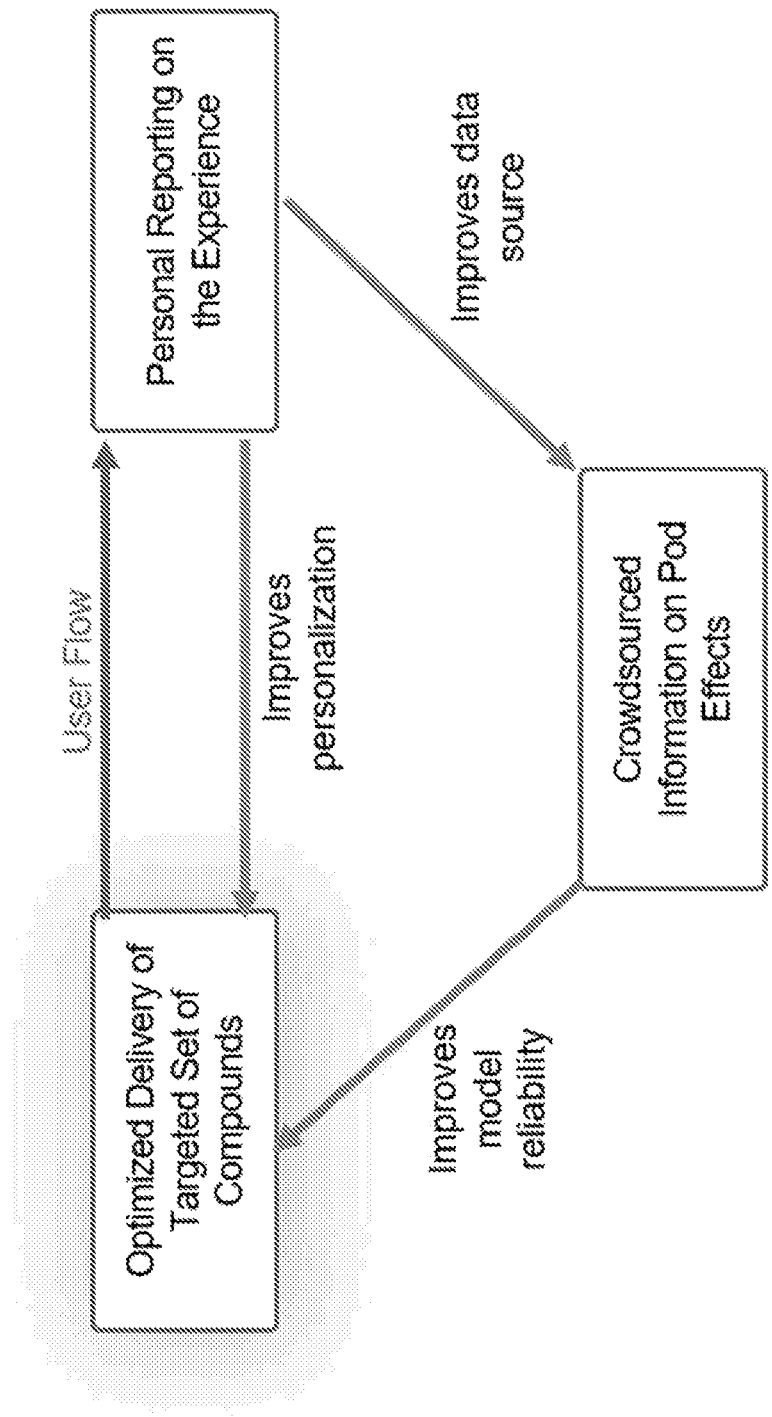
Figure 33:
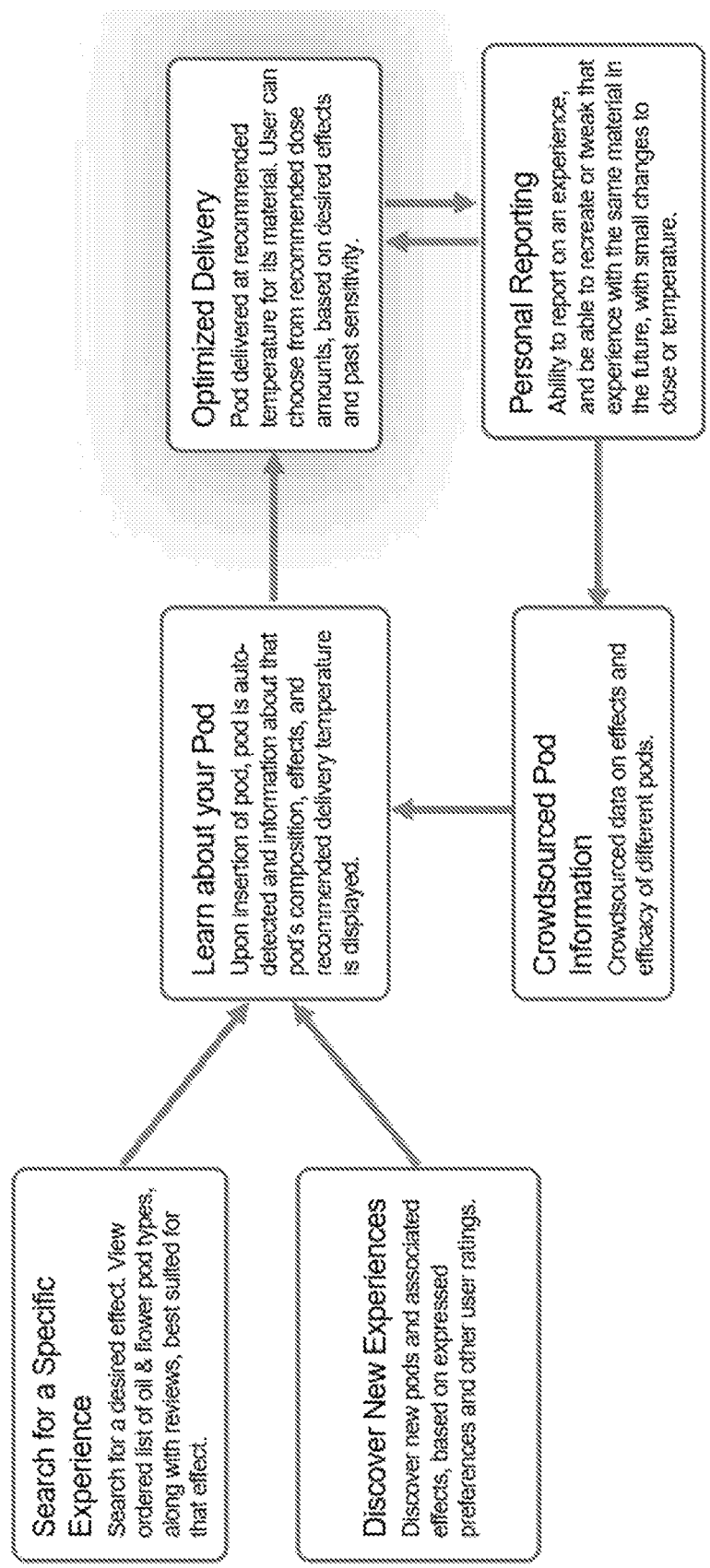

FIGS. 31-35 show flow charts illustrating features of implementing user experiences consistent with implementations of the current subject matter. As shown in FIGS. 31-33, by using the app while using a particular cartridge to rate or otherwise indicate a user's experience, future customizations and recommendations may be provided. The personal reporting can also be used as crowdsourced data, to improve customization and recommendations for a number of users.

Figure 34:
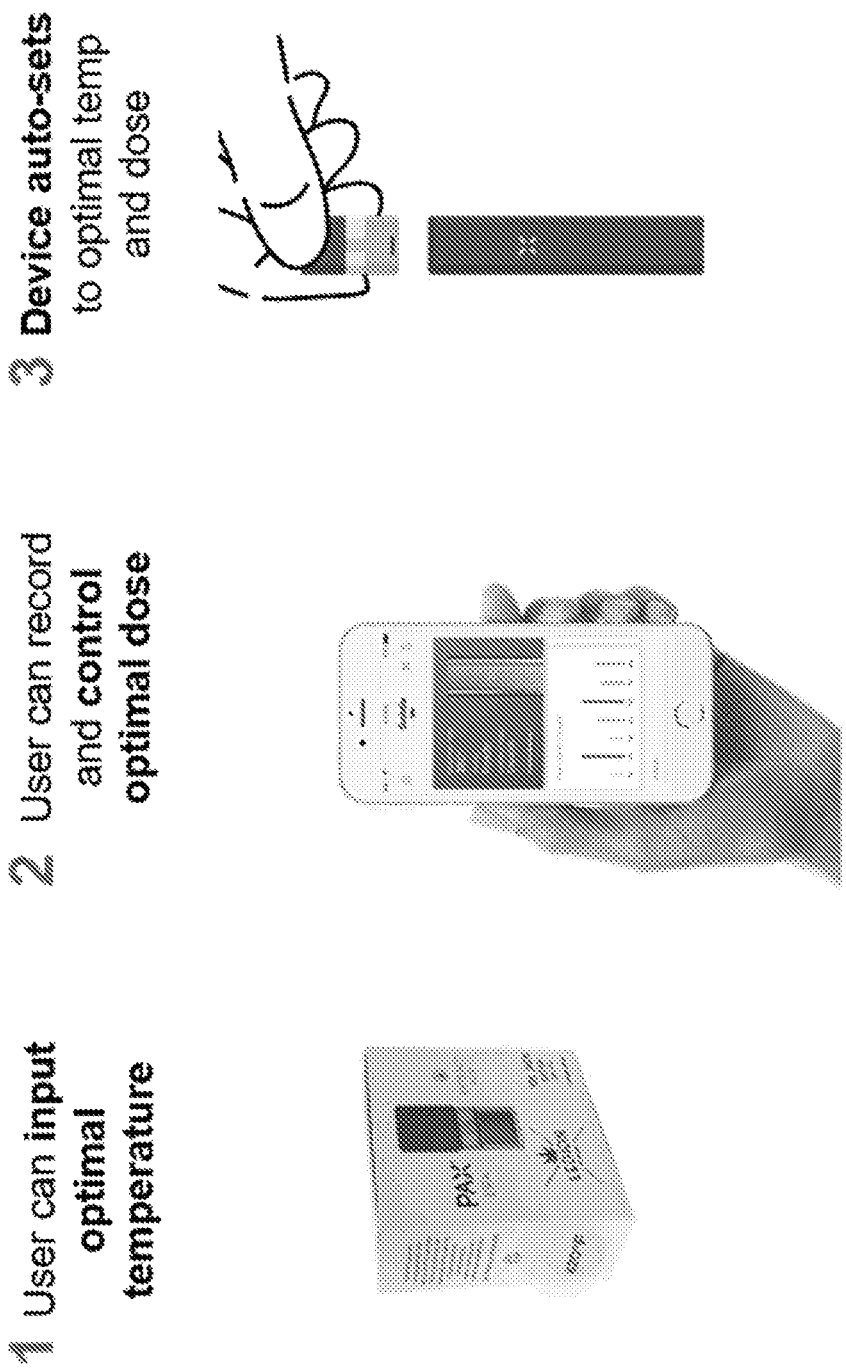
Figure 35:
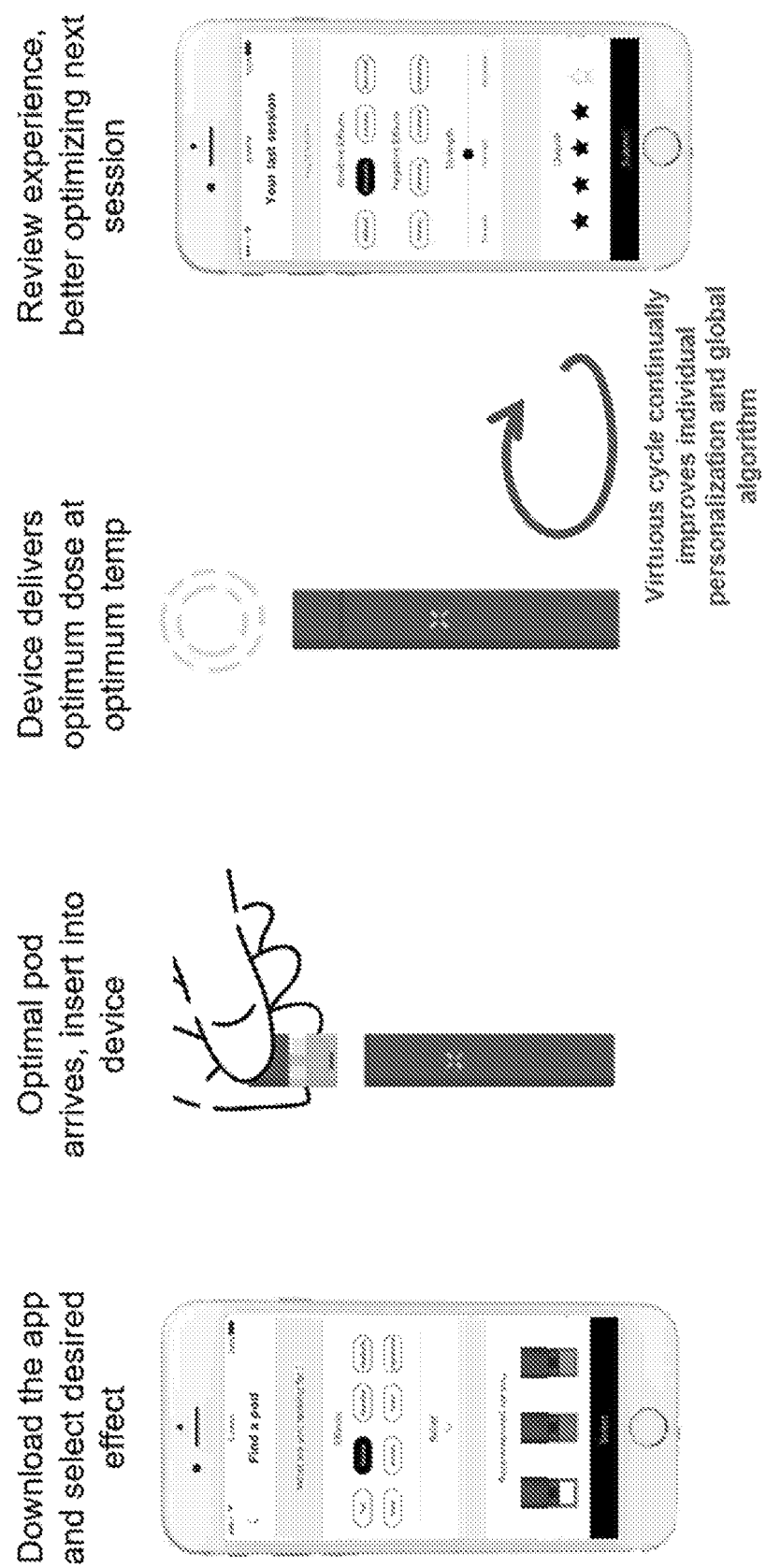

As shown in FIGS. 34-35, prior to use of a vaporizer, a user can pre-select, through the app, a desired temperature or dose or overall effect (or such parameters may be preconfigured). Then when a cartridge is inserted, the pre-selected or preconfigured parameters are automatically applied. By reviewing their experience, the user's next experience may be improved through recommendations.

VAPORIZABLE MATERIAL. As described above, a vaporizer and/or vaporizer system consistent with implementations of the current subject matter may be used with (and may include or be configured specifically for) any appropriate vaporizable material. In certain embodiments, the vaporizable material is an organic material. In certain examples, vaporizable material includes a liquid, a viscous liquid, a wax, a loose-leaf plant material, etc. In certain examples, the vaporizable material is a tobacco-based material. In certain examples, the vaporizable material is a Cannabis-based material. In certain examples, the vaporizable material is a botanical. In certain examples, the vaporizable material is nicotine, a nicotine derivative or a nicotine salt. In certain examples, the vaporizable material is a nutraceutical. In certain examples, the vaporizable material contains a cannabinoid. In certain examples, the vaporizable material is a medicinal compound.

In certain examples, the vaporizable material exhibits a viscosity between 1 and 50 Centipoise. In certain embodiments, the vaporizable material exhibits a viscosity between 50 and 1,000 Centipoise. In certain examples, the vaporizable material exhibits a viscosity between 1,000 and 5,000 Centipoise. In certain examples, the vaporizable material exhibits a viscosity between 5,000 and 10,000 Centipoise. In certain examples, the vaporizable material exhibits a viscosity above 10,000 Centipoise.

In certain examples, the vaporizable material contains nicotine. In certain examples, the vaporizable material contains a nicotine derivative. In certain examples, the nicotine derivative is an acid salt of nicotine. In certain embodiments, the acid salt of nicotine comprises an organic acid. In certain examples, the acid salt of nicotine does not comprise an inorganic acid.

In certain examples, the vaporizable material is a formulation of nicotine, nicotine derivatives, or a nicotine salt. In some formulations the concentration of nicotine or derivatives thereof in the formulation is about 1% (w/w) to about 25% (w/w). In some formulations the concentration of nicotine or derivatives thereof; in the formulation is about 1% (w/w) to about 20% (w/w). In some formulations the concentration of nicotine in the formulation is about 1% (w/w) to about 18% (w/w). In some examples, the concentration of nicotine in the formulation is about 1% (w/w) to about 15% (w/w). In some examples, the concentration of nicotine in the formulation is about 1% (w/w) to about 10% (w/w). In some examples, the concentration of nicotine in the formulation is about 1% (w/w) to about 8% (w/w). In some examples, the concentration of nicotine in the formulation is about 2% (w/w) to about 10% (w/w). In some formulations the concentration of nicotine in the formulation is about 4% (w/w) to about 12% (w/w). In some formulations the concentration of nicotine in the formulation is about 4% (w/w). In some examples, the concentration of nicotine in the formulation is about 2% (w/w).

Nicotine salt formulations are formed by the addition of a suitable acid to nicotine or a derivative thereof, including organic or inorganic acids. In some formulations provided herein, suitable organic acids are carboxylic acids. Examples of organic carboxylic acids disclosed herein are monocarboxylic acids, dicarboxylic acids (organic acid containing two carboxylic acid groups), carboxylic acids containing an aromatic group such as benzoic acids, hydroxycarboxylic acids, heterocyclic carboxylic acids, terpenoid acids, sugar acids; such as the pectic acids, amino acids, cycloaliphatic acids, aliphatic carboxylic acids, keto carboxylic acids, and the like. In some formulations provided herein, the organic acids used herein are monocarboxylic acids. In some formulations provided herein the organic carboxylic acid is benzoic, levulinic, acetic, lactic, citric, sorbic, lauric, salicylic, pyruvic or a combination thereof. In some formulations provided herein the organic carboxylic acid is not levulinic. Nicotine salts are formed from the addition of a suitable acid to nicotine. In some formulations provided herein, the stoichiometric ratios of the nicotine to acid (nicotine: acid) are 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In some formulations provided herein, the stoichiometric ratios of the nicotine to acid are 1:1, 1:2, 1:3, or 1:4 (nicotine: acid).

In certain examples, the pH of the nicotine formulation is acidic. In certain examples, the pH of the nicotine formulation is <7.0. In certain examples, the pH of the nicotine formulation is <6.0. In certain examples, the pH of the nicotine formulation is <5.0. In certain examples, the pH of the nicotine formulation is <4.0. In certain examples, the pH of the nicotine formulation is >3.0. In certain examples, the pH of the nicotine formulation is >4.0. In certain examples, the pH of the nicotine formulation is >5.0. In certain examples, the pH of the nicotine formulation is >6.0.

In certain examples, the vaporizable material contains organic material from a Cannabis genus plant. In certain examples, the vaporizable material contains an extract from a Cannabis genus plant. In certain examples, the vaporizable material contains a cannabinoid. In certain examples, the cannabinoid is tetrahydrocannabinol (THC). In certain examples, the cannabinoid is cannabigerolic acid (CBGA). In certain examples, the cannabinoid is cannabigerol (CBG). In certain examples, the cannabinoid is tetrahydrocannabinolic acid (THCA). In certain examples, the cannabinoid is cannabichromene (CBC). In certain examples, the cannabinoid is cannabicyclol (CBL). In certain examples, the cannabinoid is cannabivarin (CBV). In certain examples, the cannabinoid is cannabichromevarin (CBCV). In certain examples, the cannabinoid is cannabigerovarin (CBGV). In certain examples, the cannabinoid is cannabigerol Monomethyl Ether (CBGM). In certain examples, the cannabinoid is delta-8-tetrahydrocannabinol (D8THC). In certain examples, the cannabinoid is delta-9-tetrahydrocannabinol (D9THC). In certain examples, the cannabinoid is tetrahydrocannabivarin (THCV). In certain examples, the cannabinoid is cannabinolic acid (CBNA). In certain examples, the cannabinoid is Cannabinol (CBN). In certain examples, the cannabinoid is cannabidiolic acid (CBDA). In certain examples, the cannabinoid is Cannabidivaric acid (CBDVA). In certain examples, the cannabinoid is cannabidiol (CBD). In certain examples, the cannabinoid is cannabichromenic acid (CBCA). In certain examples, the cannabinoid is Cannabichromene (CBC). In certain examples, the cannabinoid is cannabicyclolic acid (CBLA). In certain examples, the cannabinoid is a stereo isomer of any of the above mentioned cannabinoids. In certain examples, the cannabinoid is a salt of any of the above mentioned cannabinoids.

In certain examples, the vaporizable material is a cannabinoid formulation. In certain examples, the concentration of cannabinoid in the cannabinoid formulation is from 1-99% cannabinoid. In certain examples, the concentration of cannabinoid in the cannabinoid formulation is from 5-95% cannabinoid. In certain examples, the concentration of cannabinoid in the cannabinoid formulation is from 10-90% cannabinoid. In certain examples, the concentration of cannabinoid in the cannabinoid formulation exceeds about 99% cannabinoid. In certain examples, the concentration of cannabinoid in the cannabinoid formulation exceeds about 98% cannabinoid. In certain examples, the concentration of cannabinoid in the cannabinoid formulation exceeds about 97% cannabinoid. In certain examples, the concentration of cannabinoid in the cannabinoid formulation exceeds about 96% cannabinoid. In certain examples, the concentration of cannabinoid in the cannabinoid formulation exceeds about 95% cannabinoid. In certain examples, the concentration of cannabinoid in the cannabinoid formulation exceeds about 94% cannabinoid. In certain examples, the concentration of cannabinoid in the cannabinoid formulation exceeds about 93% cannabinoid. In certain examples, the concentration of cannabinoid in the cannabinoid formulation exceeds about 92% cannabinoid. In certain examples, the concentration of cannabinoid in the cannabinoid formulation exceeds about 91% cannabinoid. In certain examples, the concentration of cannabinoid in the cannabinoid formulation exceeds about 90% cannabinoid. In certain examples, the concentration of cannabinoid in the cannabinoid formulation exceeds about 80% cannabinoid. In certain examples, the concentration of cannabinoid in the cannabinoid formulation exceeds about 70% cannabinoid. In certain examples, the concentration of cannabinoid in the cannabinoid formulation exceeds about 60% cannabinoid. In certain examples, the concentration of in the cannabinoid formulation exceeds about 50% cannabinoid. In certain examples, the concentration of in the cannabinoid formulation exceeds about 40% cannabinoid. In certain examples, the concentration of cannabinoid in the cannabinoid formulation exceeds about 30% cannabinoid. In certain examples, the concentration of cannabinoid in the cannabinoid formulation exceeds about 20% cannabinoid. In certain examples, the concentration of cannabinoid in the cannabinoid formulation exceeds about 10% cannabinoid. In certain examples, the concentration of cannabinoid in the cannabinoid formulation is from about 1% to about 10% cannabinoid. In certain examples, the concentration of cannabinoid in the cannabinoid formulation is from about 10% to about 20% cannabinoid. In certain examples, the concentration of cannabinoid in the cannabinoid formulation is from about 20% to about 30% cannabinoid. In certain examples, the concentration of cannabinoid in the cannabinoid formulation is from about 30% to about 40% cannabinoid. In certain examples, the concentration of cannabinoid in the cannabinoid formulation is from about 40% to about 50% cannabinoid. In certain examples, the concentration of cannabinoid in the cannabinoid formulation is from about 50% to about 60% cannabinoid. In certain examples, the concentration of cannabinoid in the cannabinoid formulation is from about 60% to about 70% cannabinoid. In certain examples, the concentration of cannabinoid in the cannabinoid formulation is from about 70% to about 80% cannabinoid. In certain examples, the concentration of cannabinoid in the cannabinoid formulation is from about 80% to about 90% cannabinoid. In certain examples, the concentration of cannabinoid in the cannabinoid formulation is from about 90% to about 100% cannabinoid.

In certain examples, the pH of the cannabinoid formulation is acidic. In certain examples, the pH of the cannabinoid formulation is <7.0. In certain examples, the pH of the cannabinoid formulation is <6.0 In certain examples, the pH of the cannabinoid formulation is <5.0. In certain examples, the pH of the cannabinoid formulation is <4.0. In certain examples, the pH of the cannabinoid formulation is >3.0. In certain examples, the pH of the cannabinoid formulation is >4.0. In certain examples, the pH of the cannabinoid formulation is >5.0. In certain examples, the pH of the cannabinoid formulation is >6.0. In certain examples, the pH of the cannabinoid formulation is basic. In certain examples, the pH of the cannabinoid formulation is <10.0. In certain examples, the pH of the cannabinoid formulation is <9.0 In certain examples, the pH of the cannabinoid formulation is <8.0. In certain examples, the pH of the cannabinoid formulation is >7.0. In certain examples, the pH of the cannabinoid formulation is >8.0. In certain examples, the pH of the cannabinoid formulation is >9.0. In certain examples, the pH of the cannabinoid formulation is >10.0.

In certain examples, the vaporizable material is a Cannabis formulation. In certain examples, the concentration of the Cannabis formulation is from 1-99% Cannabis. In certain examples, the concentration of the Cannabis formulation is from 5-95% Cannabis. In certain examples, the concentration of the Cannabis formulation is from 10-90% Cannabis. In certain examples, the Cannabis formulation exceeds about 99% Cannabis. In certain examples, the Cannabis formulation exceeds about 98% Cannabis. In certain examples, the Cannabis formulation exceeds about 97% Cannabis. In certain examples, the Cannabis formulation exceeds about 96% Cannabis. In certain examples, the Cannabis formulation exceeds about 95% Cannabis. In certain examples, the Cannabis formulation exceeds about 94% Cannabis. In certain examples, the Cannabis formulation exceeds about 93% Cannabis. In certain examples, the Cannabis formulation exceeds about 92% Cannabis. In certain examples, the Cannabis formulation exceeds about 91% Cannabis. In certain examples, the Cannabis formulation exceeds about 90% Cannabis. In certain examples, the Cannabis formulation exceeds about 80% Cannabis. In certain examples, the Cannabis formulation exceeds about 70% Cannabis. In certain examples, the Cannabis formulation exceeds about 60% Cannabis. In certain examples, the Cannabis formulation exceeds about 50% Cannabis. In certain examples, the Cannabis formulation exceeds about 40% Cannabis. In certain examples, the Cannabis formulation exceeds about 30% Cannabis. In certain examples, the Cannabis formulation exceeds about 20% Cannabis. In certain examples, the Cannabis formulation exceeds about 10% Cannabis.

In certain examples, the pH of the Cannabis formulation is acidic. In certain examples, the pH of the Cannabis formulation is <7.0. In certain examples, the pH of the Cannabis formulation is <6.0 In certain examples, the pH of the Cannabis formulation is <5.0. In certain examples, the pH of the Cannabis formulation is <4.0. In certain examples, the pH of the Cannabis formulation is >3.0. In certain examples, the pH of the Cannabis formulation is >4.0. In certain examples, the pH of the Cannabis formulation is >5.0. In certain examples, the pH of the Cannabis formulation is >6.0. In certain examples, the pH of the Cannabis formulation is basic. In certain examples, the pH of the Cannabis formulation is <10.0. In certain examples, the pH of the Cannabis formulation is <9.0 In certain examples, the pH of the Cannabis formulation is <8.0. In certain examples, the pH of the Cannabis formulation is >7.0. In certain examples, the pH of the Cannabis formulation is >8.0. In certain examples, the pH of the Cannabis formulation is >9.0. In certain examples, the pH of the Cannabis formulation is >10.0.

In certain examples, the vaporizable material contains a medicinal compound as an active ingredient. The medicinal compounds that are active ingredients for vaporization with the electronic vaporizer device utilizing the method herein, include drugs that can be heated without combustion to vaporization for inhalation delivery at a temperature range of, e.g., about 100° C. (e.g., for water-based carriers, e.g., about 100° C., 105° C., 110° C., 120° C., 130° C., 140° C., 150° C., 160° C., 170° C., etc.; for ethanol-based formulations, e.g., about 50° C., about 60° C., about 70° C., about 80° C., etc.) to about (e.g., below) the temperature at which the active ingredient thermally decomposes (e.g., less than about 150° C., 160° C., 170° C., 180° C., 190° C., 200° C., 210° C., 220° C., 230° C., 240° C., 250° C., 260° C., 270° C., 280° C., 290° C., 300° C., etc.). In certain examples, the drugs can be neat or are solubilized in a pharmaceutically acceptable solvent. In certain examples, the drugs can include over the counter (OTC) substances as aides for various ailments; wherein said drugs can include known respiratory aides for asthma or chronic obstructive pulmonary disease (COPD). The vaporizable materials that are active ingredients for vaporization with the device(s) herein described, can include drugs that can be heated to vaporization for inhalation delivery, without combustion; wherein said drugs can include over the counter (OTC) substances from the group comprising upper respiratory aides (like cetirizine), analgesics and internal medication aides (like ibuprofen, naproxen), heartburn aides (like omeprazole), sleeping aides (like doxylamine, diphenhydramine, melatonin), or motion sickness aides (like meclizine). In certain examples, the vaporizable material can contain respiratory aides for asthma or chronic obstructive pulmonary disease (COPD) such as short acting beta-agonist (like albuterol, levalbuterol, pirbuterol), long acting beta-agonist (like salmeterol, formoterol), anti-cholinergics (like atropine sulfate, ipratropium bromide), leukotriene modifiers (like montelukast, zafirlukast), cartico-steriods (like fluticasone, budesonide, mometasone), theophylline (like theophylline), or combination corticosteroid and beta agonist, long lasting (fluticasone and salmeterol, budesonide and formoterol, mometasone and formoterol). In certain examples, the vaporizable material can contain botanicals and/or nutraceuticals such as tea (polyphenols, flavonoids, green tea catechins+/−caffeine); horehound (phenol flavonoid glycosides, labdane diterpenoids, yohimbe, cranberry/grape (proanthocyanidins), black cohosh (terpene glycoside fraction (actine/cimifugoside), flax seed (omega fatty acids), echinacea (echinacoside), valerian (alkaloids, gabapentin, isovaleric acid, terpenes), senna (senna cglycosides), cinnamon (cinnamaldehyde, phenols, terpenes), vitamin D, saw palmetto (fatty acids), or caffeine. In certain examples, the vaporizable material is soluble to at least fifty percent by weight in any suitable carrier solvent such as glycols (such as propylene glycol and vegetable glycerin), ethylene glycol, dipropylene glycol, trimethylene glycol, ethanol, and combinations thereof. In certain examples, the medicinal compound is terpinolene. In certain examples, the medicinal compound is Linalool. In certain examples, the medicinal compound is phytol. In certain examples, the medicinal compound is beta myrcene. In certain examples, the medicinal compound is citronellol. In certain examples, the medicinal compound is caryophyllene oxide. In certain examples, the medicinal compound is alpha pinene. In certain examples, the medicinal compound is limonene. In certain examples, the medicinal compound is beta caryophyllene. In certain examples, the medicinal compound is humulene. In certain embodiments, the vaporizable material is an essential oil.

Figure 22:
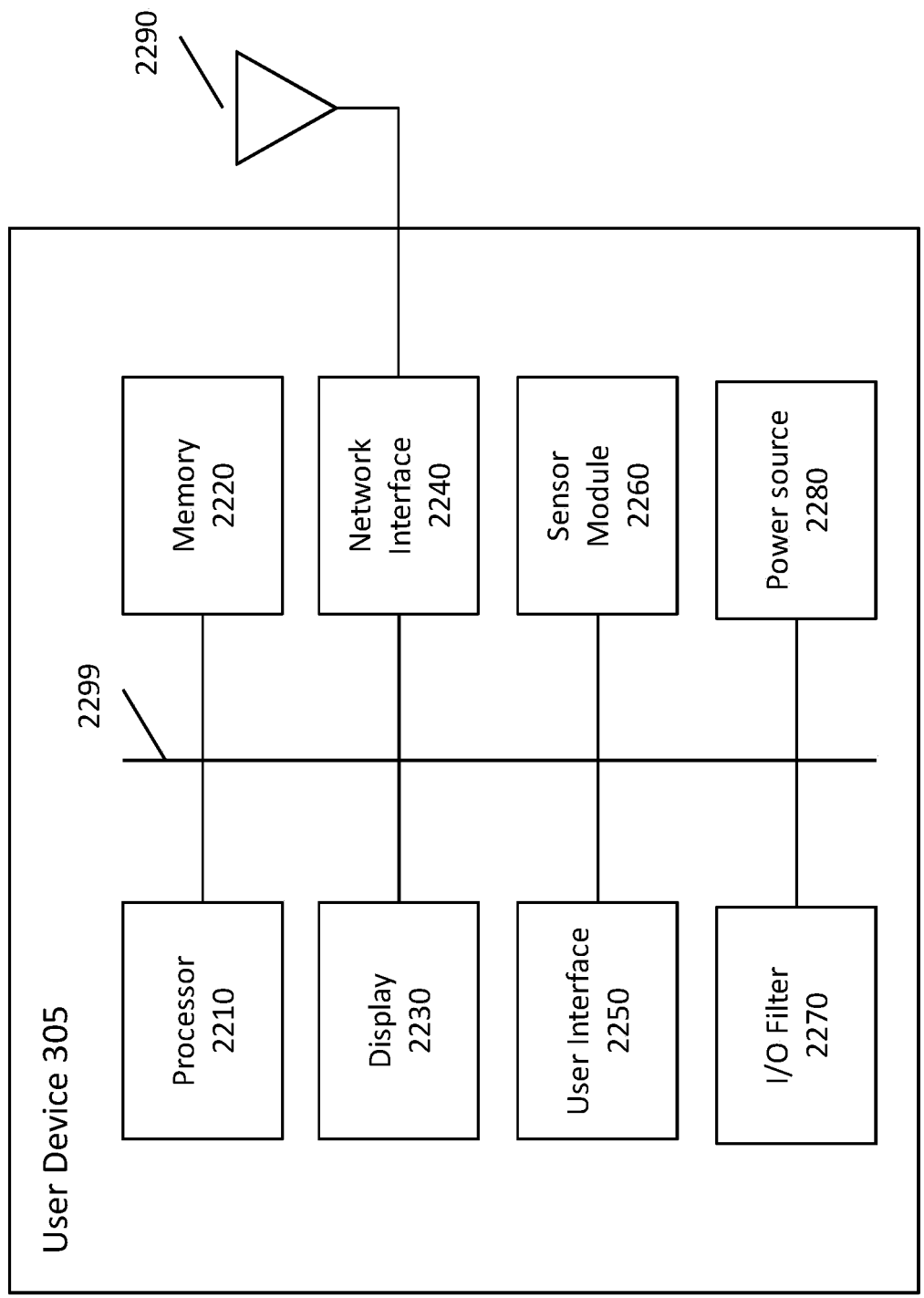
FIG. 22 illustrates a functional block diagram of a user device for implementing features consistent with the described subject matter, in accordance with some example implementations.

FIG. 22 illustrates an example user device 305 which may be used to implement one or more of the described features and/or components, in accordance with some example implementations. User device 305 may perform one or more of the processes described herein. For example, user device 305 may be used to execute an application providing for user control of a vaporizer in communication with user device 305 and to provide an interface for the user to engage and interact with functions related to the vaporizer, in accordance with some example implementations.

As illustrated, user device 305 may include one or more processors such as processor 2210 to execute instructions that may implement operations consistent with those described herein. User device 305 may include memory 2220 to store executable instructions and/or information. Memory 2220 may include solid-state memory, solid-state disk drives, magnetic disk drives, or any other information storage device. In some aspects, the memory 2220 may provide storage for at least a portion of a database. User device 305 may include a network interface 2240 to a wired network or a wireless network, such as the network described with reference to FIG. 3. In order to effectuate wireless communications, the network interface 2240, for example, may utilize one or more antennas, such as antenna 2290.

User device 305 may include one or more user interfaces, such as user interface 2250. The user interface 2250 can include hardware or software interfaces, such as a keyboard, mouse, or other interface, some of which may include a touchscreen integrated with a display 2230. The display 2230 may be used to display information, such as information related to the functions of the vaporizer, provide prompts to a user, receive user input, and/or the like. In various implementations, the user interface 2250 can include one or more peripheral devices and/or the user interface 2250 may be configured to communicate with these peripheral devices.

In some aspects, the user interface 2250 may include one or more of the sensors described herein and/or may include an interface to one or more of the sensors described herein. The operation of these sensors may be controlled at least in part by a sensor module 2260. The user device 305 may also comprise an input and output filter 2270, which can filter information received from the sensors or other user interfaces, received and/or transmitted by the network interface 2240, and/or the like. For example, signals detected through the sensors can be passed through the filter 2270 for proper signal conditioning, and the filtered data may then be passed to the sensor module 2260 and/or processor 2210 for validation and processing (e.g., before transmitting results or an indication via the network interface 2240). The user device 305 may be powered through the use of one or more power sources, such as power source 2280. As illustrated, one or more of the components of the user device 305 may communicate and/or receive power through a system bus 2299.

Figure 23:
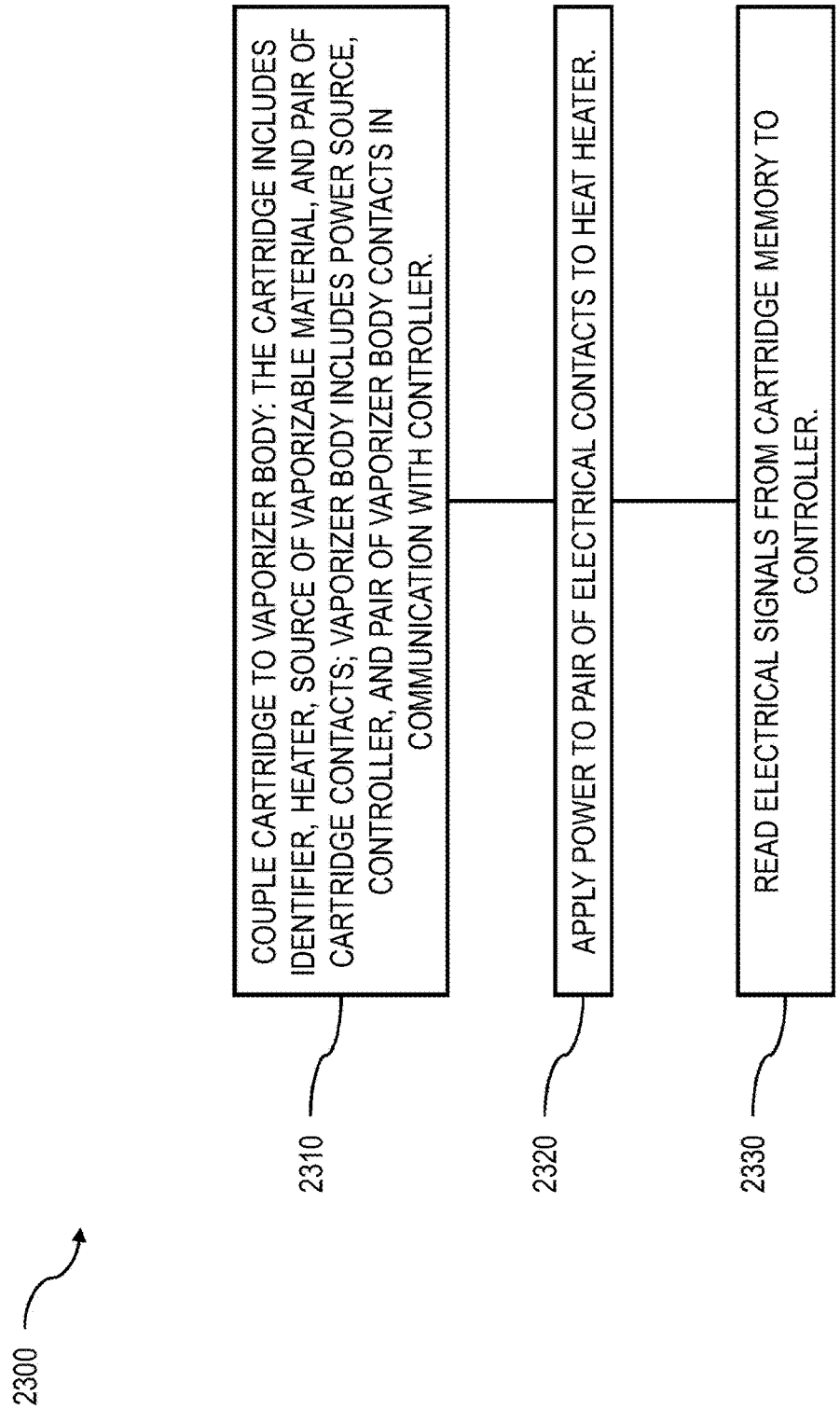
FIG. 23 shows a process flow chart illustrating features of a method of using a vaporizer consistent with implementations of the current subject matter.
Figure 24:
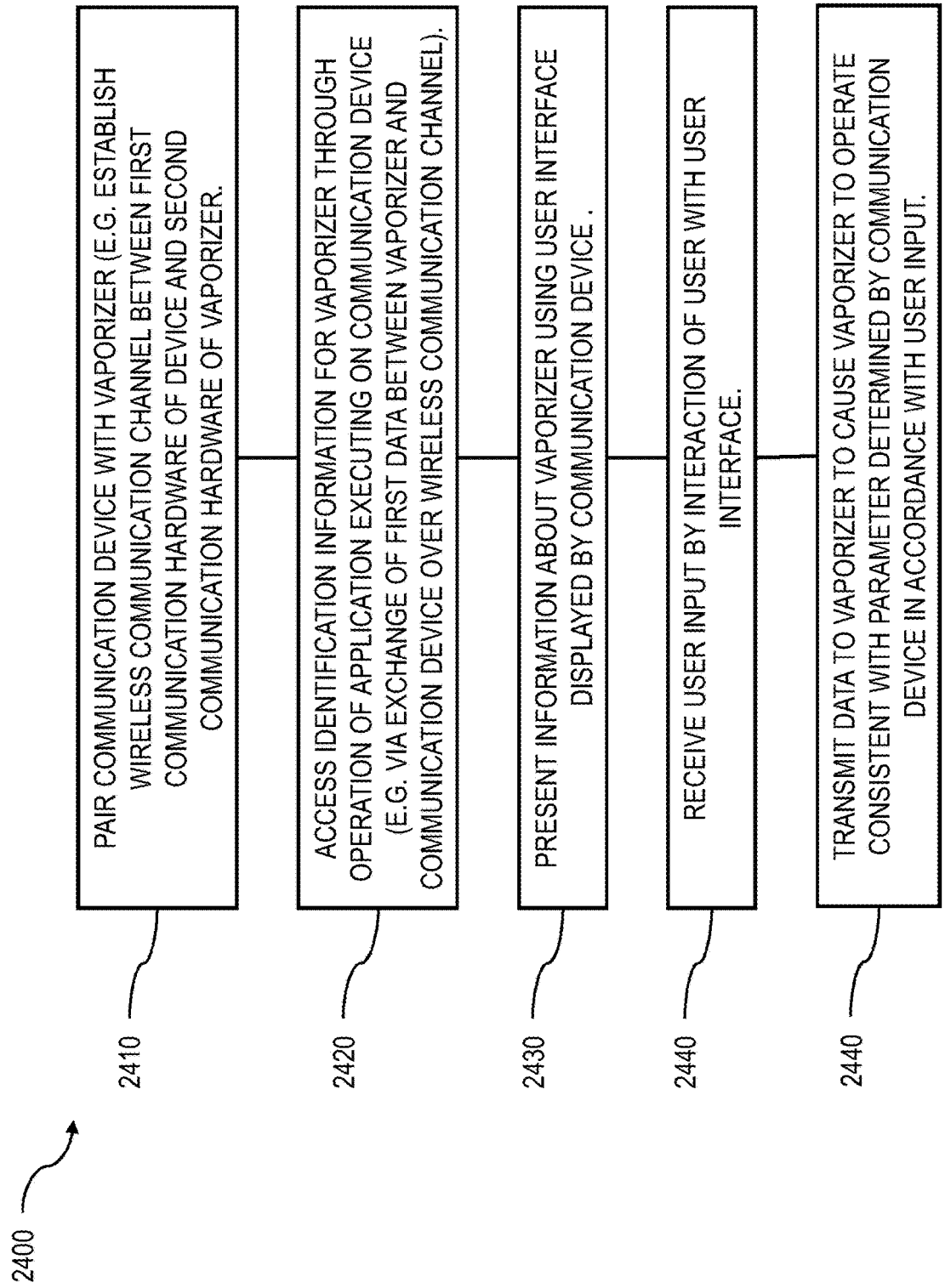
FIG. 24 shows a process flow chart illustrating features of a method of using an application executing on a device that is in communication with a vaporizer as part of a vaporizer system consistent with implementations of the current subject matter.

As noted above, implementations of the current subject matter include various methods of use of vaporizers and vaporizer systems that include a device in communication with a vaporizer. FIG. 23 and FIG. 24 show process flow charts 2300 and 2400 illustrating features of methods consistent with such implementations.

FIG. 23 shows features of a method, which may optionally include some or all of the following. At 2310, a cartridge may be coupled to a vaporizer body. The cartridge may include an identifier, a heater, a source of vaporizable material, and a pair of cartridge contacts. The vaporizer body may include a power source, a controller, and a pair of vaporizer body contacts in communication with the controller. The coupling may include engaging the pair of vaporizer body contacts on the vaporizer body with the pair of cartridge contacts on the cartridge. At 2320, power may be applied to the pair of electrical contacts to heat the heater, and electrical signals may be read from the cartridge memory to the controller at 2330. In some variations, the applying of power and the reading of electrical signals from the cartridge memory to the controller may occur via a circuit completed by engagement of the pair of cartridge contacts with the pair of vaporizer body contacts.

FIG. 24 shows features of a method, which may optionally include some or all of the following. A communication device may be paired with a vaporizer at 2410. The pairing may include establishing a wireless communication channel between first communication hardware of the device and second communication hardware of the vaporizer. At 2420, identification information for the vaporizer may be accessed through operation of an application executing on the communication device. The accessing may include an exchange of first data between the vaporizer and the communication device over the wireless communication channel. Information about the vaporizer may be presented at 2430 using a user interface displayed by the communication device, and a user input may be received at 2440 by interaction of a user with the user interface. At 2450, data may be transmitted to the vaporizer to cause the vaporizer to operate consistent with one or more parameters determined by the communication device in accordance with the user input.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to a given example, the features and elements so described or shown can apply to other implementations of the current subject matter. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification and in the claims, specify the presence of stated features, steps, operations, elements, and/or components, but do not preclude the presence or addition of one or more other features, steps, operations, elements, components, and/or groups thereof.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

We claim:

1. A method for operating a vaporizer, the method comprising:
   accessing, through an operation of an application executing on one or more programmable processors, an information regarding the vaporizer;
   presenting the information about the vaporizer using a user interface generated on a display by the one or more processors;
   receiving a user input by interaction of a user with the user interface;
   determining a location of the vaporizer with respect to one or more beacons; and
   causing the vaporizer to operate consistent with one or more parameters determined by the one or more processors in accordance with the user input, the causing the vaporizer to operate consistent with the one or more parameters comprising disabling the vaporizer based on the determined location with respect to the one or more beacons.

2. The method of claim 1, further comprising:
   pairing a communication device with the vaporizer, the pairing comprising establishing a wireless communication channel between a first communication hardware of the device and a second communication hardware of the vaporizer, wherein the communication device comprises the one or more processors and the display,
   wherein the accessing an information regarding the vaporizer comprises an exchange of a first data between the vaporizer and the communication device over the wireless communication channel, and wherein the causing the vaporizer to operate consistent with the one or more parameters comprises transmitting data to the vaporizer from the communication device.

3. The method of claim 2, wherein the information comprises one or more of desired effects, one or more user reviews, one or more recommendations of use, one or more crowdsourced information, and one or more cartridge information.

4. The method of claim 2, wherein the causing the vaporizer to operate consistent with one or more parameters comprises associating the vaporizer with a purchase location.

5. A method comprising:
   accessing, through an operation of an application executing on one or more programmable processors, an information regarding a vaporizer;
   presenting the information about the vaporizer using a user interface generated on a display by the one or more processors;
   receiving a user input by an interaction of a user with the user interface; and
   causing the vaporizer to operate consistent with one or more parameters determined by the one or more processors in accordance with the user input;
   wherein the vaporizer comprises a cartridge and a vaporizer body configured to be coupled to one another, the cartridge comprising an identifier, a heater, a source of vaporizable material, and a plurality of cartridge contacts, and the vaporizer body comprising a power source, a controller, and a plurality of vaporizer body contacts in communication with the controller, wherein when coupled, the plurality of vaporizer body contacts on the vaporizer body are engaged with the plurality of cartridge contacts on the cartridge;
   wherein the identifier comprises a cartridge memory storing the information regarding the vaporizer, the information regarding the vaporizer comprising a type of vaporizable material contained in the cartridge, and wherein an engagement of the plurality of cartridge contacts and the plurality of vaporizer body contacts forms a data exchange circuit via which data are passed between the cartridge memory and the controller; and
   wherein accessing the information regarding the vaporizer comprises accessing the information encoded by the identifier.

6. The method of claim 5, further comprising:
   pairing a communication device with the vaporizer, the pairing comprising establishing a wireless communication channel between a first communication hardware of the device and a second communication hardware of the vaporizer, wherein the communication device comprises the one or more processors and the display, wherein the accessing the information regarding the vaporizer comprises an exchange of a first data between the vaporizer and the communication device over the wireless communication channel, and wherein the causing the vaporizer to operate consistent with the one or more parameters comprises transmitting data to the vaporizer from the communication device.

7. A vaporizer device comprising:
a memory;
controller circuitry;
a power source; and
at least one of a heating element and a reservoir configured for containing a vaporizable material, a coupler configured for coupling with a cartridge containing a cartridge reservoir and a cartridge heating element, or an oven configured to receive the vaporizable material;
wherein the controller circuitry is configured to perform operations comprising:
pairing a communication device with the vaporizer, the pairing comprising establishing a wireless communication channel between a first communication hardware of the device and a second communication hardware of the vaporizer, wherein the communication device comprises one or more processors and a display;
accessing an information regarding the vaporizer, wherein the accessing the information regarding the vaporizer comprises an exchange of a first data between the vaporizer and the communication device over the wireless communication channel;
presenting information about the vaporizer using a user interface generated on the display by the one or more processors;
receiving, via the wireless communication channel, a user input from interaction of a user with the user interface;
determining a location of the vaporizer with respect to one or more beacons or one or more geo-fenced areas; and
causing the vaporizer device to operate consistent with one or more parameters determined by the one or more processors in accordance with the user input, the causing the vaporizer to operate comprising disabling the vaporizer device based on the determined location with respect to the one or more beacons or one or more geo-fenced areas, and wherein the causing the vaporizer to operate comprises transmitting the data to the vaporizer from the communication device.

8. The vaporizer device of claim 7, further comprising circuitry for one or more wireless communication modes;
wherein the controller circuitry is further configured to pair via the circuitry for one or more wireless communication modes with a user's phone and/or mobile device, and disable the vaporizer device based on an indication from the user's phone and/or mobile device that the vaporizer is close to the one or more beacons or within the one or more pre-defined geo-fenced areas.

9. The vaporizer device of claim 7, further comprising a hardware configured for providing location services.

10. A vaporizer comprising:
a cartridge and a vaporizer body configured to be coupled to one another, the cartridge comprising an identifier, a heater, a source of vaporizable material, and a plurality of cartridge contacts, and the vaporizer body comprising a power source, a controller, and a plurality of vaporizer body contacts in communication with the controller, wherein when coupled the plurality of vaporizer body contacts on the vaporizer body are engaged with the plurality of cartridge contacts on the cartridge;
wherein the identifier comprises a cartridge memory storing an information regarding the vaporizer, the information regarding the vaporizer comprising a type of vaporizable material contained in the cartridge,, and wherein an engagement of the plurality of cartridge contacts and the plurality of vaporizer body contacts forms a data exchange circuit via which data are passed between the cartridge memory and the controller;
wherein the controller is configured to perform operations comprising:
communicating with one or more programmable processors executing an application;
providing the application access to the information regarding the vaporizer, the information regarding the vaporizer comprising information encoded by the identifier; and
causing the vaporizer to operate consistent with one or more parameters determined by the one or more processors in accordance with a user input received by interaction of a user with a user interface, the application generating the user interface on a display and presenting the information about the vaporizer via the user interface.

11. The vaporizer of claim 10, wherein:
a communication device comprises the one or more processors, the display, and a first communication hardware;
the vaporizer further comprises a second communication hardware;
the controller communicating with the one or more processors comprises pairing the communication device with the vaporizer,
the pairing comprises establishing a wireless communication channel between the first communication hardware of the communication device and the second communication hardware of the vaporizer;
the providing the application access to the information regarding the vaporizer comprises an exchange of a first data between the vaporizer and the communication device over the wireless communication channel; and
the causing the vaporizer to operate consistent with the one or more parameters comprises transmitting data to the vaporizer from the communication device.

12. A method comprising:
accessing, through an operation of an application executing on one or more programmable processors, an information regarding a vaporizer;
presenting the information about the vaporizer using a user interface generated on a display by the one or more processors;
receiving a user input by interaction of a user with the user interface;
determining a location of the vaporizer with respect to one or more beacons or one or more geo-fenced areas; and
causing the vaporizer to operate consistent with one or more parameters determined by the one or more processors in accordance with the user input, the causing the vaporizer to operate consistent with the one or more parameters comprising disabling the vaporizer based on the determined location with respect to the one or more beacons or the one or more geo-fenced areas set by one or more individuals as specific locations in which vaporizer use is not permitted.

13. The method of claim 12, further comprising:
pairing a communication device with the vaporizer, the pairing comprising establishing a wireless communication channel between a first communication hardware of the device and a second communication hardware of the vaporizer, wherein the communication device comprises the one or more processors and the display, wherein the accessing comprises an exchange of a first data between the vaporizer and the communication device over the wireless communication channel, and wherein the causing the vaporizer to operate consistent with the one or more parameters comprises transmitting data to the vaporizer from the communication device.

14. The method of claim 13, wherein the information comprises one or more of desired effects, one or more user reviews, one or more recommendations of use, one or more crowdsourced information, and one or more cartridge information.

15. The method of claim 13, wherein the causing the vaporizer to operate consistent with one or more parameters comprises associating the vaporizer with a purchase location.

* * * * *